US012751926B2

(12) United States Patent
Geoerg et al.

(10) Patent No.: US 12,751,926 B2
(45) Date of Patent: Oct. 6, 2026

(54) TABLETING OF SPECIFIC POLYMER STABILIZERS

(71) Applicant: BASF SE, Ludwigshafen am Rhein (DE)

(72) Inventors: Yean Yik Geoerg, Ludwigshafen (DE); Thomas Georg Gfroerer, Kaisten (CH); Holger Ruckdaeschel, Ludwigshafen (DE); Shyam Sundar Sathyanarayana, Ludwigshafen (DE); Lothar Seidemann, Ludwigshafen (DE); Heinz Herbst, Kaisten (CH)

(73) Assignee: BASF SE, Ludwigshafen am Rhein (DE)

( * ) Notice: Subject to any disclaimer, the term of this patent is extended or adjusted under 35 U.S.C. 154(b) by 1005 days.

(21) Appl. No.: 17/623,675

(22) PCT Filed: Jul. 6, 2020

(86) PCT No.: PCT/EP2020/069016
§ 371 (c)(1),
(2) Date: Dec. 29, 2021

(87) PCT Pub. No.: WO2021/005011
PCT Pub. Date: Jan. 14, 2021

(65) Prior Publication Data

US 2022/0249383 A1 Aug. 11, 2022

(30) Foreign Application Priority Data

Jul. 9, 2019 (EP) .................................... 19185298

(51) Int. Cl.
*A61K 9/20* (2006.01)

(52) U.S. Cl.
CPC .......... *A61K 9/2095* (2013.01); *A61K 9/2018* (2013.01); *A61K 9/2027* (2013.01); *A61K 9/2031* (2013.01)

(58) Field of Classification Search
CPC .............................. C08K 5/005; A61K 9/2095
See application file for complete search history.

(56) References Cited

U.S. PATENT DOCUMENTS

| | | | |
|---|---|---|---|
| 5,593,619 | A | 1/1997 | Bottelberghe et al. |
| 5,892,128 | A | 4/1999 | Banhardt et al. |

(Continued)

FOREIGN PATENT DOCUMENTS

| | | | | |
|---|---|---|---|---|
| CN | 101203567 A | 6/2008 | | |
| DE | 19628359 A1 * | 9/1997 | ............. | C08J 3/226 |

(Continued)

OTHER PUBLICATIONS

Teng Y et al: "Systematical approach of formulation and process development using roller compaction", European Journal of Pharmaceutics and Biopharmaceutics, Elsevier Science Publishers B. V., Amsterdam, NL, vol. 73, No. 2, Oct. 1, 2009 (Oct. 1, 2009), pp. 219-229.

(Continued)

*Primary Examiner* — Susan D Leong
*Assistant Examiner* — Vipul Malik
(74) *Attorney, Agent, or Firm* — Faegre Drinker Biddle & Reath LLP

(57) ABSTRACT

The present disclosure relates to a method for manufacturing a tablet including (A) filling a starting material, which is in a solid form, in a first open cavity, which is formed by a first punch and a die, to obtain a second open cavity, which is filled at least partly with the starting material, (B) closing the second open cavity by a second punch to obtain a first dosed cavity, (Continued)

(C) compressing the starting material at a compression temperature below 37° C. by moving at least one out of the first punch and the second punch to obtain a second closed cavity, which has a smaller volume than the first closed cavity, which results in formation of a trapped tablet of the starting material in the second closed cavity, (D) removing the trapped tablet to obtain the tablet, which has a tablet temperature below 37° C. directly after removal.

11 Claims, 6 Drawing Sheets

(56) References Cited

U.S. PATENT DOCUMENTS

| | | | | |
|---|---|---|---|---|
| 2003/0146542 | A1 | 8/2003 | Fatnes et al. | |
| 2003/0193041 | A1* | 10/2003 | Semen | C08K 5/13 252/400.24 |
| 2006/0276571 | A1 | 12/2006 | Sharma et al. | |
| 2009/0011037 | A1 | 1/2009 | Pipkin et al. | |
| 2009/0081289 | A1* | 3/2009 | Madsen | A61J 3/10 264/238 |
| 2009/0093572 | A1* | 4/2009 | Gugumus | C08K 5/098 524/95 |
| 2017/0087789 | A1* | 3/2017 | Ingo | B30B 15/302 |
| 2017/0274351 | A1* | 9/2017 | Hitomi | B01J 20/3042 |
| 2022/0142928 | A1* | 5/2022 | Guha | A61K 9/5026 |

FOREIGN PATENT DOCUMENTS

| | | | |
|---|---|---|---|
| EP | 0782994 | A1 | 7/1997 |
| EP | 1888686 | B1 | 1/2013 |
| JP | H05-57726 | A | 3/1993 |
| JP | 2001-123021 | A | 5/2001 |
| JP | 2002-275326 | A | 9/2002 |
| JP | 2004-292710 | A | 10/2004 |
| JP | H05057726 | | 10/2012 |
| WO | 01/62833 | A1 | 8/2001 |
| WO | 02/36677 | A1 | 5/2002 |
| WO | WO-2008/003605 | A1 | 1/2008 |
| WO | 2008033410 | A1 | 3/2008 |

OTHER PUBLICATIONS

International Search Report for PCT/EP2020/069016 mailed Sep. 14, 2020, 2 pages.

International Preliminary Report on Patentability received for PCT Patent Application No. PCT/EP2020/069016, mailed on Jan. 20, 2022, 7 pages.

European Search Report for EP Patent Application No. 19185298.7, Issued on Dec. 19, 2019, 3 pages.

* cited by examiner

TABLETING OF SPECIFIC POLYMER STABILIZERS

CROSS REFERENCE TO RELATION APPLICATION(S)

The present application is a national stage entry under 35 U.S.C. § 371 of International Application No. PCT/EP2020/069016 filed on Jul. 6, 2020, which claims priority to European Application No. 19185298.7 filed on Jul. 9, 2019, the contents of which are incorporated by reference in their entirety.

FIELD OF THE INVENTION

The current invention relates to a method for manufacturing a tablet, which comprises a polymer stabilizer or a mixture of polymer stabilizers as a starting material, which method comprises the step of compressing the starting material in a cavity formed by two punches and a die to obtain the tablet. A further embodiment is the tablet out of the starting material. A further embodiment is a method for manufacturing a stabilized polymer, which comprises the step of incorporating the tablet out of the starting material into a polymer, which is a polyolefin, a polystyrene or a mixture thereof, to obtain the stabilized polymer. A further embodiment is the use of the tablet out of the starting material for a dust-free handling of its components at manufacturing of the stabilized polymer.

BACKGROUND

An organic polymer, which is used as a constructive material to build or to be part of an article, is susceptible to degradation by oxidation, heat or light. There is a short-term degradation, which occurs at processing of the polymer, for example when the polymer obtained from the polymer synthesis is mechanically transformed into a desired final article or into an intermediate article. The intermediate article is often the product of a process, which serves to incorporate specifically desired additives into the polymer obtained from the polymer synthesis. The specifically desired additives provide further functional effects to the polymer, e.g. color, or improve existing properties, e.g. mechanical strength or resistance against degradation. The short-time degradation is often characterized by a relatively short exposure to a relatively high process temperature, for example above 80° C. to 330° C., which occurs in many instances in combination with mechanical stress. In contrast to the short-term degradation, the long-term degradation of a polymer, typically in the form of the desired final article, occurs during a foreseen use. The foreseen use of the desired final article might lead to a long-term expose of the polymer towards light, oxygen, increased temperatures, e.g. above room temperature but below 80° C., water or aggressive chemicals.

It is long known to incorporate a polymer stabilizer into an organic polymer for stabilization against degradation by oxidation, heat or light. The incorporation of the polymer stabilizer is typically done for a thermoplastic polymer during processing of the polymer, where the heated polymer possesses a reduced viscosity or is close to a liquid state and thus a homogenous distribution of the polymer stabilizer in the polymer is supported. For a thermo-set polymer, the incorporation of the polymer stabilizer is typically done prior to hardening, for example by a homogenous incorporation into a precursor for the thermo-set polymer. Dependent on the chemical type of the polymer, the polymer stabilizer differs and vary often, specific mixtures of two or more polymer stabilizers are incorporated. A polymer stabilizer is very often solid at room temperature and obtained from its synthesis in the form of a powder. Practical problems arise at the actual incorporation of a polymer stabilizer in powder form or a mixture of polymer stabilizers in powder form. Handling of a powder is prone to an easy generation of dust. Dust is critical from an occupational health perspective for workers at a manufacturing plant, from a plant safety perspective, e.g. a dust explosion, and from a plant cleanness perspective, e.g. a dust soiling of the plant equipment. Furthermore, the incorporation of the powder into a polymer is typically not conducted in a batch-wise manner. Instead, a continuous dosing of a powder to a polymer, which is processed in a continuous way for example in an extruder, in an amount with is typically below 0.5% by weight of the polymer is prone to fluctuations of the really incorporated amount in a specific moment of time. Hence, a large overall amount of polymer contains afterwards statistically the same amount of polymer stabilizer, but this not necessarily true for single units out of the overall amount of polymer.

Several approaches are known for providing a suitable dust-free dosage form of a polymer stabilizer or a mixture of polymer stabilizers. One direction is to provide a suitable dust-free dosage form without adding a further ingredient, i.e. an ingredient not needed as polymer stabilizer. For example, the polymer stabilizer in powder form or the mixture of polymer stabilizers in powder form is press-agglomerated via a roll compaction to obtain flakes. Another approach is the formation of pastilles from the polymer stabilizer in powder form or the mixture of polymer stabilizers in powder form by melting the mentioned one and let single drops of the melt solidify on a cooled surface. Another approach is the formation of pellets from the polymer stabilizer in powder form or the mixture of polymer stabilizers in powder form by heating and kneading the mentioned one in an extruder at a temperature above the softening point of at least one of the polymer stabilizers, extruding the heated mass through a die to form a warm strand and cutting the warm strand into pellets. Another direction is to provide a suitable dust-free dosage form by adding a further ingredient, i.e. an ingredient not needed as polymer stabilizer. The further ingredient, sometimes called compaction aid or binder, in case of a polymeric further ingredient also masterbatch polymer or carrier polymer, acts typically as a type of hot-melt glue for the polymer stabilizer powder respectively its particles. Whether the polymer stabilizer or one or more polymer stabilizers of the mixture of polymer stabilizers melts to at least a major part depends on the applied temperature and the chemical nature of the further ingredient in relation to the polymer stabilizer, particularly whether a type of mutual solubility exists. While it is clear that addition of a further ingredient at least dilutes active content of polymer stabilizer in the dosage form and incorporates additionally into the polymer, this direction might still have its advantages. Particularly, a dosage form of a polymer stabilizer or a mixture of polymer stabilizers might be obtained initially dust-free simply by sieving respectively screening dust at the end of its manufacturing. However, attrition resistance of an initially dust-free dosage form is a property, which gets relevant in view of transport of the dosage form and associated formation of dust.

WO 2008-033410 relates to high concentration pelletized additive concentration or polymer stabilization agent or blends and their preparations, which can be used in various polymerization processes to enhance stability. The pelletized additive concentrates comprise at least 10 wt. % of a carrier polymer and are obtained in the examples by heating the additive mixtures together with the carrier polymer in an extruder above the melting temperature of the carrier polymer but lower than the melting temperature of the main additive, which is followed by cutting the warm strands into pellets.

JP H05-057726 relates to a method wherein a powdery flame-retardant is made into a granulated product by using a tableting-type compression granulating machine and grinding the obtained item. The obtained item is compression-molded and possesses grooves on its surface. In the examples, a powdered polycarbonate type fire-retardant with the trade name FG 8500 of Teijin Chemicals Ltd is employed and discs with a diameter of 45 mm and a height of 5 mm are produced with a compression pressure of 200 $kg/cm^2$ (2 MPa) or 250 $kg/cm^2$ (2 MPa) at normal temperature. In the inventive examples, the discs are impressed with four grooves. In the comparative example, no groove is impressed. All tablets are crushed in an oscillator-type granulator with a sieve to obtain the desired granulated product in yields between 50 to 90 wt. %.

U.S. Pat. No. 5,593,619 relates to compositions containing granulated hexabromocyclododecane flame retardant products, flame retardant formulations containing products, and to a process for forming the granulated flame-retardant products, wherein the granulated product is characterized as having a friability loss of less than about 8 percent. One process comprises (a) heating rolls of a pressure compactor to a temperature of greater than about 35° C., (b) feeding a powdered material to the heated compactor rolls and (c) applying an amount of force to the powdered material sufficient to form a compacted material, whereby there is more than a 5 percent increase in compaction efficiency. Compaction efficiency relates to the intrinsic feature of roll compaction that a portion of the product must be recycled to the roll compactor due to fines generation in a granulator. The granulator serves to comminute the plates obtained as the direct product of roll compaction. One process forms improved granulated flame retardant product predominant in hexabromocyclododecane and comprises (a) heating pressure compactor rolls to a temperature of greater than about 35° C., (b) feeding the hexabromocyclododecane predominant product in powder form to the pressure compactor, (c) applying an amount of hydraulic pressure to the compactor rolls sufficient to compact the product, and (d) granulating the product so as to form product particles having an average size of between 0.5 and less than about 2 millimeters. An improved granulated flame retardant product predominant in hexabromocyclododecane is provided, wherein the granulated product is characterized as having a friability loss of less than about 8 percent. In example 1, tablets out of hexabromocyclododecane are manufactured. Each tablet has a diameter of 29 mm, a weight of 10 g and compression-pressure of 89000 N is applied (135 MPa). Tablets obtained at a tablet press housing temperature of 25° C. have a friability loss in a milling test of 13.2%, whereas tablet press housing temperatures of 50° C. or 100° C. change this towards 0.4% or 0.3%. The powder temperature is stated as 25° C. at all three examples.

DE 19628359 discloses a stabilizer concentrate for polyamides, which comprises several stabilizer components and a wax binder. After intimately mixing with no liquid additives and without heating, the mixture is compacted to tablets under a compression force such that the mixture is heated to a temperature of at least 40° C. In example 2, 56 wt. % 2-mercapto-1-methylimidazol, 7 wt % copper(I)-iodide, 3 wt % diphosphorus pentasulfide, 6 wt. 2,6-di-tert-butyl-p-cresol, 1 wt. % highly dispersed silicic acid and 27 wt. % octadecanamide are mixed to form a powder mixture with a temperature of around 35° C. The powder mixture is fed into a rotary tablet press, which results in tablets with a diameter of 3 mm and a temperature of 57° C. A reaction of diphosphorus pentasulfide and 2-mercapto-1-methylimidazol with copper(I) iodide is reported.

U.S. Pat. No. 5,892,128 discloses benzoyl peroxide, which is inactivated temporarily by compressing benzoyl peroxide desensitized by dimethyl phthalate to tablets. In the example, a mixture of 50 wt. % benzoyl peroxide in powder form and 50 wt. % dimethyl phthalate is fed into a tablet pressing apparatus. Tablets with 7 mm diameter and 2 mm height are produced. No polymerization or crosslinking happens when these tablets are brought in direct contact with typical mixtures of free-radical polymerizable or crosslinkable monomers.

SUMMARY

There is still a need for further solid dosage forms of a polymer stabilizer or a mixture of polymer stabilizers being originally in the form of powders as starting material. In a first aspect, the manufacturing of a dosage form respectively of the dosage form units should ideally occur without warming of the polymer stabilizers or at least minimize it. First, this saves process energy, which would be necessary for warming of the polymer stabilizers either by direct heating or by indirect heating, i.e. mechanical stress is transformed into thermal energy, which results in a clear increase of the temperature of the processed polymer stabilizers. Secondly, this also avoids an unnecessary exposure of the polymer stabilizers to an increased temperature. While an unnecessary exposure is in general to be avoided, an individual polymer stabilizer might also undergo a phase change, e.g. an originally crystalline material is transferred into a viscous state. Furthermore, the manufacturing of a dosage form should ideally occur without generation of deficient product, i.e. the employed starting material of the polymer stabilizer should be processed ideally to 100% into the dosage form in one run. In other words, no rejects should be generated, even if the rejects are in a form that they can be re-employed directly as a starting material again. An example for removing rejects is a sieving of the desired dosage form to obtain an initially dust-free dosage form, if the applied manufacturing of a dosage form generates also fines as by-products. In a second aspect, a dosage form of a polymer stabilizer or a mixture of polymer stabilizers should after its manufacturing stay stable during storage and transport. Particularly, an initially dust-free dosage form might again generate dust respectively fines by attrition of the dosage form units versus each other at exposure to vibrations, for example during filling into a bag, at a transportation of the filled bag or at feeding operations of the dosage form units for incorporation into a polymer to be stabilized. Accordingly, a certain level of attrition resistance of the dosage form is desirable. In a third aspect, the units of a dosage form should ideally be uniform in its shape and weight, since this allows a more accurate feeding of the dosage form units at the incorporation into a polymer to be stabilized. A consequence of a more accurate feeding is especially at a continuous dosage into a polymer to be stabilized that the con-centrations of the polymer stabilizers are less fluctuating in the stabilized polymer. In other words, the local concentration of polymer stabilizers at a certain part of the stabilized polymer shows less deviation from an average concentration of polymer stabilizers in the whole stabilized polymer. If the feeding of the dosage form units occurs at the incorporation into the polymer to be stabilized at a stage, where the polymer is itself still present as solid units, e.g. pellets, then it is advantageous that the dosage form units are similar in shape and weight to the solid units of the polymer. This disfavors that a mixture of the dosage form units and the solid units of the polymer to be stabilized segregate while being transported as a mixture. An example for such a transport is a pneumatic transport of a mixture of a polymer to be stabilized and the foreseen stabilizers from a storage facility to the equipment for the incorporation into the polymer, e.g. an extruder. In a fourth aspect, the dosage form of a polymer stabilizer or a mixture of polymer stabilizers should ideally be free of the presence of an auxiliary ingredient. The auxiliary ingredient might be present only during a manufacturing of the dosage form, e.g. addition of a solvent, which is afterwards removed. The auxiliary ingredient might be present permanently, i.e. the composition of the dosage form contains an auxiliary ingredient, which first dilutes the content of a polymer stabilizer or a mixture of polymer stabilizers in the dosage form and secondly would be incorporated into the polymer to be stabilized. In a fifth aspect, the dosage form should ideally work without the requirement of a chemical reaction taking place between two or more polymer stabilizers. This allows more flexibility for a composition of polymer stabilizers suitable for the dosage form and thus adapting a composition of polymer stabilizers primarily towards the stabilization need of the polymer to be stabilized. In a sixth aspect, a correct selection of polymer stabilizers or a ratio between them in a mixture for a dosage form has to be found in view of the foreseen incorporation in a polymer to be stabilized. Stabilization of a polymer is supported by an ideally homogenous distribution of individual polymer stabilizer molecules throughout the polymer to be stabilized. Or in case that a polymer stabilizer is not soluble as an individual molecule in the polymer to be stabilized, aggregates of individual molecules of the insoluble polymer stabilizer or even larger particles out of aggregates of individual polymer stabilizer molecules are distributed homogenously in the polymer to be stabilized. The potential influence of a dosage form for a distribution of a polymer stabilizer or a mixture of polymer stabilizers is obvious by considering that at the beginning, all polymer stabilizers are concentrated in the dosage form, whereas afterwards all polymer stabilizers are ideally homogenously distributed in the polymer to be stabilized. An inhomogeneous distribution of polymer stabilizers in the polymer to be stabilized might also get noticed differently to a decreased stability against degradation of the stabilized in comparison to a polymer stabilized by a more perfect initial distribution like in case of mixing powders of polymer and polymer stabilizers. For example, unevenly distributed polymer stabilizers in the stabilized polymer might disturb surface properties in case a thin polymer film manufacturing from the stabilized polymer or might lead to clogging of filters or nozzles in case a spin-extrusion of the stabilized polymer. The nature of the polymer to be stabilized interacts with a suitable selection of polymer stabilizers or the ratio between them, For example, polyamide turns on its way to a molten state into a type of solvent comparable to dime-thylsulfoxide, whereas a polyolefin typically turns on its way to a molten state only into a type of solvent like n-hexane or decaline. Hence, there is less potential for correction of the distribution of the polymer stabilizers in a polyolefin during its processing at a high temperature than in polyamide.

DETAILED DESCRIPTION

It has now been found a method for manufacturing a tablet, which comprises the steps of (A) filling a starting material, which is in a solid form, in a first open cavity, which is formed by a first punch and a die, to obtain a second open cavity, which is filled at least partly with the starting material, (B) closing the second open cavity by a second punch to obtain a first closed cavity, (C) compressing the starting material at a compression temperature below 37° C. by moving at least one out of the first punch and the second punch to obtain a second closed cavity, which has a smaller volume than the first closed cavity, which results in formation of a trapped tablet of the starting material in the second closed cavity, (D) removing the trapped tablet to obtain the tablet, which has a tablet temperature below 37° C. directly after removal, wherein the steps (A), (B), (C) and (D) are conducted in a tablet press, wherein the starting material is solid at 37° C. and 101.32 KPa and consists out of (i) 60 to 100 wt. % of a first polymer stabilizer, which is
- (i-1) tris(2,4-ditert-butylphenyl) phosphite (CAS-No. 31570-04-4),
- (i-2) bis(2,4-dicumylphenyl) pentaerythritol diphosphite (CAS-No. 154862-43-8),
- (i-3) bis(2,4-ditert-butylphenyl)pentaerythritol diphosphite (CAS-No. 26741-53-7),
- (i-4) tetrakis-[3-(3,5-ditert-butyl-4-hydroxy-phenyl)-propionyloxymethyl]methane (CAS-No. 6683-19-8),
- (i-5) 3-(3,5-ditert-butyl-4-hydroxy-phenyl)-propionic acid stearyl ester (CAS-No. 2082-79-3),
- (i-6) 3-(3,5-ditert-butyl-4-hydroxy-phenyl)-N-[6-[3-(3,5-ditert-butyl-4-hydroxy-phenyl)propanoylamino] hexyl]propanamide (CAS-No. 23128-74-7),
- (i-7) 3-(3,5-ditert-butyl-4-hydroxyphenyl)-N'-[3-(3,5-ditert-butyl-4-hydroxyphenyl)-propanoyl]propanehydrazide (CAS-No. 3268-78-8),
- (i-8) 2-[2-[2-[3-(3-tert-butyl-4-hydroxy-5-methyl-phenyl)propanoyloxy]ethoxy]ethoxy]ethyl 3-(3-tert-butyl-4-hydroxy-5-methyl-phenyl)propanoate (CAS-No. 36443-68-2),
- (i-9) 4-[[3,5-bis[(3,5-ditert-butyl-4-hydroxy-phenyl) methyl]-2,4,6-trimethyl-phenyl]methyl]-2,6-ditert-butyl-phenol (CAS-No. 1709-70-2),
- (i-10) 1,3,5-tris(3,5-ditert-butyl-4-hydroxybenzyl)-1,3,5-triazine-2,4,6(1H,3H,5H)-trione (CAS-No. 27676-62-6),
- (i-11)bis[3,3-bis(4'-hydroxy-3'-tert-butylphenyl) butanoic acid] glycol ester (CAS-No. 32509-66-3),
- (i-12) N,N-dioctadecylhydroxylamine (CAS-No. 123250-74-8),
- (i-13)dodecyl 3-(3-dodecoxy-3-oxo-propyl)sulfanylpropanoate (CAS-No. 123-28-4),
- (i-14)octadecyl 3-(3-octadecoxy-3-oxo-propyl)sulfanylpropanoate (CAS-No. 693-36-7),
- (i-15)pentaerythritol tetrakis[3-dodecylthio proprionate] (CAS-No. 29598-76-3), (i-16)bis(2,2,6,6-tetramethyl-4-piperidyl) decanedioate (CAS-No. 52829-07-9),
(i-17)(2-hydroxy-4-octoxy-phenyl)-phenyl-methanone (CAS-No. 1843-05-6),
(i-18) 2-tert-butyl-6-(5-chlorobenzotriazol-2-yl)-4-methyl-phenol (CAS-No. 3896-11-5),
(i-19) 2-(4,6-diphenyl-1,3,5-triazin-2-yl)-5-hexoxy-phenol (CAS-No. 147315-50-2),
(i-20) 2-[4,6-bis(4-phenylphenyl)-1,3,5-triazin-2-yl]-5-(2-ethylhexoxy)phenol (CAS-No. 204583-39-1),
(i-21) 2-[4,6-bis(2,4-dimethylphenyl)-1,3,5-triazin-2-yl]-5-[3-(2-ethylhexoxy)-2-hydroxy-propoxy]phenol (CAS-No. 137658-79-8),
(i-22) butanedioic acid, 1,4-dimethyl ester, polymer with 4-hydroxy-2,2,6,6-tetramethyl-1-piperidineethanol (CAS-No. 65447-77-0),
(i-23) N,N',N",N'"-tetrakis-(2,4-bis[N-(1-cyclohexyloxy-2,2,6,6-tetramethylpiperidin-4-yl)-butylamino]-1,3,5-triazin-6-yl)-1,5,8,12-tetrazadodecane (CAS-No. 122587-07-9),
(i-24) N,N',N",N'"-Tetrakis-(2,4-bis[N-(1-cyclohexyloxy-2,2,6,6-tetramethylpiperidin-4-yl)-butylamino]-1,3,5-triazin-6-yl)-1,5,8,12-tetrazadodecane (CAS-No. 106990-43-6),
(i-25) N,N'-bis-(2,4-bis[N-(1-propoxy-2,2,6,6-tetramethylpiperidin-4-yl)-butylamino]-1,3,5-triazin-6-yl)-N,N'-bis[N-(1-propoxy-2,2,6,6-tetramethylpiperidin-4-yl)]-1,8-diazaoctane (CAS-No. 1271737-36-0),
(i-26) poly[[6-[butyl(2,2,6,6-tetramethyl-4-piperidinyl) amino]-1,3,5-triazine-2,4-diyl] [(2,2,6,6-tetramethyl-4-piperidinyl)imino]-1,6-hexanediyl[(2,2,6,6-tetramethyl-4-piperidinyl)imino]], α[[6-[[4,6-bis (dibutylamino)-1,3,5-triazin-2-yl](2,2,6,6-tetramethyl-4-piperidinyl)amino]hexyl](2,2,6,6-tetramethyl-4-piperidinyl)amino]-ω-[4,6-bis (dibutylamino)-1,3,5-triazin-2-yl]-(CAS-No. 195300-91-5),
(i-27) poly[[6-[butyl(2,2,6,6-tetramethyl-1-propoxy-4-piperidinyl)amino]-1,3,5-triazine-2,4-diyl][(2,2,6,6-tetramethyl-1-propoxy-4-piperidinyl)imino]-1,6-hexanediyl[(2,2,6,6-tetramethyl-1-propoxy-4-piperidinyl)imino]], α[[6-[[4,6-bis(dibutylamino)-1,3,5-triazin-2-yl](2,2,6,6-tetramethyl-1-propoxy-4-piperidinyl)amino]hexyl](2,2,6,6-tetramethyl-1-propoxy-4-piperidinyl)amino]-ω-[4,6-bis (dibutylamino)-1,3,5-triazin-2-yl]-(CAS-No. 297748-93-7),
(i-28) poly[[6-[(1,1,3,3-tetramethylbutyl)amino]-1,3,5-triazine-2,4-diyl][(2,2,6,6-tetra-methyl-4-piperidinyl)imino]-1,6-hexanediyl[(2,2,6,6-tetramethyl-4-piperidinyl)imino]] (CAS-No. 71878-19-8),
(i-29)tetrakis(1,2,2,6,6-pentamethyl-4-piperidyl) butane-1,2,3,4-tetracarboxylate (CAS-No. 91788-83-9), or a mixture thereof, (ii) 0 to 40 wt. % of a second polymer stabilizer, which is zinc stearate, calcium stearate, magnesium stearate or a mixture thereof, (iii) 0 to 34 wt. % of a third polymer stabilizer, which is zinc oxide, hydrotalcite, sodium benzoate or a mixture thereof, (iv) 0 to 20 wt. % of a further ingredient, which is different to the first polymer stabilizer, the second polymer stabilizer and the third polymer stabilizer, wherein the sum of components (i), (ii), (iii) and (iv) is 100 wt. %, wherein the tablet has a weight above 20 mg and below 330 mg and a cross-section dimension above 3 mm and below 18 mm.

In step (A), the starting material is filled into the first open cavity in a solid form. Hence, gravimetry supports the filling, especially in case of a gravimetry-feed is used, for example a feeding shoe of a tablet press. Solid form of the starting material excludes that the starting material is a liquid or theoretically a gas at step (A). The starting material at step (A) has preferably a starting material temperature below 37° C., very preferably below 32° C., particularly above 10° C. and below 30° C., very particularly above 15° C. and below 28° C., especially above 18° C. and below 26° C. and very especially, the starting material temperature is room temperature between 20 and 25° C.

Step (A) is preferably conducted at a temperature below 37° C., very preferably below 32° C., particularly above 10° C. and below 30° C., very particularly above 15° C. and below 28° C., especially above 18° C. and below 26° C. and very especially, step (A) is conducted at room temperature between 20 and 25° C.

The solid form of the starting material at step (A) supports a free-flowing of the starting material. The solid form consists out of solid particles, wherein each individual particle is small enough to drop into the open cavity formed by the first punch and the die. For example, the solid form of the starting material is a powder. Preferably, the starting material has a mean particle size as determined by light scattering above 15 μm and below 1000 μm, very preferably above 18 μm and below 900 μm and particularly above 20 μm and below 800 μm. The light scattering is for example analyzed based on Mie and Fraunhofer scattering model under dry dispersion pressure of 0.2 bar. Preferably, the starting material has a bulk density above 300 g/L and below 950 g/L as determined by DIN EN ISO 17892-3, very preferably above 350 g/L and below 900 g/L, particularly above 360 g/L and below 800 g/L and very particularly above 370 g/L and below 750 g/L. At step (A), the second open cavity is filled preferably completely with the starting material. Some air is still also contained, which fills the residual volume since the particles of the solid form of the starting material does not fill entirely a given volume.

Preferred is a method for manufacturing a tablet, wherein the starting material is in the solid form of a powder.

Preferred is a method for manufacturing a tablet, wherein the starting material has a mean particle size above 15 μm and below 1000 μm as determined by light scattering.

Preferred is a method for manufacturing a tablet, wherein the starting material has a bulk density above 300 g/L and below 950 g/L as determined by DIN EN ISO 17892-3.

At step (B), the closing of the second open cavity by a second punch to obtain a first closed cavity is to be understood as a mechanical closing but not as a gas-tight closing. Despite of a fitting of the punches and the die often towards a remaining distance of sometimes only 1/100 mm, there is still not a gas-tight closing. Hence, trapped gas like air can escape to a certain extent from the first closed cavity at step (B) and the second closed cavity at step (C). Otherwise, a pressurized gas content in the trapped tablet could lead to a destruction at removing the trapped tablet, for example by exploding or by uncontrolled ejecting.

Step (B) is preferably conducted at a temperature below 37° C., very preferably below 32° C., particularly above 10° C. and below 30° C., very particularly above 15° C. and below 28° C., especially above 18° C. and below 26° C. and very especially, step (B) is conducted at room temperature between 20 and 25° C.

At step (C), the starting material is cold-compacted. By cold compaction, it is meant that no external heat is added during the compaction operation and that compaction is substantially carried out by mechanical pressure. Step (C) does not involve an external heat input into the starting material, particularly not an external heat input which could lead to a phase transfer of the starting material. The starting material within the die experiences a mechanical deformation which lead to an increase of points of contact between the particles of the starting materials. These contacts bond and increase cohesion between particles, which transforms the starting material to the trapped tablet. Preferably, the compressing at step (C) takes place with a compression pressure above 90 MPa and below 600 MPa, very preferably above 95 MPa and below 500 MPa and particularly above 97 MPa and below 470 MPa. The compression pressure is built up by the relative approaching of the two punches towards each other and forming the second closed cavity. Moving at least one out of the first punch and the second punch to obtain a second closed cavity is for example that both punches moves towards each other, that one of the two punches stays and only the other punch moves towards the staying punch or that both punches move in the same direction, but one of the two punches moves faster resulting in an overall second closed cavity, which has a smaller volume. The reached minimum volume of the second closed cavity during the moving of at least one out of the first and the second punch is essentially the volume of the tablet. Essentially refers here to a certain elasticity of the compressed tablet, i.e. a minor expansion after removal of the compression pressure. Preferably, the compression temperature at step (C) is below 32° C., very preferably above 10° C. and below 30° C., particularly above 15° C. and below 28° C., very particularly above 18° C. and below 26° C. and especially, the compressing temperature is room temperature between 20 and 25° C. The compression temperature is similar to the temperature of the tablet, if the tablet is directly removed afterwards and the tablet temperature is determined directly afterwards. Additionally, the temperature of the two punches and the die have reached a constant level by running the method of manufacturing a tablet for a certain time, e.g. at least 40 tablets have been manufactured with the two punches and the die.

Step (C) is preferably conducted at a temperature below 37° C., very preferably below 32° C., particularly above 10° C. and below 30° C., very particularly above 15° C. and below 28° C., especially above 18° C. and below 26° C. and very especially, step (D) is conducted at room temperature between 20 and 25° C.

Preferred is a method for manufacturing a tablet, wherein the compressing at step (C) takes place with a compression pressure above 90 MPa and below 600 MPa.

At step (D), the trapped tablet from step (C) is removed. This requires that the second closed cavity is opened. For example, one out of the first punch and of the second punch is removed from the die and thus leads to an open cavity. Preferably, the other punch ejects the tablet by moving in the die. The tablet temperature of the tablet is understood as the temperature of the tablet directly after removal of the obtained tablet. Preferably, the tablet temperature at step (D) is below 32° C., very preferably above 10° C. and below 30° C., particularly above 15° C. and below 28° C., very particularly above 18° C. and below 26° C. and especially, the tablet temperature is room temperature between 20 and 25° C. The tablet temperature is similar to the compression temperature at step (C), if the tablet is directly removed afterwards and the tablet temperature is determined directly afterwards. Additionally, the temperature of the two punches and the die have reached a constant level by running the method of manufacturing a tablet for a certain time, e.g. at least 40 tablets have been manufactured with the two punches and the die.

Step (D) is preferably conducted at a temperature below 37° C., very preferably below 32° C., particularly above 10° C. and below 30° C., very particularly above 15° C. and below 28° C., especially above 18° C. and below 26° C. and very especially, step (D) is conducted at room temperature between 20 and 25° C.

The compression temperature and the tablet temperature are preferably below 32° C., very preferably above 10° C. and below 30° C., particularly above 15° C. and below 28° C., very particularly above 18° C. and below 26° C. and especially, the compression temperature and the tablet temperature are room temperature between 20 and 25° C.

Preferred is a method for manufacturing a tablet, wherein the compression temperature is below 32° C. and the tablet temperature is below 32° C.

The steps (A), (B), (C) and (D) are preferably conducted at a temperature below 37° C., very preferably below 32° C., particularly above 10° C. and below 30° C., very particularly above 15° C. and below 28° C., especially above 18° C. and below 26° C. and very especially, the steps (A), (B), (C) and (D) step (D) are conducted at room temperature between 20 and 25° C.

Preferred is a method for manufacturing a tablet, wherein the steps (A), (B), (C) and (D) are conducted at a temperature below 37° C.

Steps (A), (B), (C) and (D) take place in a tablet press, preferably an eccentric tablet press or a rotary tablet press. The tablet press comprises the die, the first punch and the second punch. Preferably, the tablet press comprises the die, the first punch and the second punch and a feeding device for filling the starting material into the first open cavity in step (A). For example, tablet presses for concave tablets are suitable.

Preferred is a method for manufacturing a tablet, wherein the tablet press is an eccentric tablet press or a rotary tablet press.

The method for manufacturing a tablet generates significantly less fines in comparison to many other cold-compaction methods. In case of a sieving of the obtained tablet or a plurality of obtained tablets, preferably less than 3 wt. % of the starting material employed at step (A) is removed by a sieving of the tablet with a sieve having pores smaller than half of the cross-section dimension of the tablet and larger than 10% of the cross-section dimension of the tablet. Very preferably, less than 2 wt. % are removed by sieving, particularly less than 1 wt. % are removed by sieving and very particularly less than 0.5 wt. % are removed. Preferably, the method for manufacturing of a tablet is free of a sieving of the obtained tablet or a plurality of obtained tablets.

Preferred is a method for manufacturing a tablet, wherein the tablet or a plurality of tablets is not sieved.

Preferred is a method for manufacturing a tablet, wherein the tablet from step (D) is not coated.

The starting material is solid at 37° C. and 101.32 KPa, which means that the melting range of the starting material starts above 37° C. and 101.32 KPa. Preferably, the starting material is solid at 40° C. and 101.32 KPa and dodecyl 3-(3-dodecoxy-3-oxo-propyl)sulfanylpropanoate (CAS-No. 123-28-4) [=(i-13)] is excluded as a component of the starting material, which means that the melting range of the starting material starts above 40° C. Very preferably, the starting material is solid at 43° C. and 101.32 KPa and dodecyl 3-(3-dodecoxy-3-oxo-propyl)sulfanylpropanoate (CAS-No. 123-28-4) [=(i-13)] is excluded as a component of the starting material, which means that the melting range of the starting material starts above 43° C. Particularly, the starting material is solid at 46° C. and 101.32 KPa and dodecyl 3-(3-dodecoxy-3-oxo-propyl)sulfanylpropanoate (CAS-No. 123-28-4) [=(i-13)] is excluded as a component of the starting material, which means that the melting range starts above 46° C.

The primary polymer stabilizers function in a polymer as a short-term processing stabilizer, as a long-term heat stabilizer or as a UV light stabilizer.

Tris(2,4-ditert-butylphenyl) phosphite (CAS-No. 31570-04-4) [=(i-1)] is depicted below

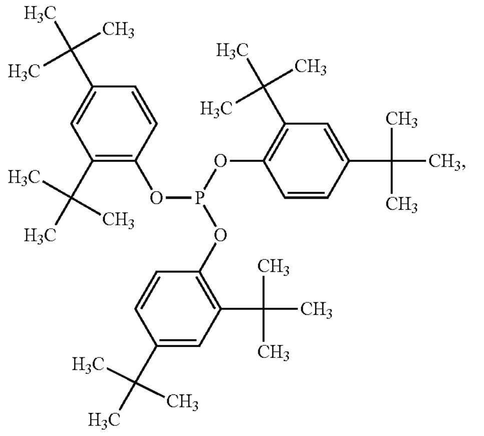 [SMILES: CC(C)(C)c1ccc(OP(Oc2ccc(C(C)(C)C)cc2C(C)(C)C)Oc2ccc(C(C)(C)C)cc2C(C)(C)C)c(C(C)(C)C)c1]

has a melting range of 180-183° C. and is for example contained in Irgafos 168 (TM, commercially available from BASF SE). It functions as a short-term processing stabilizer.

Bis(2,4-dicumylphenyl) pentaerythritol diphosphite (alternative name: 3,9-bis[2,4-bis(1-methyl-1-phenyl-ethyl) phenoxy]-2,4,8,10-tetraoxa-3,9-diphosphaspiro[5.5]undecane) (CAS-No. 154862-43-8) [=(i-2)] is depicted below

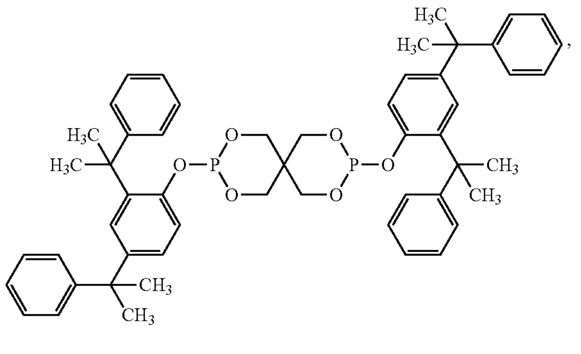 [SMILES: CC(C)(c1ccccc1)c1ccc(OP2OCC3(CO2)COP(Oc2ccc(C(C)(C)c4ccccc4)cc2C(C)(C)c2ccccc2)OC3)c(C(C)(C)c2ccccc2)c1]

has a melting range of around 225° C. and is for example contained in Doverphos S-9228 (TM, commercially available from Dover Chemicals Corp.). It functions as a short-term processing stabilizer.

Bis(2,4-ditert-butylphenyl) pentaerythritol diphosphite (alternative name: 3,9-bis(2,4-ditert-bu-tylphenoxy)-2,4,8,10-tetraoxa-3,9-diphosphaspiro[5.5]undecane) (CAS-No. 26741-53-7) [=(i-3)] is depicted below

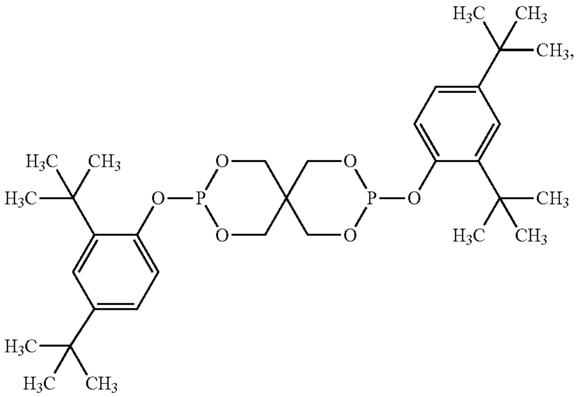 [SMILES: CC(C)(C)c1ccc(OP2OCC3(CO2)COP(Oc2ccc(C(C)(C)C)cc2C(C)(C)C)OC3)c(C(C)(C)C)c1]

has a melting range of around 160° C. and is for example contained in Irgaphos 126 (TM, commercially available from BASF SE). It functions as a short-term processing stabilizer.

Tetrakis-[3-(3,5-ditert-butyl-4-hydroxy-phenyl)-propionyloxymethyl]methane (CAS-No. 6683-19-8) [=(i-4)] is depicted below

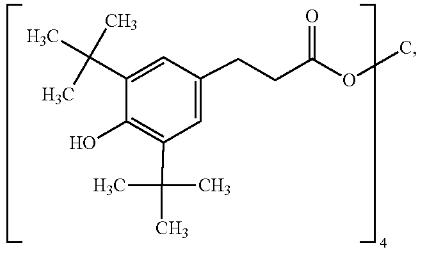

has a melting range of 110-125° C. and is for example contained in Irganox 1010 (TM, commercially available from BASF SE). It functions as a long-term heat stabilizer.

3-(3,5-Ditert-butyl-4-hydroxy-phenyl)-propionic acid stearyl ester (CAS-No. 2082-79-3) [=(i-5)] is depicted below

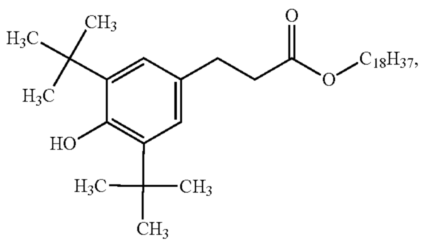

has a melting range of 50-55° C. and is for example contained in Irganox 1076 (TM, commercially available from BAFS SE). It functions as a long-term heat stabilizer.

3-(3,5-Ditert-butyl-4-hydroxy-phenyl)-N-[6-[3-(3,5-ditert-butyl-4-hydroxy-phenyl)propanoylamino]hexyl]propanamide (CAS-No. 23128-74-7) [=(i-6)] is depicted below

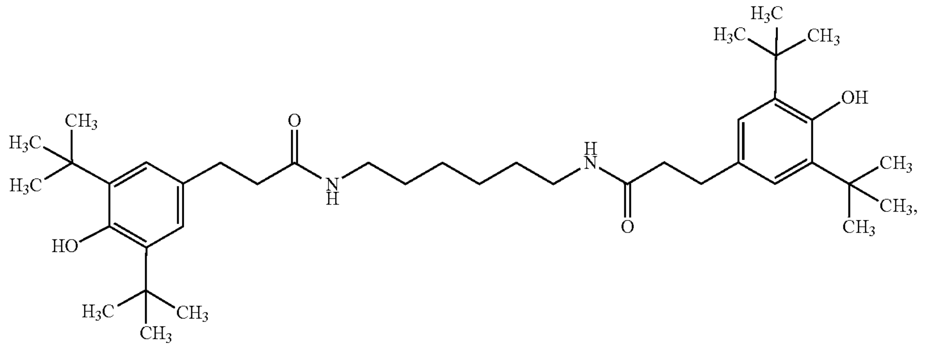 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]

has a melting range of 156-161° C. and is for example contained in Irganox 1098 (TM, commercially available from BASF SE). It functions as a long-term heat stabilizer.

3-(3,5-Ditert-butyl-4-hydroxyphenyl)-N'-[3-(3,5-ditert-butyl-4-hydroxyphenyl)propanoyl]propanehydrazide (CAS-No. 32687-78-8) [=(i-7)] is depicted below

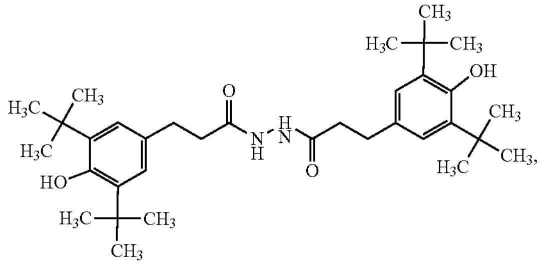 [SMILES: CC(C)(C)c1cc(CCC(=O)NNC(=O)CCc2cc(C(C)(C)C)c(O)c(C(C)(C)C)c2)cc(C(C)(C)C)c1O]

has a melting range of 221-232° C. and is for example contained in Irganox MD 1024 (TM, commercially available from BASF SE). It functions as a long-term heat stabilizer.

2-[2-[2-[3-(3-Tert-butyl-4-hydroxy-5-methyl-phenyl)propanoyloxy]ethoxy]ethoxy]ethyl 3-(3-tert-butyl-4-hydroxy-5-methyl-phenyl)propanoate (CAS-No. 36443-68-2) [=(i-8)] is depicted below

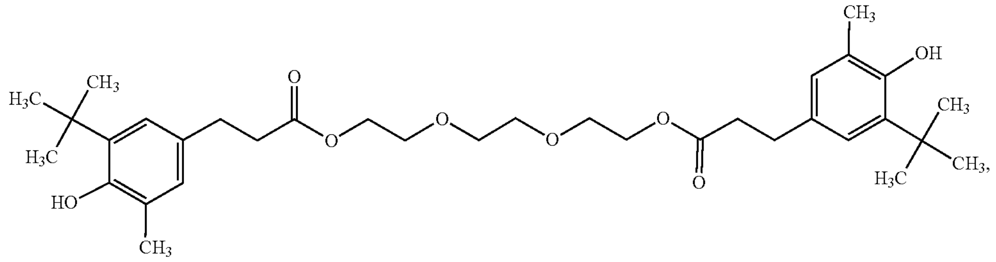 [SMILES: Cc1cc(CCC(=O)OCCOCCOCCOC(=O)CCc2cc(C)c(O)c(C(C)(C)C)c2)cc(C(C)(C)C)c1O]

has a melting range of around 78° C. and is for example contained in Irganox 245 (TM, commercially available from BASF SE). It functions as a long-term heat stabilizer.

4-[[3,5-Bis[(3,5-ditert-butyl-4-hydroxy-phenyl)methyl]-2,4,6-trimethyl-phenyl]methyl]-2,6-ditert-butyl-phenol (CAS-No. 1709-70-2) [=(i-9)] is depicted below

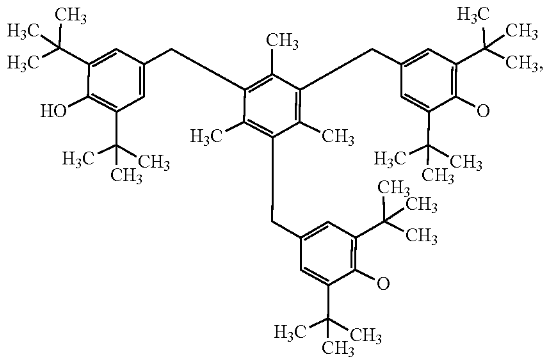

has a melting range of 241-245° C. and is for example contained in Irganox 1330 (TM, commercially available from BASF SE). It functions as a long-term heat stabilizer.

1,3,5-Tris(3,5-ditert-butyl-4-hydroxybenzyl)-1,3,5-triazine-2,4,6(1H,3H,5H)-trione (CAS-No. 27676-62-6) [=(i-10)] is depicted below

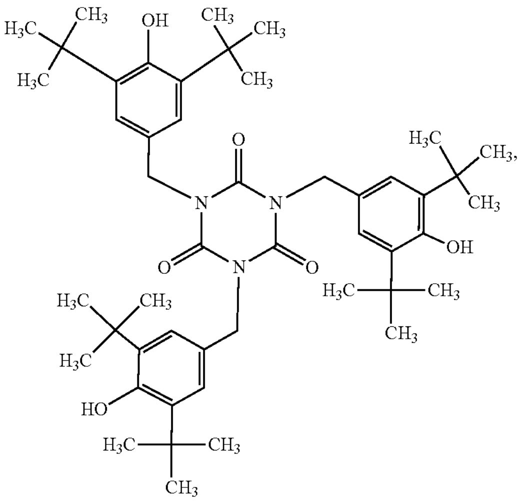

has a melting range of 218-223° C. and is for example contained in Irganox 3114 (TM, commercially available from BASF SE). It functions as a long-term heat stabilizer.

Bis[3,3-bis(4'-hydroxy-3'-tert-butylphenyl) butanoic acid] glycol ester (alternative name: 2-[3,3-bis(3-tert-butyl-4-hydroxy-phenyl)butanoyloxy]ethyl 3,3-bis(3-tert-butyl-4-hydroxy-phenyl)butan-oate) (CAS-No. 32509-66-3) [=(i-11)] is depicted below

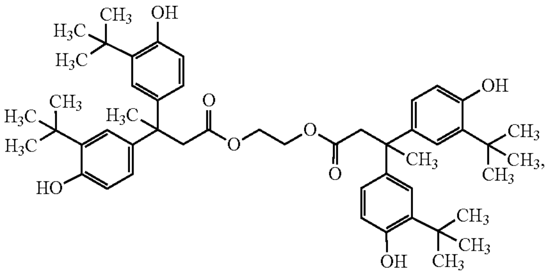 [SMILES: CC(C)(C)c1cc(C(C)(CC(=O)OCCOC(=O)CC(C)(c2ccc(O)c(C(C)(C)C)c2)c2ccc(O)c(C(C)(C)C)c2)c2ccc(O)c(C(C)(C)C)c2)ccc1O]

has a melting range of 167-171° C. and is for example contained in Hostanox 03 (TM, commercially available from Clariant Ltd). It functions as a long-term heat stabilizer.

N,N-dioctadecylhydroxylamine (CAS-No. 123250-74-8) [=(i-12)] is depicted below

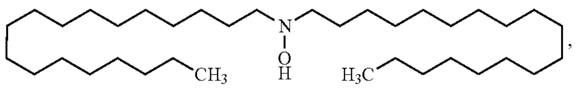

has a melting range of around 96° C. and is for example contained in Irgastab FS 042 (TM, commercially available from BASF SE). It functions as a short-term process stabilizer.

Dodecyl 3-(3-dodecoxy-3-oxo-propyl)sulfanylpropanoate (CAS-No. 123-28-4) [=(i-13)] is depicted below

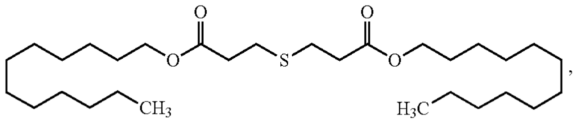 [SMILES: CCCCCCCCCCCCOC(=O)CCSCCC(=O)OCCCCCCCCCCCC]

has a melting range of 38-40° C. and is for example contained in Irganox PS 800 (TM, commercially available from BASF SE). It functions as a long-term heat stabilizer.

Octadecyl 3-(3-octadecoxy-3-oxo-propyl)sulfanylpropanoate (CAS-No. 693-36-7) [=(i-14)] is depicted below

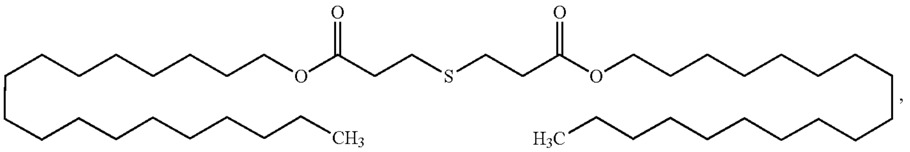 [SMILES: CCCCCCCCCCCCCCCCCCOC(=O)CCSCCC(=O)OCCCCCCCCCCCCCCCCCC]

has a melting range of 64-67° C. and is for example contained in Irganox PS 802 (TM, commercially available from BASF SE). It functions as a long-term heat stabilizer.

Pentaerythritol tetrakis[3-dodecylthio propionate (alternative name: [3-(3-dodecylsulfanylpropa-noyloxy)-2,2-bis (3-dodecylsulfanylpropanoyloxymethyl)propyl] 3-dodecylsulfanylpropanoate) (CAS-No. 29598-76-3) [=(i-15)] is depicted below

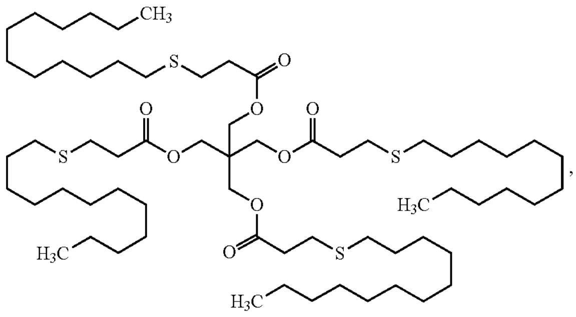 [SMILES: CCCCCCCCCCCCSCCC(=O)OCC(COC(=O)CCSCCCCCCCCCCCC)(COC(=O)CCSCCCCCCCCCCCC)COC(=O)CCSCCCCCCCCCCCC]

has a melting range of 46-52° C. and is for example contained in ADK STAB AO-4215 (TM, commercially available from Adeka). It functions as a long-term heat stabilizer.

Bis(2,2,6,6-tetramethyl-4-piperidyl) decanedioate (CAS-No. 52829-07-9) [=(i-16)] is depicted below

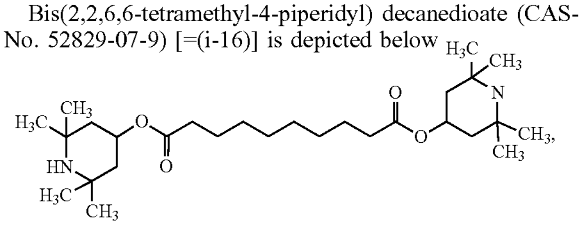

has a melting range of 81-85° C. and is for example contained in Tinuvin 770 (TM, commercially available from BASF SE). It functions as a UV light stabilizer.

(2-Hydroxy-4-octoxy-phenyl)-phenyl-methanone (CAS-No. 1843-05-6) [=(i-17)] is depicted below

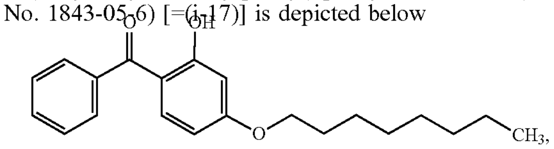

has a melting range of around 48° C. and is for example contained in Chimassorb 81 (TM, commercially available from BASF SE). It functions as a UV light stabilizer.

2-Tert-butyl-6-(5-chlorobenzotriazol-2-yl)-4-methyl-phenol (CAS-No. 3896-11-5) [=(i-18)] is depicted below

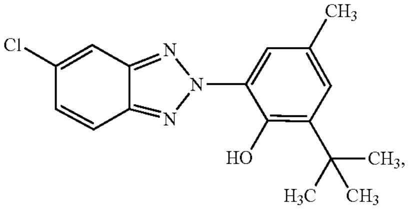 [SMILES: Cc1cc(-n2nc3ccc(Cl)cc3n2)c(O)c(C(C)(C)C)c1]

has a melting range of 137-140° C. and is for example contained in Tinuvin 326 (TM, commercially available from BASF SE). It functions as a UV light stabilizer.

2-(4,6-Diphenyl-1,3,5-triazin-2-yl)-5-hexoxy-phenol (CAS-No. 147315-50-2) [=(i-19)] is depicted below

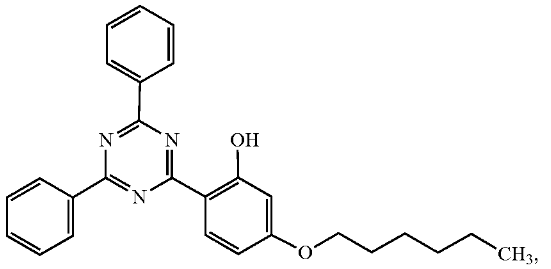 [SMILES: CCCCCCOc1ccc(-c2nc(-c3ccccc3)nc(-c3ccccc3)n2)c(O)c1]

has a melting range of around 149° C. and is for example contained in Tinuvin 1577 (TM, commercially available from BASF SE). It functions as a UV light stabilizer. 2-[4,6-Bis(4-phenylphenyl)-1,3,5-triazin-2-yl]-5-(2-ethylhexoxy)phenol (CAS-No. 204583-39-1) [=(i-20)] is depicted below

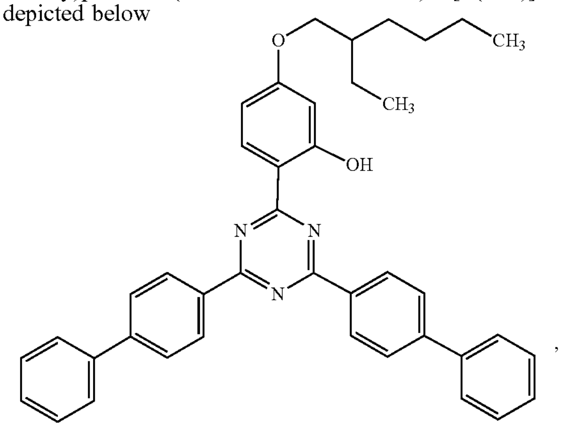

has a melting range of 120-130° C. and is for example contained in Tinuvin 1600 (TM, commercially available from BASF SE). It functions as a UV light stabilizer.

2-[4,6-Bis(2,4-dimethylphenyl)-1,3,5-triazin-2-yl]-5-[3-(2-ethylhexoxy)-2-hydroxy-propoxy]phenol (CAS-No. 137658-79-8) [=(i-21)] is depicted below

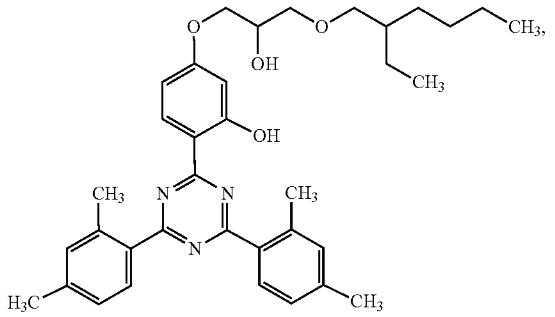 [SMILES: CCCCC(CC)COCC(O)COc1ccc(-c2nc(-c3ccc(C)cc3C)nc(-c3ccc(C)cc3C)n2)c(O)c1]

has a melting range of 75-77° C. and is for example contained in Tinuvin 405 (TM, commercially available from BASF SE). It functions as a UV light stabilizer.

Butanedioic acid, 1,4-dimethyl ester, polymer with 4-hydroxy-2,2,6,6-tetramethyl-1-piperidineethanol (CAS-No. 65447-77-0) [=i-22)], which starting monomers are depicted below

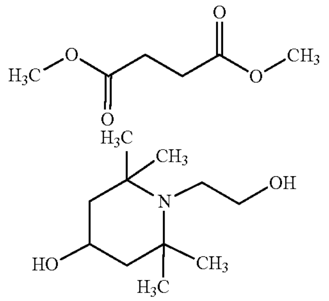

and which repeating units are depicted below

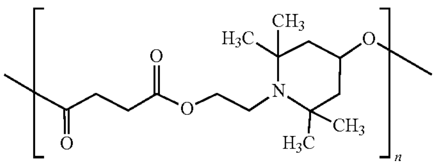

-continued

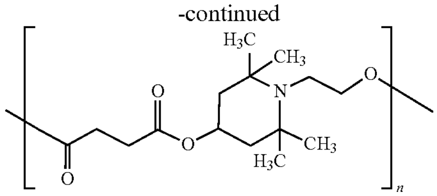

, has a melting range of 50-135° C. and is for example contained in Tinuvin 622 (TM, commercially available from BASF SE). It functions as a UV light stabilizer.

N,N',N'',N'''-Tetrakis-(2,4-bis[N-(1-cyclohexyloxy-2,2,6,6-tetramethylpiperidin-4-yl)-butylamino]-1,3,5-triazin-6-yl)-1,5,8,12-tetrazadodecane (alternative name: N6-[3-[[4,6-Bis[butyl-[1-(cyclo-hexoxy)-2,2,6,6-tetramethyl-4-piperidyl]amino]-1,3,5-triazin-2-yl]-[2-[[4,6-bis[butyl-[1-(cyclo-hexoxy)-2,2,6,6-tetramethyl-4-piperidyl]amino]-1,3,5-triazin-2-yl]-[3-[[4,6-bis[butyl-[1-(cyclo-hexoxy)-2,2,6,6-tetramethyl-4-piperidyl]amino]-1,3,5-triazin-2-yl]amino]-propyl]-amino]ethyl]amino]propyl]-N2,N4-dibutyl-N2,N4-bis[1-(cyclohexoxy)-2,2,6,6-tetramethyl-4-piperidyl]-1,3,5-triazine-2,4,6-triamine) (CAS-No. 122587-07-9) [=(i-23)] is depicted below

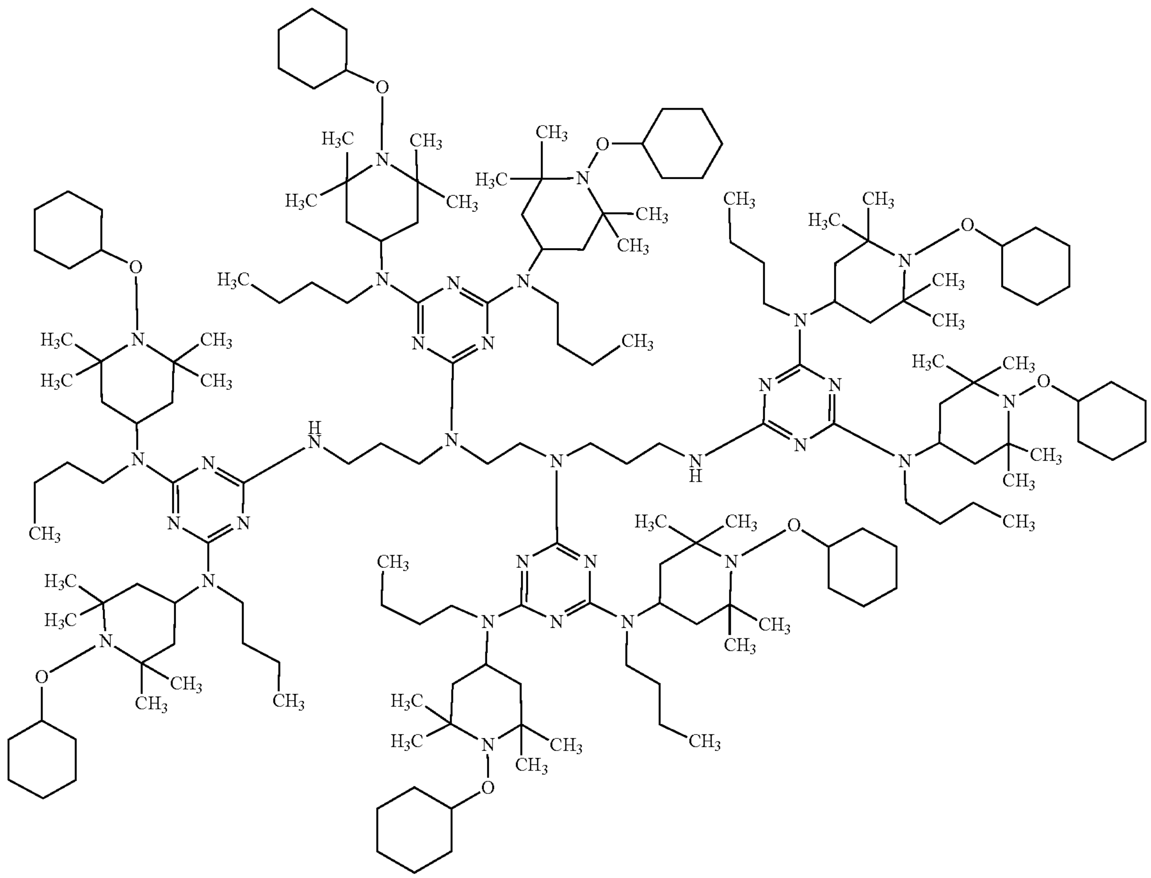

, has a melting range of 113-121° C. It is for example obtainable according to example 68 of EP 0309402. It functions as a UV light stabilizer.

N,N',N'',N'''-Tetrakis-(2,4-bis[N-(1,2,2,6,6-pentamethylpiperidin-4-yl)-butylamino]-1,3,5-triazin-6-yl)-1,5,8,12-tetrazadodecane (alternative name 1: 1,3,5-triazine-2,4,6-triamine, N,N'''-1,2-ethanediylbis[N[3-[[4,6-bis[butyl(1,2,2,6,6-pentamethyl-4-piperidinyl)amino]-1,3,5-triazin-2-yl]amino]propyl]-N',N''-bis(1,2,2,6,6-pentamethyl-4-piperidinyl)-; alternative name 2: N6-[3-[[4,6-bis[butyl-(1-hydroxy-2,2,6,6-tetramethyl-4-piperidyl)amino]-1,3,5-triazin-2-yl]-[2-[[4,6-bis[butyl-(1-hydroxy-2,2,6,6-tetramethyl-4-piperidyl)amino]-1,3,5-triazin-2-yl]-[3-[[4,6-bis[butyl-(1-hydroxy-2,2,6,6-tetramethyl-4-piperidyl)amino]-1,3,5-triazin-2-yl]amino]propyl]amino]ethyl]amino]propyl]-N2,N4-dibutyl-N2,N4-bis(1-hydroxy-2,2,6,6-tetramethyl-4-piperidyl)-1,3,5-triazine-2,4,6-triamine) (CAS-No. 106990-43-6) p (i-24)) is depicted below

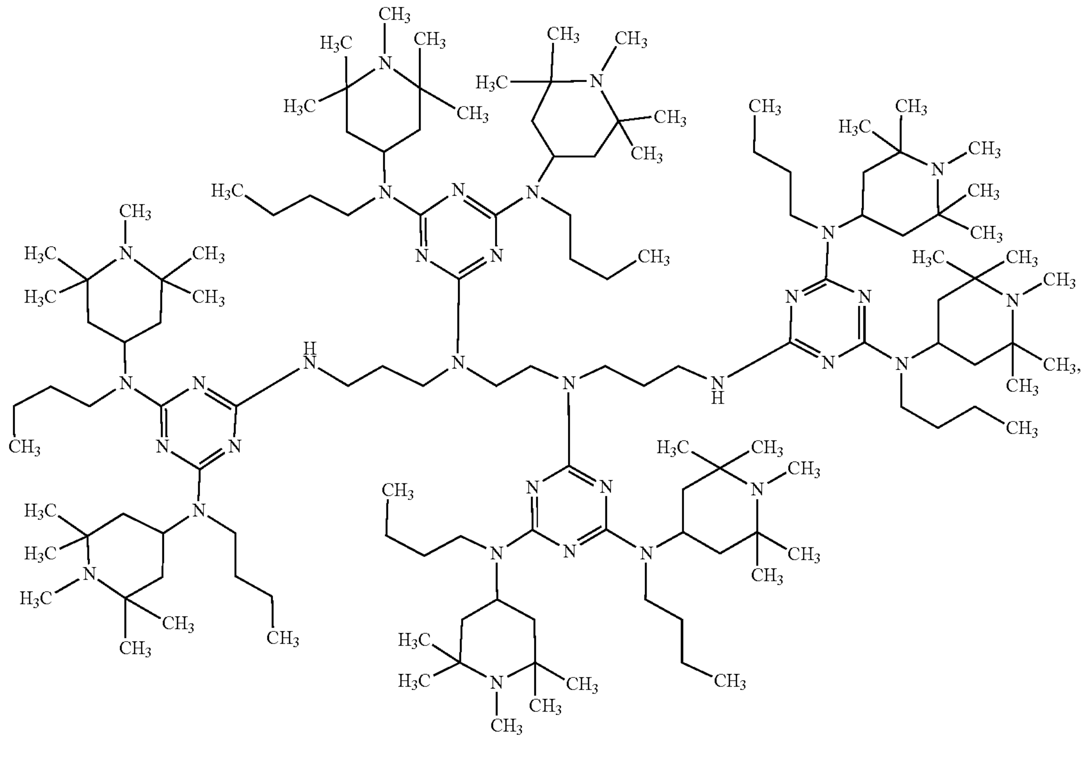

has a melting range of 115-150° C. and is for example contained in Sabostab UV 119 (TM, commercially available from Sabo). It functions as a UV light stabilizer.

N,N'-Bis-(2,4-bis[N-(1-propoxy-2,2,6,6-tetramethylpiperidin-4-yl)-butylamino]-1,3,5-triazin-6-yl)-N,N'-bis[N-(1-propoxy-2,2,6,6-tetramethylpiperidin-4-yl)]-1,8-diazaoctane (alternative name: N4-[6-[[4,6-Bis[butyl-(2,2,6,6-tetramethyl-1-propoxy-4-piperidyl)amino]-1,3,5-triazin-2-yl]-(2,2,6,6-tetramethyl-1-propoxy-4-piperidyl)amino]hexyl]-N2,N6-dibutyl-N2,N4,N6-tris(2,2,6,6-tetramethyl-1-propoxy-4-piperidyl)-1,3,5-triazine-2,4,6-triamine) (CAS-No. 1271737-36-0) [=(i-25)] has a melting range of 139-143° C. and is obtainable according to example 2 of WO 2011/029744. It functions as a UV light stabilizer.

Poly[[6-[butyl(2,2,6,6-tetramethyl-4-piperidinyl)amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]], α-[[6-[[4,6-bis(dibutylamino)-1,3,5-triazin-2-yl](2,2,6,6-tetramethyl-4-piperidinyl)amino]hexyl](2,2,6,6-tetramethyl-4-piperidinyl)amino]-ω-[4,6-bis(dibutylamino)-1,3,5-triazin-2-yl]-(CAS-No. 195300-91-5) [=(i-26)] has a melting range of 120-150° C. and is obtainable according to example 10 of EP 0782994 A. It functions as a UV light stabilizer.

Poly[[6-[butyl(2,2,6,6-tetramethyl-1-propoxy-4-piperidinyl)amino]-1,3,5-triazine-2,4-diyl][(2,2,6,6-tetramethyl-1-propoxy-4-piperidinyl)imino]-1,6-hexanediyl[(2,2,6,6-tetramethyl-1-propoxy-4-piperidinyl)imino]], α-[[6-[[4,6-bis(dibutylamino)-1,3,5-triazin-2-yl](2,2,6,6-tetramethyl-1-propoxy-4-piperidinyl)amino]hexyl](2,2,6,6-tetramethyl-1-propoxy-4-piperidinyl)amino]-ω-[4,6-bis(dibutylamino)-1,3,5-triazin-2-yl]-(CAS-No. 297748-93-7) [=(i-27)] has a melting range of 91-104° C. and is for example obtainable according to WO 2008/003605 with its preparations of compound of its formula (I). It functions as a UV light stabilizer.

Poly[[6-[(1,1,3,3-tetramethylbutyl)amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]] (CAS-No. 71878-19-8) [=(i-28)] is depicted below

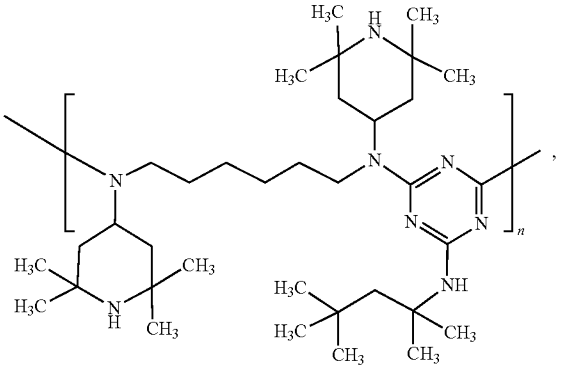

has a melting range of 100-135° C. and is for example contained in Chimassorb 944 (TM, commercially available from BASF SE). It functions as a UV light stabilizer.

Tetrakis(1,2,2,6,6-pentamethyl-4-piperidyl) butane-1,2,3,4-tetracarboxylate (alternative name: 1,2,3,4-Butanetetracarboxylic acid, tetrakis(1,2,2,6,6-pentamethyl4-piperidinyl) ester) (CAS-No. 91788-83-9) [=(i-29)] is depicted below

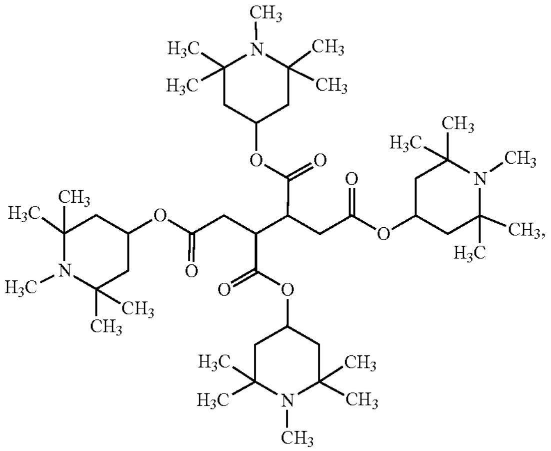 [SMILES: CN1C(C)(C)CC(OC(=O)CC(C(=O)OC2CC(C)(C)N(C)C(C)(C)C2)C(CC(=O)OC2CC(C)(C)N(C)C(C)(C)C2)C(=O)OC2CC(C)(C)N(C)C(C)(C)C2)CC1(C)C]

Has a melting range of larger than 65° C. and is for example contained in ADK STAB LA-52 (TM, commercially available from Adeka). It functions as a UV light stabilizer.

Preferred is a method for manufacturing a tablet, wherein the first polymer stabilizer is (i-1) tris(2,4-ditert-butylphenyl) phosphite (CAS-No. 31570-04-4), (i-4) tetrakis-[3-(3,5-ditert-butyl-4-hydroxy-phenyl)-propionyloxymethyl]methane (CAS-No. 6683-19-8), (i-3) 3-(3,5-ditert-butyl-4-hydroxy-phenyl)-propionic acid stearyl ester (CAS-No. 2082-79-3), (i-5) 3-(3,5-ditert-butyl-4-hydroxy-phenyl)-N-[6-[3-(3,5-ditert-butyl-4-hydroxy-phenyl)propanoylamino]hexyl]propanamide (CAS-No. 23128-74-7), (i-7) 3-(3,5-ditert-butyl-4-hydroxyphenyl)-N'-[3-(3,5-di-tert-butyl-4-hydroxyphenyl)-propanoyl]propanehydrazide (CAS-No. 32687-78-8), (i-8) 2-[2-[2-[3-(3-tert-butyl-4-hydroxy-5-methyl-phenyl)propanoyloxy]ethoxy]ethoxy]ethyl 3-(3-tert-butyl-4-hydroxy-5-methyl-phenyl)propanoate (CAS-No. 36443-68-2), (i-9) 4-[[3,5-bis[(3,5-ditert-butyl-4-hydroxy-phenyl)methyl]-2,4,6-trimethyl-phenyl]methyl]-2,6-ditert-butyl-phenol (CAS-No. 1709-70-2), (i-10) 1,3,5-tris(3,5-ditert-butyl-4-hydroxybenzyl)-1,3,5-triazine-2,4,6(1H,3H,5H)-trione (CAS-No. 27676-62-6), (i-12) N,N-dioctadecylhydroxylamine (CAS-No. 123250-74-8), (i-13)dodecyl 3-(3-dodecoxy-3-oxo-propyl)sulfanylpropanoate (CAS-No. 123-28-4), (i-14)octadecyl 3-(3-octadecoxy-3-oxo-propyl)sulfanylpropanoate (CAS-No. 693-36-7), (i-16)bis(2,2,6,6-tetramethyl-4-piperidyl) decanedioate (CAS-No. 52829-07-9), or a mixture thereof.

Preferred is a method for manufacturing a tablet, wherein the first polymer stabilizer is (i-1) tris(2,4-ditert-butylphenyl) phosphite (CAS-No. 31570-04-4), (i-4) tetrakis-[3-(3,5-ditert-butyl-4-hydroxy-phenyl)-propionyloxymethyl]methane (CAS-No. 6683-19-8), (i-3) 3-(3,5-ditert-butyl-4-hydroxy-phenyl)-propionic acid stearyl ester (CAS-No. 2082-79-3), (i-5) 3-(3,5-ditert-butyl-4-hydroxy-phenyl)-N-[6-[3-(3,5-ditert-butyl-4-hydroxy-phenyl)propanoylamino]hexyl]propanamide (CAS-No. 23128-74-7), (i-7) 3-(3,5-ditert-butyl-4-hydroxyphenyl)-N'-[3-(3,5-di-tert-butyl-4-hydroxyphenyl)-propanoyl]propanehydrazide (CAS-No. 32687-78-8), (i-8) 2-[2-[2-[3-(3-tert-butyl-4-hydroxy-5-methyl-phenyl)propanoyloxy]ethoxy]ethoxy]ethyl 3-(3-tert-butyl-4-hydroxy-5-methyl-phenyl)propanoate (CAS-No. 36443-68-2), (i-9) 4-[[3,5-bis[(3,5-ditert-butyl-4-hydroxy-phenyl)methyl]-2,4,6-trimethyl-phenyl]methyl]-2,6-ditert-butyl-phenol (CAS-No. 1709-70-2), (i-10) 1,3,5-tris(3,5-ditert-butyl-4-hydroxybenzyl)-1,3,5-triazine-2,4,6(1H,3H,5H)-trione (CAS-No. 27676-62-6), (i-12) N,N-dioctadecylhydroxylamine (CAS-No. 123250-74-8), (i-14)octadecyl 3-(3-octadecoxy-3-oxo-propyl)sulfanylpropanoate (CAS-No. 693-36-7), (i-16)bis(2,2,6,6-tetramethyl-4-piperidyl) decanedioate (CAS-No. 52829-07-9), or a mixture thereof.

Preferred is a method for manufacturing a tablet, wherein the first polymer stabilizer is (i-1) tris(2,4-ditert-butylphenyl) phosphite (CAS-No. 31570-04-4), (i-4) tetrakis-[3-(3,5-di-tert-butyl-4-hydroxy-phenyl)-propionyloxymethyl]methane (CAS-No. 6683-19-8), (i-5) 3-(3,5-ditert-butyl-4-hydroxy-phenyl)-propionic acid stearyl ester (CAS-No. 2082-79-3), (i-7) 3-(3,5-ditert-butyl-4-hydroxyphenyl)-N'-[3-(3,5-di-tert-butyl-4-hydroxyphenyl)-propanoyl]propanehydrazide (CAS-No. 32687-78-8), (i-10) 1,3,5-tris(3,5-di-tert-butyl-4-hydroxybenzyl)-1,3,5-triazine-2,4,6(1H,3H,5H)-trione (CAS-No. 27676-62-6), (i-16)bis(2,2,6,6-tetramethyl-4-piperidyl) decanedioate (CAS-No. 52829-07-9), or a mixture thereof.

Preferred is a method for manufacturing a tablet, wherein the first polymer stabilizer is a short-term processing stabilizer, which is (i-1), (i-2), (i-3), (i-12) or a mixture thereof.

Preferred is a method for manufacturing a tablet, wherein the first polymer stabilizer is a long-term heat stabilizer, which is (i-4), (i-5), (i-6), (i-7), (i-8), (i-9), (i-10), (i-11), (i-13), (i-14), (i-15) or a mixture thereof.

Preferred is a method for manufacturing a tablet, wherein the first polymer stabilizer is a UV light stabilizer, which is (i-16), (i-17), (i-18), (i-19), (i-20), (i-21), (i-22), (i-23), (i-24), (i-25), (i-26), (i-27), (i-28), (i-29) or a mixture thereof.

Preferred is a method for manufacturing a tablet, wherein the first polymer stabilizer is a UV light stabilizer, which possesses a phenolic hydroxy group and is (i-17), (i-18), (i-19), (i-20), (i-21) or a mixture thereof.

Preferred is a method for manufacturing a tablet, wherein the first polymer stabilizer is a UV light stabilizer, which possesses a hindered amine and is (i-16), (i-22), (i-23), (i-24), (i-25), (i-26), (i-27), (i-28), (i-29) or a mixture thereof.

Preferred is a method for manufacturing a tablet, wherein the first polymer stabilizer is (i-1), (i-2), (i-3), (i-4), (i-5), (i-6), (i-7), (i-8), (i-9), (i-10), (i-11), (i-12), (i-13), (i-14), (i-15), (i-16), (i-17), (i-18), (i-19), (i-20), (i-21), (i-23), (i-24), (i-25), (i-29) or a mixture thereof.

Preferred is a method for manufacturing a tablet, wherein the first polymer stabilizer is (i-1), (i-2), (i-3), (i-4), (i-5), (i-6), (i-7), (i-8), (i-9), (i-10), (i-11), (i-12), (i-13), (i-14), (i-15), (i-16), (i-17), (i-18), (i-19), (i-20), (i-21), (i-22), (i-23), (i-24), (i-28), (i-29) or a mixture thereof.

Preferred is a method for manufacturing a tablet, wherein the first polymer stabilizer is (i-1), (i-2), (i-3), (i-4), (i-5), (i-6), (i-7), (i-8), (i-9), (i-10), (i-11), (i-12), (i-13), (i-14), (i-15), (i-16), (i-17), (i-18), (i-19), (i-20), (i-21), (i-23), (i-24), (i-29) or a mixture thereof.

Preferred is a method for manufacturing a tablet, wherein the further ingredient (iv) contains less than 3 wt. % of polymeric components, which are different to the first primary polymer stabilizers (i-22), (i-26), (i-27) and (i-28), based on the sum of components (i), (ii), (iii) and (iv), which is 100 wt. %. Very preferred is less than 2 wt. % of the polymer components, particularly preferred is less than 1 wt. % of the polymer components and very particularly preferred is 0 wt. % of the polymer components.

Preferred is a method for manufacturing a tablet, wherein the further ingredient (iv) contains less than 9 wt. % of a binder, which is a molecule comprising an alkyl or alkenyl group with more than 14 carbon atoms and is different to the first primary polymer stabilizers (i-5), (i-12) and (i-14) and the secondary polymer stabilizers zinc stearate, calcium stearate and magnesium stearate, based on the sum of components (i), (ii), (iii) and (iv), which is 100 wt. %. Very preferred is less than 5 wt. % of the binder, particularly preferred is less than 3 wt. % of the binder, very particularly preferred is less than 1 wt. % of the binder and especially preferred is 0 wt. % of the binder.

Preferred is a method for manufacturing a tablet, wherein the further ingredient (iv) contains less than 1 wt. % of a micro-cellulose based on the sum of components (i), (ii), (iii) and (iv), which is 100 wt. %, very preferred less than 0.1 wt. % and particularly preferred, the further ingredient (iv) is free of a micro-cellulose.

Preferred is a method for manufacturing a tablet, wherein the further ingredient (iv) contains less than 1 wt. % of a carbohydrate based on the sum of components (i), (ii), (iii) and (iv), which is 100 wt. %, very preferred less than 0.1 wt. % and particularly preferred, the further ingredient (iv) is free of a carbohydrate.

Preferred is a method for manufacturing a tablet, wherein the further ingredient (iv) contains less than 1 wt. % of $SiO_2$ based on the sum of components (i), (ii), (iii) and (iv), which is 100 wt. %, very preferred less than 0.1 wt. % and particularly preferred, the further ingredient (iv) is free of $SiO_2$.

Preferred is a method for manufacturing a tablet, wherein the further ingredient (iv) contains less than 1 wt. % of a silicon-containing substance based on the sum of components (i), (ii), (iii) and (iv), which is 100 wt. %, very preferred less than 0.1 wt. % and particularly preferred, the further ingredient (iv) is free of a silicon-containing substance.

Preferred is a method for manufacturing a tablet, wherein the further ingredient (iv) contains less than 1 wt. % of an inorganic substance based on the sum of components (i), (ii), (iii) and (iv), which is 100 wt. %, very preferred less than 0.1 wt. % and particularly preferred, the further ingredient (iv) is free of an inorganic substance.

Preferred is a method for manufacturing a tablet, wherein the further ingredient (iv) contains less than 1 wt. % of an ionic salt based on the sum of components (i), (ii), (iii) and (iv), which is 100 wt. %, very preferred less than 0.1 wt. % and particularly preferred, the further ingredient (iv) is free of an ionic salt.

Preferred is a method for manufacturing a tablet, wherein the further ingredient (iv) contains less than 1 wt. % of a colorant, which has a light absorption maxima above 430 nm, based on the sum of components (i), (ii), (iii) and (iv), which is 100 wt. %, very preferred less than 0.1 wt. % and particularly preferred, the further ingredient (iv) is free of a colorant, which has a light absorption maxima above 430 nm.

Preferred is a method for manufacturing a tablet, wherein the secondary polymer stabilizer (ii) is contained in an amount of 0 to 29 wt. % based on the sum of components (i), (ii), (iii) and (iv), which is 100 wt. %. Very preferred is an amount of 0 to 20 wt. %, particularly preferred is an amount of 0 to 15 wt. %, very particularly preferred is an amount of 0 to 10 wt. %, especially preferred is an amount of 0 to 5 wt. % and very especially preferred is an amount of 0 wt. %.

Preferred is a method for manufacturing a tablet, wherein the third polymer stabilizer (iii) is contained in an amount of 0 to 25 wt. % based on the sum of components (i), (ii), (iii) and (iv), which is 100 wt. %. Very preferred is an amount of 0 to 20 wt. %, particularly preferred is an amount of 0 to 15 wt. %, very particularly preferred is an amount of 0 to 10 wt. %, especially preferred is an amount of 0 to 5 wt. % and very especially preferred is an amount of 0 wt. %.

Preferred is a method for manufacturing a tablet, wherein the further ingredient (iv) is free of a component which is liquid at 37° C. and 101.32 KPa, which means that the melting range of the component starts below 37° C. and 101.32 KPa. Very preferred, the further ingredient (iv) is free of a component which is liquid at 40° C. and 101.32 KPa, which means that the melting range of the component starts below 40° C. Particularly preferred, the further ingredient (iv) is free of a component which is liquid at 43° C. and 101.32 KPa, which means that the melting range of the component starts below 43° C. Very particularly preferred, the component is free of a component which is liquid at 46° C. and 101.32 KPa, which means that the melting range of the component starts below 46° C.

Preferred is a method for manufacturing a tablet, wherein the further ingredient (iv) is contained in an amount of 0 to 9 wt. % based on the sum of components (i), (ii), (iii) and (iv), which is 100 wt. %. Very preferred is an amount of 0 to 7 wt. % of the further ingredient (iv), particularly preferred is an amount of 0 to 5 wt. % of the further ingredient (iv), very particularly preferred is an amount of 0 to 3 wt. % of the further ingredient (iv), especially preferred is on amount of 0 to 1 wt. % of the further ingredient (iv) and very especially preferred is 0 wt. % of the further ingredient (iv).

The cross-section dimension of the tablet is the longest distance, which is possible between two points of the tablet. For example, in case the geometric form of the tablet is a ball, the cross-section dimension of the tablet is the diameter of the ball. For example, in case the geometric form of the tablet is a cube, the cross-section dimension of the tablet is the space diagonal of the cube. For example, in case the geometric form of the tablet is a tetrahedron, the cross-section dimension of the tablet is the side length of the tetrahedron.

A given weight of a tablet allows for different cross-section dimensions dependent on the density of the tablet and on the geometric form of the tablet. A ball as the geometric form provides for a given weight the lowest cross-section dimension, whereas a cylinder with a relatively small diameter of a circle and a relatively large height, i.e. a rod-like body, allows a very large cross-section dimension. Accordingly, the specific starting material and its degree of compression provides a density of the tablet, which allows based on a specific weight different cross-section dimensions of the tablet depending on the geometric form of the tablet. However, the additional condition of a cross-section dimension in a certain range limits the possible geometric forms. The conditions for the tablet of falling into a specific weight range and of falling into a specific cross-section dimension range have both to be fulfilled independently from each other.

A tablet, which is too heavy, is difficult to dose accurately into a polymer. Preferably, the tablet has a weight above 35 mg and below 300 mg, very preferably above 55 mg and below 200 mg, particularly above 65 mg and below 170 mg and very particularly above 65 mg and below 150 mg.

A tablet, which is too large, is also difficult to dose accurately into a polymer. Preferably the tablet has a cross-section dimension above 4 mm and below 15 mm, very preferably above 5 mm and below 13 mm, particularly above 6 mm and below 12 mm, very particularly above 7 mm and below 11 mm and especially above 7 mm and below 10 mm.

Preferred is a method for manufacturing a tablet, wherein the tablet has a weight above 55 mg and below 200 mg and a cross-section dimension above 4 mm and below 15 mm.

A tablet, which has a geometric form possessing a sharp vertex or a sharp edge is more vulnerable than a tablet with a geometric form having less or no sharp vertexes or sharp edges. Preferably, the tablet has a geometric form, at which in case a corner is present, each corner possesses only angles directed to the inner side of the tablet above 90° or each corner is convexly rounded, and at which in case of an edge is present, each edge possesses only angles directed to the inner side of the tablet above 90° or each edge is convexly rounded, except in case a vertex or an edge originates from an embossed groove. Convexly rounded is herein understood as convexly rounded when looking from outer surroundings onto the tablet. Accordingly, when looking from the inside of the tablet, one would see a concave form. An embossed groove, for example a dividing groove or an embossed sign, are exempted, i.e. not taken into account. Imperfections of the tablet originating from the practical conduction the method of manufacturing the tablet, i.e. not from the intended geometric form of the tablet, are also exempted, i.e. not taken into account. A vertex or an edge with an initial angle directed to the inner side of the tablet below 90° or of 90° can be avoided by convexly rounding at the vertex or the edge to be avoided, i.e. generation of a convexly rounded new vertex or a convexly rounded new edge. A vertex or an edge with an initial angle directed to the inner side of the tablet below 90° or of 90° can be avoided by a facet at the vertex or the edge to be avoided, i.e. generation of two new vertexes or three new edges, which have only angles directed to the inner side of the tablet above 90°, by a cut. For example, a tablet which in top view is round, is in side view round, elliptic, rectangular with convexly rounded vertexes, rectangular with facetted edges or consisting out of two parallel lines of a same length as sides opposing each other and two convex curves as sides opposing each other (=biconvex). For example, a tablet, which in top view is elliptic, is in side view round, elliptic, rectangular with convexly rounded vertexes, rectangular with facetted edges or consisting out of two parallel lines of a same length as sides opposing each other and two convex curves as sides opposing each other (=biconvex). For example, a tablet, which in top view is rectangular with convexly rounded vertexes or rectangular with facetted edges, is in side view rectangular with convexly rounded vertexes or rectangular with facetted edges. A tablet, which is in top view or in side view only rectangular does not fulfill the aforementioned condition of all angles larger than 90° or convexly rounded. Very preferably, the tablet has a geometric form, at which in case a corner is present, each corner is convexly rounded, and at which in case of an edge is present, each edge is convexly rounded, except in case a vertex or an edge originates from an embossed groove. Preferably, the tablet has a geometric form, which is round in top view. Very preferably, the tablet has a geometric form, which is round in top view and is in side view round, elliptic, rectangular with convexly rounded vertexes, rectangular with facetted edges or consisting out of two parallel lines of a same length as sides opposing each other and two convex curves as sides opposing each other. Particularly, the tablet has a geometric form, which is round in top view and is in side view round, rectangular with convexly rounded vertexes, rectangular with facetted edges or consisting out of two parallel lines of a same length as sides opposing each other and two convex curves as sides opposing each other. Very particularly, the tablet has a geometric form, which is round in top view and is in side view rectangular with convexly rounded vertexes, rectangular with facetted edges or consisting out of two parallel lines of a same length as sides opposing each other and two convex curves as sides opposing each other. Especially, the tablet has a geometric form, which is round in top view and is in side view rectangular with convexly rounded vertexes or consisting out of two parallel lines of a same length as sides opposing each other and two convex curves as sides opposing each other. Very especially, the tablet has a geometric form, which is round in top view and is in side view consisting out of two parallel lines of a same length as sides opposing each other and two convex curves as sides opposing each other. Preferably, the tablet has not more than four embossed grooves, very preferably not more than three embossed grooves, particularly not more than two embossed grooves, very particularly, not more than one embossed groove and especially, the tablet is free of an embossed groove. Preferably, the tablet is free of an embossed sign.

Preferred is a method for manufacturing a tablet, wherein the tablet has a geometric form, at which in case a corner is present, each corner possesses only angles directed to the inner side of the tablet above 90° or each corner is convexly rounded, and at which in case of an edge is present, each edge possesses only angles directed to the inner side of the tablet above 90° or each edge is convexly rounded, except in case a corner or an edge originates from an embossed groove.

Preferred is a method for manufacturing a tablet, wherein the tablet has a geometric form, at which in case a corner is present, each corner each corner is convexly rounded, and at which in case of an edge is present, each edge is convexly rounded, except in case a corner or an edge originates from an embossed groove.

Preferred is a method for manufacturing a tablet, wherein the tablet has a geometric form, which is round in top view.

Preferred is a method for manufacturing a tablet, wherein the tablet has a geometric form, which is round in top view and is in side view round, elliptic, rectangular with convexly rounded vertexes, rectangular with facetted edges or consisting out of two parallel lines of a same length as sides opposing each other and two convex curves as sides opposing each other.

The geometric form of the tablet is achieved with a suitable selection of the geometric form of the punches and the die. For example, for a tablet round in top view and consisting out of two parallel lines as sides opposing each other and two convex curves as sides opposing each other (=biconvex) in side view, the first punch and the second punch are each round and concave as well as the die is round. The finishing surface of the tablet reflects a design of the punches and the die.

A tablet, which is uniform, has several advantages. For a tablet, which has a geometric form, which is round in top view, a diameter of circle (d) and a height (h) exist in addition to the cross-section dimension. The height goes along the rotational axis of the geometric form from one end to the other end and the largest circle, which is possible, is located perpendicular to the height and has its center in the rotational axis. This largest possible circle has a diameter, which is herein the diameter of circle. A ratio between the diameter of circle (d) and the height (h) is an indication for uniformity of the geometric form, which is round in top view. If the diameter of circle is reached at a circle with a center in the rotational axis at the middle of the height, an even better indication of uniformity is provided. Preferably, the ratio between the diameter of circle (d) and the height (h) for a geometric from, which is round from top view, is from 0.7 to 2.5, very preferably from 0.8 to 2.0, particularly from 0.9 to 1.6, very particularly from 0.9 to 1.3 and especially from 0.9 to 1.1. A ratio of 1 indicates for example a ball. Preferably, the ratio between the diameter of circle (d) and the height (h) for a geometric from, which is round from top view and wherein the diameter of circle is at the middle of the height, is from 0.7 to 2.5, very preferably from 0.8 to 2.0, particularly from 0.9 to 1.6, very particularly from 0.9 to 1.3 and especially preferred from 0.9 to 1.1. For example, a tablet with a geometric form, which is round in top view and has a diameter of circle of 5 mm, has with a ratio between the diameter of circle (d) and the height (h) from 0.7 to 2.5 a height from 7 mm to 2.5 mm. For example, a tablet with a geometric form, which is round in top view and has a diameter of circle of 6 mm, has with a ratio between the diameter of circle (d) and the height (h) from 0.7 to 2.5 a height from 8.6 mm to 2.4 mm.

A more uniform tablet helps to prevent breaking of the tablet or generating of fines during storage and transportation prior to dosing to a polymer. If the diameter of circle is more than two-times the height, the tablet is in danger of being less stable. If the diameter of circle is less than half of the height, then the tablet might experience capping at the step of opening the second closed cavity caused by degassing of the compacted starting material. Furthermore, if the diameter of circle is less than half of the height, then a tablet with a more elongate geometric form is obtained. A more elongate geometric form can be less favorable at a tablet-polymer mixture, wherein the polymer is present in the form of pellets. During transport of this tablet-polymer mixture, for example by pneumatic transportation prior to exposing the tablet-polymer mixture to a temperature in the range of 120 to 340° C. under mechanical stirring or by transportation of a tablet-polymer mixture in a container, which is exposed during transportation to vibrations, a tablet with a more elongated geometric form can tend to more to segregation then a tablet with a more uniform geometric form. Preferably, the tablet has a cross-section dimension similar to the pellets of a polymer to be stabilized.

The above described definitions and preferences for a method of manufacturing a tablet, for the starting material and for the tablet are described for a method of manufacturing a tablet. These definitions and preferences apply also to the further embodiments of the invention.

A further embodiment of the invention is a tablet, which is solid at 37° C. and 101.32 KPa and consists out of (i) 60 to 100 wt. % of a first polymer stabilizer, which is
 (i-1) tris(2,4-ditert-butylphenyl) phosphite (CAS-No. 31570-04-4),
 (i-2) bis(2,4-dicumylphenyl) pentaerythritol diphosphite (CAS-No. 154862-43-8),
 (i-3) bis(2,4-ditert-butylphenyl)pentaerythritol diphosphite (CAS-No. 26741-53-7),
 (i-4) tetrakis-[3-(3,5-ditert-butyl-4-hydroxy-phenyl)-propionyloxymethyl]methane (CAS-No. 6683-19-8),
 (i-5) 3-(3,5-ditert-butyl-4-hydroxy-phenyl)-propionic acid stearyl ester (CAS-No. 2082-79-3),
 (i-6) 3-(3,5-ditert-butyl-4-hydroxy-phenyl)-N-[6-[3-(3,5-ditert-butyl-4-hydroxy-phenyl)propanoylamino]hexyl]propanamide (CAS-No. 23128-74-7),
 (i-7) 3-(3,5-ditert-butyl-4-hydroxyphenyl)-N'-[3-(3,5-ditert-butyl-4-hydroxyphenyl)-propanoyl]propanehydrazide (CAS-No. 3268-78-8),
 (i-8) 2-[2-[2-[3-(3-tert-butyl-4-hydroxy-5-methyl-phenyl)propanoyloxy]ethoxy]ethoxy]ethyl 3-(3-tert-butyl-4-hydroxy-5-methyl-phenyl)propanoate (CAS-No. 36443-68-2),
 (i-9) 4-[[3,5-bis[(3,5-ditert-butyl-4-hydroxy-phenyl)methyl]-2,4,6-trimethyl-phenyl]methyl]-2,6-ditert-butyl-phenol (CAS-No. 1709-70-2),
 (i-10) 1,3,5-tris(3,5-ditert-butyl-4-hydroxybenzyl)-1,3,5-triazine-2,4,6(1H,3H,5H)-trione (CAS-No. 27676-62-6),
 (i-11)bis[3,3-bis(4'-hydroxy-3'-tert-butylphenyl) butanoic acid] glycol ester (CAS-No. 32509-66-3),
 (i-12) N,N-dioctadecylhydroxylamine (CAS-No. 123250-74-8),
 (i-13)dodecyl 3-(3-dodecoxy-3-oxo-propyl)sulfanylpropanoate (CAS-No. 123-28-4),
 (i-14)octadecyl 3-(3-octadecoxy-3-oxo-propyl)sulfanylpropanoate (CAS-No. 693-36-7),
 (i-15)pentaerythritol tetrakis[3-dodecylthio proprionate] (CAS-No. 29598-76-3), (i-16)bis(2,2,6,6-tetramethyl-4-piperidyl) decanedioate (CAS-No. 52829-07-9), (i-17)(2-hydroxy-4-octoxy-phenyl)-phenyl-methanone (CAS-No. 1843-05-6), (i-18) 2-tert-butyl-6-(5-chlorobenzotriazol-2-yl)-4-methyl-phenol (CAS-No. 3896-11-5), (i-19) 2-(4,6-diphenyl-1,3,5-triazin-2-yl)-5-hexoxy-phenol (CAS-No. 147315-50-2), (i-20) 2-[4,6-bis(4-phenylphenyl)-1,3,5-triazin-2-yl]-5-(2-ethylhexoxy)phenol (CAS-No. 204583-39-1), (i-21) 2-[4,6-bis(2,4-dimethylphenyl)-1,3,5-triazin-2-yl]-5-[3-(2-ethylhexoxy)-2-hydroxy-propoxy]phenol (CAS-No. 137658-79-8), (i-22) butanedioic acid, 1,4-dimethyl ester, polymer with 4-hydroxy-2,2,6,6-tetramethyl-1-piperidineethanol (CAS-No. 65447-77-0), (i-23) N,N',N",N"'-tetrakis-(2,4-bis[N-(1-cyclohexyloxy-2,2,6,6-tetramethylpiperidin-4-yl)-butylamino]-1,3,5-triazin-6-yl)-1,5,8,12-tetrazadodecane (CAS-No. 122587-07-9), (i-24) N, N',N",N"'-Tetrakis-(2,4-bis[N-(1-cyclohexyloxy-2,2,6,6-tetramethylpiperidin-4-yl)-butylamino]-1,3,5-triazin-6-yl)-1,5,8,12-tetrazadodecane (CAS-No. 106990-43-6), (i-25) N,N'-bis-(2,4-bis[N-(1-propoxy-2,2,6,6-tetramethylpiperidin-4-yl)-butylamino]-1,3,5-triazin-6-yl)-N,N'-bis[N-(1-propoxy-2,2,6,6-tetramethylpiperidin-4-yl)]-1,8-diazaoctane (CAS-No. 1271737-36-0), (i-26) poly[[6-[butyl(2,2,6,6-tetramethyl-4-piperidinyl) amino]-1,3,5-triazine-2,4-diyl] [(2,2,6,6-tetramethyl-4-piperidinyl)imino]-1,6-hexanediyl[(2,2,6,6-tetramethyl-4-piperidinyl)imino]], α[[6-[[4,6-bis (dibutylamino)-1,3,5-triazin-2-yl](2,2,6,6-tetramethyl-4-piperidinyl)amino]hexyl](2,2,6,6-tetramethyl-4-piperidinyl) amino]-ω-[4,6-bis (dibutylamino)-1,3,5-triazin-2-yl]-(CAS-No. 195300-91-5), (i-27) poly[[6-[butyl(2,2,6,6-tetramethyl-1-propoxy-4-piperidinyl)amino]-1,3,5-triazine-2,4-diyl][(2,2,6,6-tetramethyl-1-propoxy-4-piperidinyl)imino]-1,6-hexanediyl[(2,2,6,6-tetramethyl-1-propoxy-4-piperidinyl)imino]], α-[[6-[[4,6-bis(dibutylamino)-1,3,5-triazin-2-yl](2,2,6,6-tetramethyl-1-propoxy-4-piperidinyl)amino]hexyl](2,2,6,6-tetramethyl-1-propoxy-4-piperidinyl)amino]-ω-[4,6-bis (dibutylamino)-1,3,5-triazin-2-yl]-(CAS-No. 297748-93-7), (i-28) poly[[6-[(1,1,3,3-tetramethylbutyl)amino]-1,3,5-triazine-2,4-diyl][(2,2,6,6-tetra-methyl-4-piperidinyl)imino]-1,6-hexanediyl[(2,2,6,6-tetramethyl-4-piperidinyl) imino]] (CAS-No. 71878-19-8), (i-29)tetrakis(1,2,2,6,6-pentamethyl-4-piperidyl) butane-1,2,3,4-tetracarboxylate (CAS-No. 91788-83-9), or a mixture thereof, (ii) 0 to 40 wt. % of a second polymer stabilizer, which is zinc stearate, calcium stearate, magnesium stearate or a mixture thereof, (iii) 0 to 34 wt. % of a third polymer stabilizer, which is zinc oxide, hydrotalcite, sodium benzoate or a mixture thereof, (iv) 0 to 20 wt. % of a further ingredient, which is different to the first polymer stabilizer, the second polymer stabilizer and the third polymer stabilizer, wherein the sum of components (i), (ii), (iii) and (iv) is 100 wt. %, wherein the tablet has a weight above 20 mg and below 330 mg and a cross-section dimension above 3 mm and below 18 mm.

Preferred is a tablet, wherein the tablet has a geometric form, at which in case a corner is present, each corner possesses only angles directed to the inner side of the tablet above 90° or each corner is convexly rounded, and at which in case of an edge is present, each edge possesses only angles directed to the inner side of the tablet above 90° or each edge is convexly rounded, except in case a corner or an edge originates from an embossed groove.

Preferred is a tablet, wherein the first polymer stabilizer is (i-1) tris(2,4-ditert-butylphenyl) phosphite (CAS-No. 31570-04-4), (i-4) tetrakis-[3-(3,5-ditert-butyl-4-hydroxy-phenyl)-propionyloxymethyl]methane (CAS-No. 6683-19-8), (i-5) 3-(3,5-ditert-butyl-4-hydroxy-phenyl)-propionic acid stearyl ester (CAS-No. 2082-79-3), (i-6) 3-(3,5-ditert-butyl-4-hydroxy-phenyl)-N-[6-[3-(3,5-ditert-butyl-4-hydroxy-phenyl)propanoylamino]hexyl] propanamide (CAS-No. 23128-74-7), (i-7) 3-(3,5-ditert-butyl-4-hydroxyphenyl)-N'-[3-(3,5-ditert-butyl-4-hydroxyphenyl)-propanoyl]propanehydrazide (CAS-No. 32687-78-8), (i-8) 2-[2-[2-[3-(3-tert-butyl-4-hydroxy-5-methyl-phenyl)propanoyloxy]ethoxy]ethoxy]ethyl 3-(3-tert-butyl-4-hydroxy-5-methyl-phenyl)propanoate (CAS-No. 36443-68-2), (i-9) 4-[[3,5-bis[(3,5-ditert-butyl-4-hydroxy-phenyl) methyl]-2,4,6-trimethyl-phenyl]methyl]-2,6-ditert-butyl-phenol (CAS-No. 1709-70-2), (i-10) 1,3,5-tris(3,5-ditert-butyl-4-hydroxybenzyl)-1,3,5-triazine-2,4,6(1H,3H,5H)-trione (CAS-No. 27676-62-6), (i-12) N,N-dioctadecylhydroxylamine (CAS-No. 123250-74-8)

(i-13)dodecyl 3-(3-dodecoxy-3-oxo-propyl)sulfanylpropanoate (CAS-No. 123-28-4), (i-14)octadecyl 3-(3-octadecoxy-3-oxo-propyl)sulfanyl-propanoate (CAS-No. 693-36-7), (i-16)bis(2,2,6,6-tetramethyl-4-piperidyl) decanedioate (CAS-No. 52829-07-9), or a mixture thereof.

Preferred is a tablet, wherein the first polymer stabilizer is (i-1) tris(2,4-ditert-butylphenyl) phosphite (CAS-No. 31570-04-4), (i-4) tetrakis-[3-(3,5-di-tert-butyl-4-hydroxy-phenyl)-propionyloxymethyl]methane (CAS-No. 6683-19-8), (i-5) 3-(3,5-ditert-butyl-4-hydroxy-phenyl)-propionic acid stearyl ester (CAS-No. 2082-79-3), (i-7) 3-(3,5-ditert-butyl-4-hydroxyphenyl)-N'-[3-(3,5-ditert-butyl-4-hydroxyphenyl)-propanoyl]propanehydrazide (CAS-No. 32687-78-8), (i-10) 1,3,5-tris(3,5-di-tert-butyl-4-hydroxybenzyl)-1,3,5-triazine-2,4,6(1H,3H,5H)-trione (CAS-No. 27676-62-6), (i-16)bis(2,2,6,6-tetramethyl-4-piperidyl) decanedioate (CAS-No. 52829-07-9), or a mixture thereof.

Preferred is a tablet, wherein the further ingredient (iv) contains less than 3 wt. % of polymeric components, which are different to the first primary polymer stabilizers (i-22), (i-26), (i-27) and (i-28), based on the sum of components (i), (ii), (iii) and (iv), which is 100 wt. %.

Preferred is a tablet, wherein the further ingredient (iv) contains less than 9 wt. % of a binder, which is a molecule comprising an alkyl or alkenyl group with more than 14 carbon atoms and is different to the first primary polymer stabilizers (i-5), (i-12) and (i-14) and the secondary polymer stabilizers zinc stearate, calcium stearate and magnesium stearate, based on the sum of components (i), (ii), (iii) and (iv), which is 100 wt. %.

Preferred is a tablet, wherein the secondary polymer stabilizer (ii) is contained in an amount of 0 to 29 wt. % based on the sum of components (i), (ii), (iii) and (iv), which is 100 wt. %.

Preferred is a tablet, wherein the further ingredient (iv) is contained in an amount of 0 to 9 wt. % based on the sum of components (i), (ii), (iii) and (iv), which is 100 wt. %.

Preferred is a tablet, wherein the tablet has a weight above 55 mg and below 200 mg and a cross-section dimension above 4 mm and below 15 mm.

A further embodiment of the invention is a method for manufacturing a stabilized polymer, which comprises the steps of (AP) dosing a tablet into a polymer to obtain a tablet-polymer mixture, (BP) exposing the tablet-polymer mixture to a temperature in the range of 120 to 340° C. under mechanical stirring to obtain a stabilized polymer, wherein the polymer is a polyolefin, a polystyrene or a mixture thereof, wherein the tablet is solid at 37° C. and 101.32 KPa and consists out of (i) 60 to 100 wt. % of a first polymer stabilizer, which is (i-1) tris(2,4-ditert-butylphenyl) phosphite (CAS-No. 31570-04-4), (i-2) bis(2,4-dicumylphenyl) pentaerythritol diphosphite (CAS-No. 154862-43-8), (i-3) bis(2,4-ditert-butylphenyl)pentaerythritol diphosphite (CAS-No. 26741-53-7), (i-4) tetrakis-[3-(3,5-ditert-butyl-4-hydroxy-phenyl)-propionyloxymethyl]methane (CAS-No. 6683-19-8), (i-5) 3-(3,5-ditert-butyl-4-hydroxy-phenyl)-propionic acid stearyl ester (CAS-No. 2082-79-3), (i-6) 3-(3,5-ditert-butyl-4-hydroxy-phenyl)-N-[6-[3-(3,5-ditert-butyl-4-hydroxy-phenyl)propanoylamino]hexyl]propanamide (CAS-No. 23128-74-7), (i-7) 3-(3,5-ditert-butyl-4-hydroxyphenyl)-N'-[3-(3,5-ditert-butyl-4-hydroxyphenyl)-propanoyl]propanehydrazide (CAS-No. 3268-78-8), (i-8) 2-[2-[2-[3-(3-tert-butyl-4-hydroxy-5-methyl-phenyl)propanoyloxy]ethoxy]ethoxy]ethyl 3-(3-tert-butyl-4-hydroxy-5-methyl-phenyl)propanoate (CAS-No. 36443-68-2), (i-9) 4-[[3,5-bis[(3,5-ditert-butyl-4-hydroxy-phenyl)methyl]-2,4,6-trimethyl-phenyl]methyl]-2,6-ditert-butyl-phenol (CAS-No. 1709-70-2), (i-10) 1,3,5-tris(3,5-ditert-butyl-4-hydroxybenzyl)-1,3,5-triazine-2,4,6(1H,3H,5H)-trione (CAS-No. 27676-62-6), (i-11)bis[3,3-bis(4'-hydroxy-3'-tert-butylphenyl)butanoic acid] glycol ester (CAS-No. 32509-66-3), (i-12) N,N-dioctadecylhydroxylamine (CAS-No. 123250-74-8), (i-13)dodecyl 3-(3-dodecoxy-3-oxo-propyl)sulfanyl-propanoate (CAS-No. 123-28-4), (i-14)octadecyl 3-(3-octadecoxy-3-oxo-propyl)sulfanylpropanoate (CAS-No. 693-36-7), (i-15)pentaerythritol tetrakis[3-dodecylthio proprionate] (CAS-No. 29598-76-3), (i-16)bis(2,2,6,6-tetramethyl-4-piperidyl) decanedioate (CAS-No. 52829-07-9), (i-17)(2-hydroxy-4-octoxy-phenyl)-phenyl-methanone (CAS-No. 1843-05-6), (i-18) 2-tert-butyl-6-(5-chlorobenzotriazol-2-yl)-4-methyl-phenol (CAS-No. 3896-11-5), (i-19) 2-(4,6-diphenyl-1,3,5-triazin-2-yl)-5-hexoxy-phenol (CAS-No. 147315-50-2), (i-20) 2-[4,6-bis(4-phenylphenyl)-1,3,5-triazin-2-yl]-5-(2-ethylhexoxy)phenol (CAS-No. 204583-39-1), (i-21) 2-[4,6-bis(2,4-dimethylphenyl)-1,3,5-triazin-2-yl]-5-[3-(2-ethylhexoxy)-2-hydroxy-propoxy]phenol (CAS-No. 137658-79-8), (i-22) butanedioic acid, 1,4-dimethyl ester, polymer with 4-hydroxy-2,2,6,6-tetramethyl-1-piperidineethanol (CAS-No. 65447-77-0), (i-23) N,N',N",N"'-tetrakis-(2,4-bis[N-(1-cyclohexyloxy-2,2,6,6-tetramethylpiperidin-4-yl)-butylamino]-1,3,5-triazin-6-yl)-1,5,8,12-tetrazadodecane (CAS-No. 122587-07-9), (i-24) N, N',N",N"'-Tetrakis-(2,4-bis[N-(1-cyclohexyloxy-2,2,6,6-tetramethylpiperidin-4-yl)-butylamino]-1,3,5-triazin-6-yl)-1,5,8,12-tetrazadodecane (CAS-No. 106990-43-6), (i-25) N,N'-bis-(2,4-bis[N-(1-propoxy-2,2,6,6-tetramethylpiperidin-4-yl)-butylamino]-1,3,5-triazin-6-yl)-N,N'-bis[N-(1-propoxy-2,2,6,6-tetramethylpiperidin-4-yl)]-1,8-diazaoctane (CAS-No. 1271737-36-0), (i-26) poly[[6-[butyl(2,2,6,6-tetramethyl-4-piperidinyl)amino]-1,3,5-triazine-2,4-diyl] [(2,2,6,6-tetramethyl-4-piperidinyl)imino]-1,6-hexanediyl[(2,2,6,6-tetramethyl-4-piperidinyl)imino]], α[[6-[[4,6-bis(dibutylamino)-1,3,5-triazin-2-yl](2,2,6,6-tetramethyl-4-piperidinyl)amino]hexyl](2,2,6,6-tetramethyl-4-piperidinyl) amino]-ω-[4,6-bis(dibutylamino)-1,3,5-triazin-2-yl]-(CAS-No. 195300-91-5), (i-27) poly[[6-[butyl(2,2,6,6-tetramethyl-1-propoxy-4-piperidinyl)amino]-1,3,5-triazine-2,4-diyl][(2,2,6,6-tetramethyl-1-propoxy-4-piperidinyl)imino]-1,6-hexanediyl[(2,2,6,6-tetramethyl-1-propoxy-4-piperidinyl)imino]], α[[6-[[4,6-bis(dibutylamino)-1,3,5-triazin-2-yl](2,2,6,6-tetramethyl-1-propoxy-4-piperidinyl)amino]hexyl](2,2,6,6-tetramethyl-1-propoxy-4-piperidinyl)amino]-ω-[4,6-bis(dibutylamino)-1,3,5-triazin-2-yl]-(CAS-No. 297748-93-7), (i-28) poly[[6-[(1,1,3,3-tetramethylbutyl)amino]-1,3,5-triazine-2,4-diyl][(2,2,6,6-tetra-methyl-4-piperidinyl)imino]-1,6-hexanediyl[(2,2,6,6-tetramethyl-4-piperidinyl) imino]] (CAS-No. 71878-19-8), (i-29)tetrakis(1,2,2,6,6-pentamethyl-4-piperidyl) butane-1,2,3,4-tetracarboxylate (CAS-No. 91788-83-9), or a mixture thereof, (ii) 0 to 40 wt. % of a second polymer stabilizer, which is zinc stearate, calcium stearate, magnesium stearate or a mixture thereof, (iii) 0 to 34 wt. % of a third polymer stabilizer, which is zinc oxide, hydrotalcite, sodium benzoate or a mixture thereof, (iv) 0 to 20 wt. % of a further ingredient, which is different to the first polymer stabilizer, the second polymer stabilizer and the third polymer stabilizer, wherein the sum of components (i), (ii), (iii) and (iv) is 100 wt. %, wherein the tablet has a weight above 20 mg and below 330 mg and a cross-section dimension above 3 mm and below 18 mm.

At step (AP), a bigger tablet is in principle more difficult to dose, to blend and to disperse in a polymer.

At step (BP), the tablet components are homogeneously dispensed and/or dissolved in the polymer to be stabilized under mechanical stirring. This is supported by the heat exposure of the the tablet-polymer mixture, which leads to a lowering of the viscosity of the polymer on one side and a melting of tablet components on the other side, if the respective melting range of a component is reached. Preferably, the temperature at step (BP) is in the range from 135° C. to 330° C., very preferably from 150° C. to 310° C., particularly from 180° C. to 300° C., very particularly from 190° C. to 290° C., especially from 200° C. to 280° C. and very especially from 210° C. to 260° C.

A polyolefin is for example:

1. A homopolymer of mono-olefins and di-olefins, for example polypropylene, polyisobutylene, poly-but-1-ene, poly-4-methylpent-1-ene, polyvinylcyclohexane, polyisoprene or polybutadiene, as well as polymers of cycloolefins, for instance of cyclopentene or norbornene, polyethylene, for example high density polyethylene (HDPE), medium density polyethylene (MDPE), low density polyethylene (LDPE), linear low density polyethylene (LLDPE), or a mixture thereof, for example mixtures of polypropylene with polyisobutylene, polypropylene with polyethylene (for example PP/HDPE, PP/LDPE) or mixtures of different types of polyethylene (for example LDPE/HDPE).
2. A copolymer of mono-olefins or di-olefins with each other or with other vinyl monomers, for example ethylene/propylene copolymers, propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers, for example ethylene/norbornene like COC, ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another, or mixtures with other polyolefins, for example polypropylene/ethylene-propylene copolymers, LDPE/ethylene-vinyl acetate copolymers (EVA), or LDPE/ethylene-acrylic acid copolymers (EAA).

Polyolefins of mono-olefins, preferably polyethylene and polypropylene, can be prepared by different, and especially by the following methods:

a) radical polymerisation (normally under high pressure and at elevated temperature)
b) catalytic polymerisation using a catalyst that normally contains one or more than one metal of groups 4, 5, 6 (for example chromium) or 7 of the Periodic Table. These metals usually have one or more than one ligand, typically oxides, halides, alcoholates, esters, ethers, amines, alkyls, alkenyls and/or aryls that may be either pi- or sigma-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups 1, 2 and/or 3 of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

A polystyrene is for example:

1. A homopolymer of styrene.
2. A copolymer of styrene and a co-monomer, which is for example ethylene, propylene, dienes, nitriles, acids, maleic anhydrides, maleimides, vinyl acetate, acrylic derivatives and mixtures thereof, for example styrene/butadiene, styrene/acrylonitrile, styrene/ethylene, styrene/alkyl methacrylate, styrene/butadiene/alkyl acrylate, styrene/butadiene/alkyl methacrylate, styrene/maleic anhydride, styrene/acrylonitrile/methyl acrylate, block copolymers of styrene with a co-monomer, for example styrene/butadiene/styrene, strene/isoprene/styrene, styrene/ethylene/butylene/styrene or styrene/ethylene/propylene/styrene.
3. Graft copolymers of styrene, for example styrene on polybutadiene, styrene on polybutadiene-styrene or polybutadiene-acrylonitrile copolymers, styrene and acrylonitrile on polybutadiene, styrene, acrylonitrile and methyl methacrylate on polybutadiene, styrene and maleic anhydride on polybutadiene, styrene, acrylonitrile and maleimide on polybutadiene, styrene and maleimide on polybutadiene, styrene and alkyl acrylates or methacrylates other than methyl acrylate on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers.

At a copolymer of a polyolefin, at least two different monomers are copolymerized. Preferred is a copolymer of a polyolefin, wherein the weight content of the polymerized olefinic monomer is above 50% based on the weight of all polymerized monomers. At a copolymer of a polystyrene, at least two different monomers are copolymerized or one monomer is grafted on at least a different monomer, which has been polymerized. Preferred is a copolymer of a polystyrene, wherein the weight content of polymerized or grafted styrene is above 50% based on the weight of all polymerized or grafted monomers.

Preferably, the polymer, which is a polyolefin, a polystyrene or a mixture thereof, is thermoplastic, i.e. it can be shaped into a new form at an elevated temperature, for example at a temperature in the range from 120° C. to 340° C., especially from 135° C. to 330° C.

The polymer, which is a polyolefin, a polystyrene or a mixture thereof, is susceptible to oxidative, thermal or light-induced degradation.

An amount of tablets to be dosed to the polymer, which is a polyolefin, a polystyrene or a mixture thereof, varies with the particular polymer and the desired degree of protection against oxidative, thermal or light-induced degradation. Preferably, the amount of tablets in weight percent is from 0.01 to 5 wt. % based on the weight of the polymer, very preferably from 0.02 to 3 wt. %, particularly from 0.04 to 2 wt. %, very particularly from 0.05 to 1 wt. %, especially from 0.08 to 0.8 wt. % and very especially from 0.1 to 0.4 wt. %.

Preferred is a method for manufacturing a stabilized polymer, wherein step (BP) takes place in an extruder or a co-kneader.

At step (AP), the tablets can be dosed to the polymer, which has already a polymer temperature in the range of 120 to 340° C. For example, the tablets are dosed to the polymer, which is already warmed in the extruder or co-kneader. For example, the tablets are introduced by a feeder, which is for example an extruder, into the already warm and viscous polymer to be stabilized. Accordingly, the tablet-polymer mixture has immediately the temperature of the polymer temperature in the range of 120 to 340° C. and the tablet start to disintegrate.

Preferred is a method for manufacturing a stabilized polymer, wherein the polymer to which the tablet is dosed in step (AP) has a polymer temperature in the range of 120 to 340° C.

At step (AP), the tablets can be dosed to the polymer, which has a polymer temperature below 37° C. In case the polymer is present in the form of pellets, a tablet-polymer mixture is generated, which comprises the components (a) tablets and (b) polymer pellets. Pellets of a polymer have for example the geometric form of a cylinder and are obtained for example by hot-cutting of an extruded warm polymer strand followed by cooling in a water quench. The pellets of the polymer have ideally the same weight as the tablet, the same cross-section dimension as the tablet and a geometric form, which is related to the one of the tablet. The difference between an average value for the pellets and a value for the individual pellet depends on the applied method of manufacturing polymer pellets with its resulting polydispersity value of the polymer pellets. Preferably, the polymer in step (AP) is present as pellets, wherein the pellets have an average pellet weight above 20 mg and below 330 mg and an average pellet cross-section dimension above 3 mm and below 18 mm. The difference between an average value for the pellet and the individual pellet depends on the applied method of manufacturing polymer pellets, e.g. the obtained polydispersity of polymer pellets. Very preferably, the polymer in step (AP) is present as pellets, wherein the pellets have an average pellet weight above 22 mg and below 200 mg and an average pellet cross-section dimension above 4 mm and below 15 mm. A tablet-polymer mixture obtained in step (AP), wherein the polymer is in the form of pellets, can be prepared and stored independently from step (BP) or prepared directly before step (BP).

A polymer pellet, which is too large, is also difficult to dose accurately into a polymer. Preferably the average polymer pellet has a pellet cross-section dimension above 4 mm and below 15 mm, very preferably above 5 mm and below 13 mm, particularly above 6 mm and below 12 mm, very particularly above 7 mm and below 11 mm and especially above 7 mm and below 10 mm.

Preferred is a method for manufacturing a stabilized polymer, wherein the polymer in step (AP) is present as pellets, which have an average pellet weight above 22 mg and below 200 mg and an average pellet cross-section dimension above 4 mm and below 15 mm.

Preferred is a method for manufacturing a stabilized polymer, wherein the polymer to which the tablet is dosed in step (AP) is present in the form of pellets and has a polymer temperature below 37° C.

The definitions and preferences described for a method of manufacturing a stabilized polymer or applying thereto apply also to the further embodiments of the invention.

A further embodiment of the invention is a tablet-polymer mixture comprising the components (a) a tablet, which is solid at 37° C. and 101.32 KPa and consists out of
 (i) 60 to 100 wt. % of a first polymer stabilizer, which is
  (i-1) tris(2,4-ditert-butylphenyl) phosphite (CAS-No. 31570-04-4),
  (i-2) bis(2,4-dicumylphenyl) pentaerythritol diphosphite (CAS-No. 154862-43-8),
  (i-3) bis(2,4-ditert-butylphenyl)pentaerythritol diphosphite (CAS-No. 26741-53-7),
  (i-4) tetrakis-[3-(3,5-ditert-butyl-4-hydroxy-phenyl)-propionyloxymethyl]methane (CAS-No. 6683-19-8),
  (i-5) 3-(3,5-ditert-butyl-4-hydroxy-phenyl)-propionic acid stearyl ester (CAS-No. 2082-79-3),
  (i-6) 3-(3,5-ditert-butyl-4-hydroxy-phenyl)-N-[6-[3-(3,5-ditert-butyl-4-hydroxy-phenyl)propanoylamino]hexyl]propanamide (CAS-No. 23128-74-7),
  (i-7) 3-(3,5-ditert-butyl-4-hydroxyphenyl)-N'-[3-(3,5-ditert-butyl-4-hydroxyphenyl)-propanoyl]propanehydrazide (CAS-No. 3268-78-8),
  (i-8) 2-[2-[2-[3-(3-tert-butyl-4-hydroxy-5-methyl-phenyl)propanoyloxy]ethoxy]ethoxy]ethyl 3-(3-tert-butyl-4-hydroxy-5-methyl-phenyl)propanoate (CAS-No. 36443-68-2),
  (i-9) 4-[[3,5-bis[(3,5-ditert-butyl-4-hydroxy-phenyl)methyl]-2,4,6-trimethyl-phenyl]methyl]-2,6-di-tert-butyl-phenol (CAS-No. 1709-70-2),
  (i-10) 1,3,5-tris(3,5-ditert-butyl-4-hydroxybenzyl)-1,3,5-triazine-2,4,6(1H,3H,5H)-trione (CAS-No. 27676-62-6),
  (i-11)bis[3,3-bis(4'-hydroxy-3'-tert-butylphenyl) butanoic acid] glycol ester (CAS-No. 32509-66-3),
  (i-12) N,N-dioctadecylhydroxylamine (CAS-No. 123250-74-8),
  (i-13)dodecyl 3-(3-dodecoxy-3-oxo-propyl)sulfanylpropanoate (CAS-No. 123-28-4),
  (i-14)octadecyl 3-(3-octadecoxy-3-oxo-propyl)sulfanylpropanoate (CAS-No. 693-36-7),
  (i-15)pentaerythritol tetrakis[3-dodecylthio propripionate] (CAS-No. 29598-76-3),
  (i-16)bis(2,2,6,6-tetramethyl-4-piperidyl) decanedioate (CAS-No. 52829-07-9),
  (i-17)(2-hydroxy-4-octoxy-phenyl)-phenyl-methanone (CAS-No. 1843-05-6),
  (i-18) 2-tert-butyl-6-(5-chlorobenzotriazol-2-yl)-4-methyl-phenol (CAS-No. 3896-11-5),
  (i-19) 2-(4,6-diphenyl-1,3,5-triazin-2-yl)-5-hexoxyphenol (CAS-No. 147315-50-2),
  (i-20) 2-[4,6-bis(4-phenylphenyl)-1,3,5-triazin-2-yl]-5-(2-ethylhexoxy)phenol (CAS-No. 204583-39-1),
  (i-21) 2-[4,6-bis(2,4-dimethylphenyl)-1,3,5-triazin-2-yl]-5-[3-(2-ethylhexoxy)-2-hydroxy-propoxy] phenol (CAS-No. 137658-79-8),
  (i-22) butanedioic acid, 1,4-dimethyl ester, polymer with 4-hydroxy-2,2,6,6-tetramethyl-1-piperidineethanol (CAS-No. 65447-77-0),
  (i-23) N,N',N",N'"-tetrakis-(2,4-bis[N-(1-cyclohexyloxy-2,2,6,6-tetramethylpiperidin-4-yl)-butylamino]-1,3,5-triazin-6-yl)-1,5,8,12-tetrazadodecane (CAS-No. 122587-07-9),
  (i-24) N,N',N",N'"-Tetrakis-(2,4-bis[N-(1-cyclohexyloxy-2,2,6,6-tetramethylpiperidin-4-yl)- butylamino]-1,3,5-triazin-6-yl)-1,5,8,12-tetrazadodecane (CAS-No. 106990-43-6), (i-25) N,N'-bis-(2,4-bis[N-(1-propoxy-2,2,6,6-tetramethylpiperidin-4-yl)-butylamino]-1,3,5-triazin-6-yl)-N,N'-bis[N-(1-propoxy-2,2,6,6-tetramethylpiperidin-4-yl)]-1,8-diazaoctane (CAS-No. 1271737-36-0), (i-26) poly[[6-[butyl(2,2,6,6-tetramethyl-4-piperidinyl)amino]-1,3,5-triazine-2,4-diyl] [(2,2,6,6-tetramethyl-4-piperidinyl)imino]-1,6-hexanediyl [(2,2,6,6-tetramethyl-4-piperidinyl)imino]], α[[6-[[4,6-bis(dibutylamino)-1,3,5-triazin-2-yl](2,2,6,6-tetramethyl-4-piperidinyl)amino]hexyl](2,2,6,6-tetramethyl-4-piperidinyl) amino]-ω-[4,6-bis(dibutylamino)-1,3,5-triazin-2-yl]-(CAS-No. 195300-91-5), (i-27) poly[[6-[butyl(2,2,6,6-tetramethyl-1-propoxy-4-piperidinyl)amino]-1,3,5-triazine-2,4-diyl][(2,2,6,6-tetramethyl-1-propoxy-4-piperidinyl) imino]-1,6-hexanediyl[(2,2,6,6-tetramethyl-1-propoxy-4-piperidinyl)imino]], α[[6-[[4,6-bis(dibutylamino)-1,3,5-triazin-2-yl](2,2,6,6-tetramethyl-1-propoxy-4-piperidinyl)amino] hexyl](2,2,6,6-tetramethyl-1-propoxy-4-piperidinyl)amino]-ω-[4,6-bis(dibutylamino)-1,3,5-triazin-2-yl]-(CAS-No. 297748-93-7), (i-28) poly[[6-[(1,1,3,3-tetramethylbutyl)amino]-1,3,5-triazine-2,4-diyl][(2,2,6,6-tetra-methyl-4-piperidinyl)imino]-1,6-hexanediyl[(2,2,6,6-tetramethyl-4-piperidinyl) imino]] (CAS-No. 71878-19-8), (i-29)tetrakis(1,2,2,6,6-pentamethyl-4-piperidyl) butane-1,2,3,4-tetracarboxylate (CAS-No. 91788-83-9), or a mixture thereof, (ii) 0 to 40 wt. % of a second polymer stabilizer, which is zinc stearate, calcium stearate, magnesium stearate or a mixture thereof, (iii) 0 to 34 wt. % of a third polymer stabilizer, which is zinc oxide, hydrotalcite, sodium benzoate or a mixture thereof, (iv) 0 to 20 wt. % of a further ingredient, which is different to the first polymer stabilizer, the second polymer stabilizer and the third polymer stabilizer, wherein the sum of components (i), (ii), (iii) and (iv) is 100 wt. %, wherein the tablet has a weight above 20 mg and below 330 mg and a cross-section dimension above 3 mm and below 18 mm, and (b) a polymer, which is a polyolefin, a polystyrene or a mixture thereof, wherein the polymer is in the form of pellets and the pellets have an average pellet weight above 20 mg and below 330 mg and an average pellet cross-section dimension above 3 mm and below 18 mm, and wherein component (a) is contained in an amount from 0.01 wt. % to 5 wt. % based on the the amount of component (b).

A further embodiment of the invention is the use of a tablet for a dust-free handling of its components at manufacturing of a stabilized polymer, wherein the polymer is a polyolefin, a polystyrene or a mixture thereof, wherein a tablet, which is solid at 37° C. and 101.32 KPa and consists out of (i) 60 to 100 wt. % of a first polymer stabilizer, which is (i-1) tris(2,4-ditert-butylphenyl) phosphite (CAS-No. 31570-04-4), (i-2) bis(2,4-dicumylphenyl) pentaerythritol diphosphite (CAS-No. 154862-43-8), (i-3) bis(2,4-ditert-butylphenyl)pentaerythritol diphosphite (CAS-No. 26741-53-7), (i-4) tetrakis-[3-(3,5-ditert-butyl-4-hydroxy-phenyl)-propionyloxymethyl]methane (CAS-No. 6683-19-8), (i-5) 3-(3,5-ditert-butyl-4-hydroxy-phenyl)-propionic acid stearyl ester (CAS-No. 2082-79-3), (i-6) 3-(3,5-ditert-butyl-4-hydroxy-phenyl)-N-[6-[3-(3,5-ditert-butyl-4-hydroxy-phenyl)propanoylamino] hexyl]propanamide (CAS-No. 23128-74-7), (i-7) 3-(3,5-ditert-butyl-4-hydroxyphenyl)-N'-[3-(3,5-ditert-butyl-4-hydroxyphenyl)-propanoyl]propanehydrazide (CAS-No. 3268-78-8), (i-8) 2-[2-[2-[3-(3-tert-butyl-4-hydroxy-5-methyl-phenyl)propanoyloxy]ethoxy]ethoxy]ethyl 3-(3-tert-butyl-4-hydroxy-5-methyl-phenyl)propanoate (CAS-No. 36443-68-2), (i-9) 4-[[3,5-bis[(3,5-ditert-butyl-4-hydroxy-phenyl) methyl]-2,4,6-trimethyl-phenyl]methyl]-2,6-ditert-butyl-phenol (CAS-No. 1709-70-2), (i-10) 1,3,5-tris(3,5-ditert-butyl-4-hydroxybenzyl)-1,3,5-triazine-2,4,6(1H,3H,5H)-trione (CAS-No. 27676-62-6), (i-11) bis[3,3-bis(4'-hydroxy-3'-tert-butylphenyl) butanoic acid] glycol ester (CAS-No. 32509-66-3), (i-12) N,N-dioctadecylhydroxylamine (CAS-No. 123250-74-8), (i-13) dodecyl 3-(3-dodecoxy-3-oxo-propyl)sulfanylpropanoate (CAS-No. 123-28-4), (i-14) octadecyl 3-(3-octadecoxy-3-oxo-propyl)sulfanylpropanoate (CAS-No. 693-36-7), (i-15) pentaerythritol tetrakis[3-dodecylthio proprionate] (CAS-No. 29598-76-3), (i-16) bis(2,2,6,6-tetramethyl-4-piperidyl) decanedioate (CAS-No. 52829-07-9), (i-17) (2-hydroxy-4-octoxy-phenyl)-phenyl-methanone (CAS-No. 1843-05-6), (i-18) 2-tert-butyl-6-(5-chlorobenzotriazol-2-yl)-4-methyl-phenol (CAS-No. 3896-11-5), (i-19) 2-(4,6-diphenyl-1,3,5-triazin-2-yl)-5-hexoxy-phenol (CAS-No. 147315-50-2), (i-20) 2-[4,6-bis(4-phenylphenyl)-1,3,5-triazin-2-yl]-5-(2-ethylhexoxy)phenol (CAS-No. 204583-39-1), (i-21) 2-[4,6-bis(2,4-dimethylphenyl)-1,3,5-triazin-2-yl]-5-[3-(2-ethylhexoxy)-2-hydroxy-propoxy]phenol (CAS-No. 137658-79-8), (i-22) butanedioic acid, 1,4-dimethyl ester, polymer with 4-hydroxy-2,2,6,6-tetramethyl-1-piperidineethanol (CAS-No. 65447-77-0), (i-23) N,N',N'',N'''-tetrakis-(2,4-bis[N-(1-cyclohexyloxy-2,2,6,6-tetramethylpiperidin-4-yl)-butylamino]-1,3,5-triazin-6-yl)-1,5,8,12-tetrazadodecane (CAS-No. 122587-07-9), (i-24) N,N',N'',N'''-Tetrakis-(2,4-bis[N-(1-cyclohexyloxy-2,2,6,6-tetramethylpiperidin-4-yl)-butylamino]-1,3,5-triazin-6-yl)-1,5,8,12-tetrazadodecane (CAS-No. 106990-43-6), (i-25) N,N'-bis-(2,4-bis[N-(1-propoxy-2,2,6,6-tetramethylpiperidin-4-yl)-butylamino]-1,3,5-triazin-6-yl)-N,N'-bis[N-(1-propoxy-2,2,6,6-tetramethylpiperidin-4-yl)]-1,8-diazaoctane (CAS-No. 1271737-36-0), (i-26) poly[[6-[butyl(2,2,6,6-tetramethyl-4-piperidinyl) amino]-1,3,5-triazine-2,4-diyl] [(2,2,6,6-tetramethyl-4-piperidinyl)imino]-1,6-hexanediyl[(2,2,6,6-tetramethyl-4-piperidinyl)imino]], α[[6-[[4,6-bis (dibutylamino)-1,3,5-triazin-2-yl](2,2,6,6-tetramethyl-4-piperidinyl)amino]hexyl](2,2,6,6-tetramethyl-4-piperidinyl) amino]-ω-[4,6-bis (dibutylamino)-1,3,5-triazin-2-yl]-(CAS-No. 195300-91-5), (i-27) poly[[6-[butyl(2,2,6,6-tetramethyl-1-propoxy-4-piperidinyl)amino]-1,3,5-triazine-2,4-diyl][(2,2,6,6-tetramethyl-1-propoxy-4-piperidinyl)imino]-1,6-hexanediyl[(2,2,6,6-tetramethyl-1-propoxy-4-piperidinyl)imino]], α[[6-[[4,6-bis(dibutylamino)-1,3,5-triazin-2-yl](2,2,6,6-tetramethyl-1-propoxy-4-piperidinyl)amino]hexyl](2,2,6,6-tetramethyl-1-propoxy-4-piperidinyl)amino]-ω-[4,6-bis (dibutylamino)-1,3,5-triazin-2-yl]-(CAS-No. 297748-93-7), (i-28) poly[[6-[(1,1,3,3-tetramethylbutyl)amino]-1,3,5-triazine-2,4-diyl][(2,2,6,6-tetra-methyl-4-piperidinyl)imino]-1,6-hexanediyl[(2,2,6,6-tetramethyl-4-piperidinyl) imino]] (CAS-No. 71878-19-8), (i-29)tetrakis(1,2,2,6,6-pentamethyl-4-piperidyl) butane-1,2,3,4-tetracarboxylate (CAS-No. 91788-83-9), or a mixture thereof, (ii) 0 to 40 wt. % of a second polymer stabilizer, which is zinc stearate, calcium stearate, magnesium stearate or a mixture thereof, (iii) 0 to 34 wt. % of a third polymer stabilizer, which is zinc oxide, hydrotalcite, sodium benzoate or a mixture thereof, (iv) 0 to 20 wt. % of a further ingredient, which is different to the first polymer stabilizer, the second polymer stabilizer and the third polymer stabilizer, wherein the sum of components (i), (ii), (iii) and (iv) is 100 wt. %, wherein the tablet has a weight above 20 mg and below 330 mg and a cross-section dimension above 3 mm and below 18 mm.

BRIEF DESCRIPTION OF THE DRAWINGS

FIG. 2 is an enlarged extract from FIG. 7.

FIG. 3 is an enlarged extract from FIG. 6.

FIG. 4 is an enlarged extract from FIG. 6.

FIG. 5 is an enlarged extract from FIG. 7.

EXAMPLES

Figure 1:
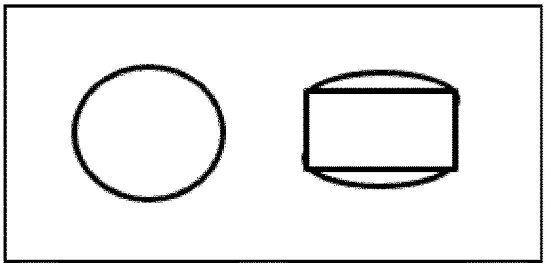
FIG. 1 shows a specific geometric form of a tablet which is round in top view (on the left) and consisting out of two parallel lines of a same length as sides opposing each other and two convex curves as sides opposing each other (=bi-convex) in side view (on the right). The two parallel lines in side view capped by the convex curves are only drawn to indicate the location of the circle shown at top view.

The following examples illustrate further the invention without limiting it. Percentage values are percentage by weight if not stated differently.

A) Methods for Characterization

Mean particle size is determined, if not otherwise stated, by a Mastersizer 2000 from the company Malvern Panalytical via a light scattering. Analysis is done based on Mie and Fraunhofer scattering model under dry dispersion pressure of 0.2 bar.

Particle size for materials, which contain particles >0.8 mm, can also be measured with a vibrating sieve shaker (e.g. Fritsch Analysette a-3 vibratory sieve shaker Model «PRO») with sieves in the range of 0.1 mm up to 4.0 mm depending on the coarse fraction of the material. Sieving time is 1 minute and sieving amplitude is 1 mm.

Bulk density is measured complying to the DIN EN ISO 17892-3.

Tablet weight (m), tablet diameter (d), tablet height (h) and side crush strength (SCS) of the same tablet are characterized with a commercially 4 in 1 tablet hardness testing equipment, i.e.

PharmaTest WHT2 from the company Pharma Test Apparatebau AG. Tensile strength (a) by diametral compression of a tablet [in MPa] is calculated according to $$\sigma=2\cdot SCS\cdot 10^6/\pi\cdot d\cdot h.$$

The Norner abrasion test is a test using a vibrating sieve shaker and glass beads to mechanically treat the tested form. An initial sieve analysis for is conducted for 1 minute followed by further sieving using glass balls on the sieve decks to mechanically impact the material and measure the change of the sieve fractions after 5, 10 and 20 minutes. Sieves selected are bottom up: 200 μm, 500 μm, 1 mm, 1.6 mm, 2.5 mm and 4 mm. The used glass balls (company Sigmund Lindner GmbH, type P) are of 16 mm±0.02 mm, weight 5.36 g/glass ball and made of soda lime glass with fine matt surface.

The test procedure is as follow:

1. The sieve shaker without glass beads is charged with 50 g of a sample and the sieving with amplitude 1 mm is conducted for 1 minute. Measuring of mass on each sieve tray and sieve pan
2. Add 8 glass balls on sieve 500 μm; 9 glass balls on sieve 1.0 mm, 10 on sieve 1.6 mm and 11 on sieve 2.5 mm. Proceed sieving for 5 minutes then measure mass on each sieve tray and sieve pan.
3. Proceed sieving for another 5 minutes, repeat weighing procedure.
4. Proceed sieving for another 10 minutes, repeat weighing procedure.

A Retsch Sieve Shaker AS 200 control from the company Retsch GmbH is used as sieve shaker.

Total fines are the sum of all material, which is collected from bottom plate, 200 μm mesh sieve and 500 μm mesh sieve. Accordingly, the fragments of a sample, which are generated under attrition stress and fall through a 500 μm mesh sieve (<500 μm), are considered fines. The particle size fraction in wt. %<500 μm after 20 minutes is the key result (Norner value) to deter-mine abrasion and impact resistance of the tested form. The range of results can vary from 0% for extremely stable to 100% for extremely unstable.

Differential scanning calorimetry (DSC) analysis is done by a constant heating rate of 20 K/min.

Melt flow index of a polymer is measured according to ISO 1133 on a Goettfert MI-Robo with the specifically stated parameters.

Yellowness index (YI) is measured according to DIN 6167 and delta E of yellowness index (YI) is measured according to DIN 6174.

B) Starting Material

SM-1: Irganox 1010

Irganox 1010 (TM, commercially available from BASF SE, melting range of 110-125° C.), which contains tetrakis-[3-(3,5-ditert-butyl-4-hydroxy-phenyl)-propionyloxym-ethyl]methane (CAS-No. 6683-19-8) as depicted below,

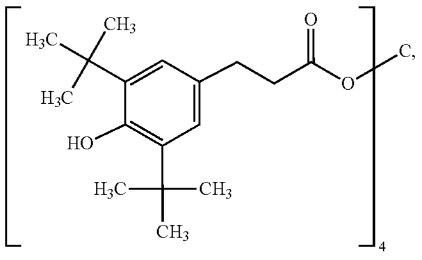

in the form of a powder, i.e. a loose bulk material with a bulk density of 643 g/L and a mean particle size of 260 μm.

SM-2: Irganox 1076

Irganox 1076 (TM, commercially available from BASF SE, melting range of 50-55° C.), which contains 3-(3,5-ditert-butyl-4-hydroxy-phenyl)-propionic acid stearyl ester (CAS-No. 2082-79-3) as depicted below

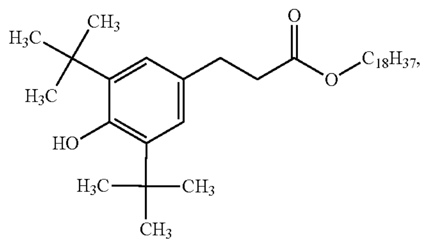

in the form of a powder, i.e. a loose bulk material with a bulk density of 520 g/L and a mean particle size of 748 μm.

SM-3: Irgafos 168

Irgafos 168 (TM, commercially available from BASF SE, melting range of 180-183° C.), which contains tris(2,4-ditert-butylphenyl) phosphite (CAS-No. 31570-04-4) as depicted below

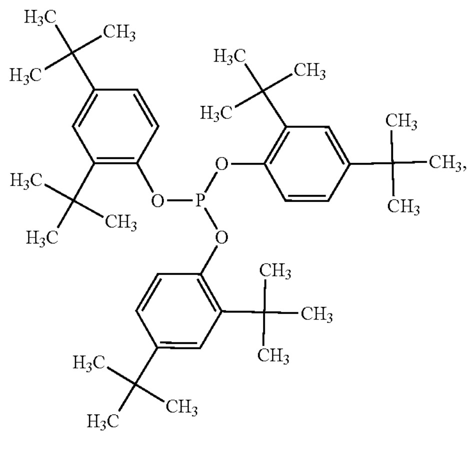 [SMILES: CC(C)(C)c1ccc(OP(Oc2ccc(C(C)(C)C)cc2C(C)(C)C)Oc2ccc(C(C)(C)C)cc2C(C)(C)C)c(C(C)(C)C)c1]

in the form of a powder, i.e. a loose bulk material with a bulk density of 467 g/L and a mean particle size of 400 μm.

SM-4: Irganox MD 1024

Irganox MD 1024 (TM, commercially available from BASF SE, melting range of 221-232° C.), which contains 3-(3,5-ditert-butyl-4-hydroxyphenyl)-N'-[3-(3,5-ditert-butyl-4-hydroxyphenyl)propanoyl]propanehydrazide (CAS-No. 32687-78-8) as depicted below

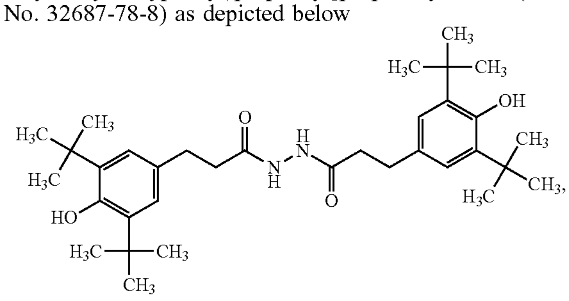

in the form of a powder, i.e. a loose bulk material with a bulk density of 384 g/L and a mean particle size of 46 μm.

SM-5: Irganox 3114

Irganox 3114 (TM, commercially available from BASF SE, melting range of 218-223° C.), which contains 1,3,5-tris(3,5-ditert-butyl-4-hydroxybenzyl)-1,3,5-triazine-2,4,6 (1H,3H,5H)-trione (CAS-No. 27676-62-6) as depicted below

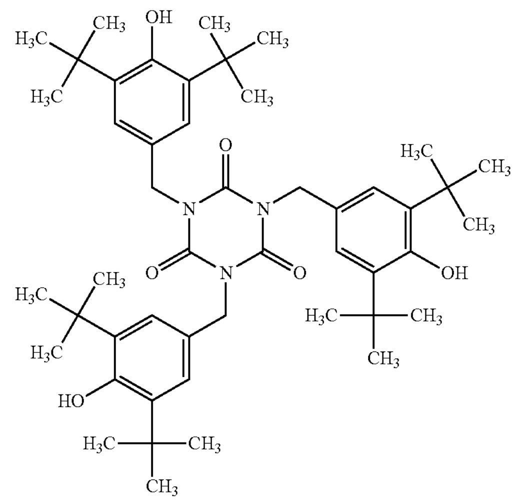 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]

in the form of a powder, i.e. a loose bulk material with a bulk density of 561 g/L and a mean particle size of 82 μm.

SM-6: Tinuvin 770

Tinuvin 770 (TM, commercially available from BASF SE, melting range of 81-85° C.), which contains bis(2,2,6,6-tetramethyl-4-piperidyl) decandioate (CAS-No. 52829-07-9) as depicted below

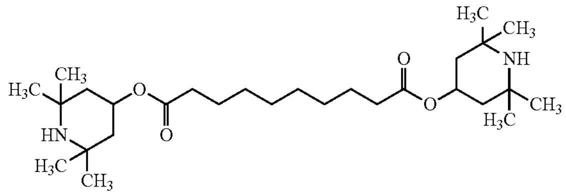

in the form of a powder, i.e. a loose bulk material with bulk density of 586 g/L and a mean particle size of 347 μm.

Sm-7: Zinc Stearate

Zinc stearate (commercially available, melting range of around 123° C., CAS-No. 557-05-1) in the form of a powder, i.e. a loose bulk material with a bulk density of 470 g/L and a mean particle size of 21 μm.

SM-8: Calcium Stearate

Calcium stearate (commercially available, melting range of 140-160° C., CAS-No. 1592-23-0) in the form of a powder, i.e. a loose bulk material with a bulk density of 521 g/L and a mean particle size of 325 μm.

SM-9: Zinc Oxide

Zinc oxide (commercially available, melting range >400° C., CAS-No. 1314-13-2) in the form of a powder, i.e. a loose bulk material with a bulk density of 880 g/L and a mean particle size of 22 μm.

SM-10: Blend of SM-1 (50) and SM-3 (50)

SM-10 is obtained in the form of a powder by blending 50 wt. % of SM-1 (Irganox 1010) and 50 wt. % of SM-3 (Irgafos 168) in a free fall or drum mixer, i.e. a drum hoop mixer from company J. Engelsmann AG, which is filled to 50% of its drum volume, at 40 rpm for 10 min at 25° C. Sample size is 250 g. The melting range of SM-10 is above 37° C. at 101.32 kPa.

In the following further starting material blends, i.e. SM-11, SM-12, SM-13, SM-14, SM-15, SM-16, SM-17, SM-18, SM-19 and SM-20 are prepared with the same method as starting material blend SM-10 differing only in compositions unless stated otherwise. The melting ranges are above 37° C. at 101.32 kPa.

SM-11: Blend of SM-3 (80) and SM-2 (20)

SM-11 is obtained in the form of a powder by blending 80 wt. % of SM-3 (Irgafos 168) and 20 wt. % of SM-2 (Irganox 1076).

SM-12: Blend of SM-1 (33) and SM-3 (67)

SM-12 is obtained in the form of a powder by blending 33 wt. % of SM-1 (Irganox 1010) and 67 wt. % of SM-3 (Irgafos 168).

SM-13: Blend of SM-1 (18.8), SM-3 (18.8) and SM-6 (62.4)

SM-13 is obtained in the form of a powder by blending 18.8 wt. % of SM-1 (Irganox 1010), 18.8 wt. % of SM-3 (Irgafos 168) and 62.4 wt. % of SM-6 (Tinuvin 770).

SM-14: Blend of SM-3 (84) and SM-4 (16)

SM-14 is obtained in the form of a powder by blending 84 wt. % of SM-3 (Irgafos 168) and 16 wt. % of SM-4 (Irganox MD 1024).

SM-15: Blend of SM-1 (50) and SM-2 (50)

SM-15 is obtained in the form of a powder by blending 50 wt. % of SM-1 (Irganox 1010) and 50 wt. % of SM-4 (Irganox 1076).

SM-16: Blend of SM-3 (78.4) and SM-5 (21.6)

SM-16 is obtained in the form of a powder by blending 78.4 wt. % of SM-3 (Irgafos 168) and 21.6 wt. % of SM-5 (Irganox 3114).

SM-17: Blend of SM-3 (67) and SM-2 (33)

SM-17 is obtained in the form of a powder by blending 67 wt. % of SM-3 (Irgafos 168) and 33 wt. % of SM-2 (Irganox 1076).

SM-18: Blend of SM-1 (24), SM-3 (48) and SM-8 (28)

SM-18 is obtained in the form of a powder by blending 24 wt. % of SM-1 (Irganox 1010), 48 wt. % of SM-3 (Irgafos 168) and 28 wt. % of SM-8 (calcium stearate).

SM-19: Blend of SM-1 (20), SM-3 (60) and SM-7 (20)

SM-19 is obtained in the form of a powder by blending 20 wt. % of SM-1 (Irganox 1010), 60 wt. % of SM-3 (Irgafos 168) and 20 wt. % of SM-7 (zinc stearate).

SM-20: Blend of SM-2 (66.7) and SM-9 (33.3)

SM-20 is obtained in the form of a powder by blending 66.7 wt. % of SM-2 (Irganox 1076) and 33.3 wt. % of SM-9 (zinc oxide).

C) Tableting of Starting Material

TA-1: Tableting of SM-1 to SM-3 and SM-10 to SM-20 on an Eccentric Tablet Press

The applied tablet press is an eccentric tablet press with one cavity for compressing (so-called single punch machine), i.e. a model XP1 from company Korsch AG. Punches of the EU D type (Euro standard) of 6 mm biplane and the respective die are installed at the model XP1. All the tableting examples of table C-1-1 with all their steps take place at room temperature between 20-25° C. No external heat energy is introduced to the starting material during tableting. The starting material as stated in table C-1-1, which has room temperature and is in a solid form, is filled into the feeding shoe of the model XP1. The open cavity formed by the die and the lower punch is filled via the feeding shoe with the starting material. A second punch closes the filled cavity. In the following compression step conducted at room temperature, the punches are moving towards each other and the compression pressure is reached. This results in formation of the tablet by compaction of the starting material in the cavity formed by the die and the two punches. The formed tablet is removed directly afterwards by removal of one punch and ejection via the other punch. The removed tablet possesses room temperature directly after removal. Applied tablet press parameters at the model XP1 for a respective starting material are stated in table C-1. The parameters of the tablets obtained at TA-1 are stated in table C-2.

TABLE C-1 tablet press parameters at TA-1

| example No. | starting material | compression pressure [MPa] | maximal position of lower punch [mm] | maximal position of upper punch [mm] | stroke rate [$min^{-1}$] |
|---|---|---|---|---|---|
| TA-1-1 [a)] | SM-1 | 455 | 5 | 4 | 15 |
| TA-1-2 [a)] | SM-2 | 209 | 7 | 5 | 15 |
| TA-1-3 [a)] | SM-3 | 440 | 7 | 5 | 15 |
| TA-1-4 [a)] | SM-10 | 385 | 9 | 5 | 15 |
| TA-1-5 [a)] | SM-11 | 440 | 9 | 5 | 15 |
| TA-1-6 [a)] | SM-12 | 331 | 9 | 5 | 15 |
| TA-1-7 [a)] | SM-13 | 442 | 6 | 4 | 15 |
| TA-1-8 [a)] | SM-14 | 99 | 9 | 5 | 15 |

TABLE C-1-continued

| tablet press parameters at TA-1 | | | | | |
|---|---|---|---|---|---|
| example No. | starting material | compression pressure [MPa] | maximal position of lower punch [mm] | maximal position of upper punch [mm] | stroke rate [$min^{-1}$] |
| TA-1-9 [a] | SM-15 | 391 | 6 | 4 | 15 |
| TA-1-10 [a] | SM-16 | 293 | 9 | 6 | 15 |
| TA-1-11 [a] | SM-17 | 432 | 9 | 6 | 15 |
| TA-1-12 [a] | SM-18 | 425 | 6 | 4 | 15 |
| TA-1-13 [a] | SM-19 | 391 | 6 | 4 | 15 |
| TA-1-14 [a] | SM-20 | 302 | 7 | 5 | 15 |

Footnotes:
[a] according to the invention

Position of punches are set manually for each SM depending on factors such as product bulk material and flow behavior while filling the die. Target is to yield a tablet with a tablet height of at least 2.5 mm.

Figure 2:
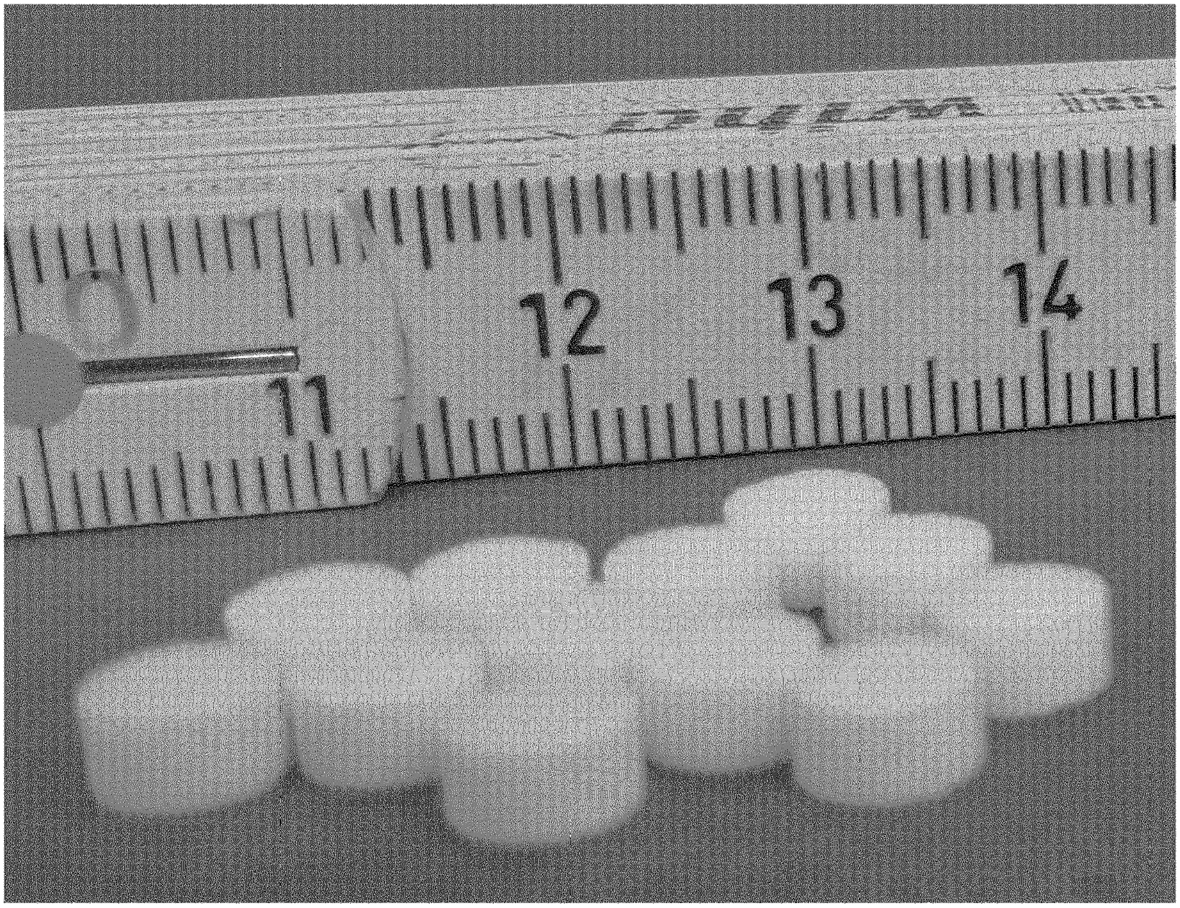
FIG. 2 shows tablets from example TA-1-2 out of starting material SM-2 with a pocket rule including a centi-/milli-meter scale in the background.
Figure 3:
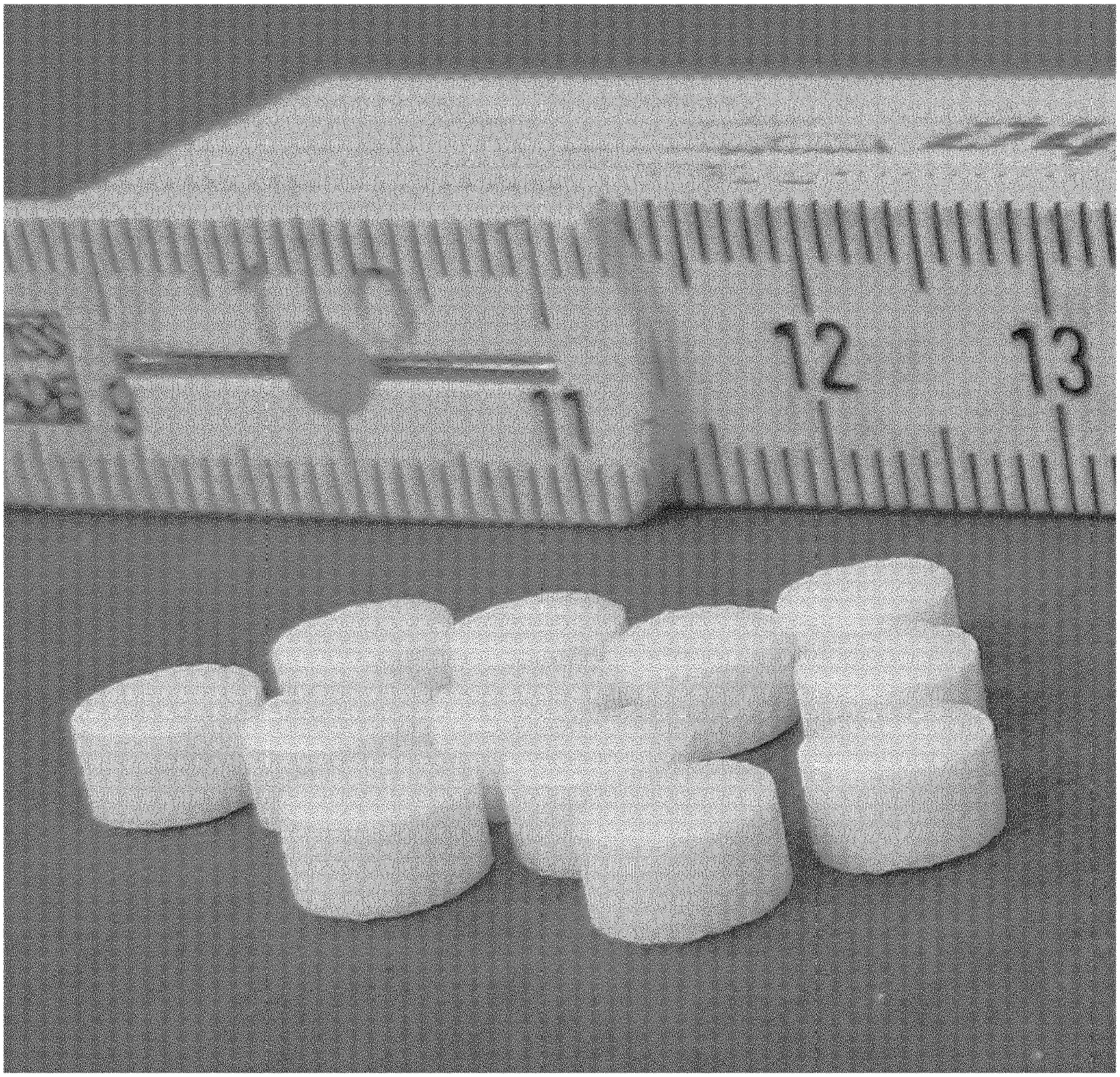
FIG. 3 shows tablets from example TA-1-3 out of starting material SM-3 with a pocket rule including a centi-/milli-meter scale in the background.

The parameters of the tablets obtained at TA-1 are stated in table C-2. Pictures of tablets from TA-1-2 and TA-1-3 are depicted in FIG. 2/FIG. 7 and FIG. 3/FIG. 6.

TABLE C-2

| parameters of tablets obtained at TA-1 | | | | | |
|---|---|---|---|---|---|
| example No. | starting material | average weight [mg] | height [mm] | tensile strength [MPa] | fines (<500 μm) after 20 min Norner test [%] |
| TA-1-1 [a] | SM-1 | 69 | 2.5 | 2.3 | 9 |
| TA-1-2 [a] | SM-2 | 86 | 3.3 | 1.2 | 1 |
| TA-1-3 [a] | SM-3 | 92 | 3.5 | 0.8 | 21 |
| TA-1-4 [a] | SM-10 | 137 | 4.9 | 1.0 | 4 |
| TA-1-5 [a] | SM-11 | 122 | 4.6 | 0.8 | 53 |
| TA-1-6 [a] | SM-12 | 136 | 4.9 | 0.8 | 9 |
| TA-1-7 [a] | SM-13 | 95 | 3.5 | 1.1 | 11 |
| TA-1-8 [a] | SM-14 | 115 | 4.7 | 0.3 | 61 |
| TA-1-9 [a] | SM-15 | 91 | 3.3 | 1.6 | 1 |
| TA-1-10 [a] | SM-16 | 139 | 5.1 | 0.9 | 20 |
| TA-1-11 [a] | SM-17 | 129 | 4.8 | 0.7 | 26 |
| TA-1-12 [a] | SM-18 | 79 | 3.1 | 0.3 | 97 |
| TA-1-13 [a] | SM-19 | 88 | 3.3 | 0.6 | 30 |
| TA-1-14 [a] | SM-20 | 112 | 3.5 | 0.8 | 19 |

Footnotes:
[a] according to the invention

D) Differential Scanning Calorimetry of a Tablet

Differential scanning calorimetry (DSC) analysis is done for determining melting behavior. The melting behavior of starting materials and tablets out of the starting materials are compared as shown in table D-1.

TABLE D-1

| melting behavior of a tablet and its starting material | | |
|---|---|---|
| example No. | sample | maxima during DSC [° C.] |
| D-1-1 [b] | SM-10 in powder form | 118.2; 179.1 |
| D-1-2 [b] | SM-10 in powder form initially heated and cooled [c] and then measured | 39 |
| D-1-3 [a] | tablet TA-1-4 out of SM-10 | 117.4; 176.8 |
| D-1-4 [b] | SM-16 in powder form | 183.7 |

TABLE D-1-continued

| melting behavior of a tablet and its starting material | | |
|---|---|---|
| example No. | sample | maxima during DSC [° C.] |
| D-1-5 [b] | SM-16 in powder form initially heated and cooled [c] and then measured | 39 |
| D-1-6 [a] | tablet TA-1-10 out of SM-16 | 180.7 |

Footnotes:
[a] according to the invention
[b] comparative
[c] initial DSC sample is exposed to a first heating with a constant heating rate of 20 K/min and cooling circle and then DSC measurement of the exposed DSC sample Table D-1 shows that there is not a significant change of melt behaviors determined by DSC for the starting materials SM-10 (blend of 50 wt. % SM-1 [Irganox 1010]) and 50 wt. % SM-3 [Irgafos 168]) and SM-16 (blend of 78.4% SM-3 [Irgafos 168] and 21.6 wt. % SM-5 [Irganox 3114]) and the tablets TA-1-4 out of SM-10 and TA-1-10 out of SM-16. If the starting materials SM-10 and SM-16 in powder form are once molten and cooled again, then only a glass transition phase at 39° C. is observed. The absence of a significant change of melt behavior at the tablets TA-1-4 and TA-1-10 indicates that there has not been an exposure to external heat energy.

E) Generation of Forms Different to a Tablet

E-1): Flakes from a Roll Compaction Process

Starting materials SM-1, SM-3 and SM-10 are press-agglomerated via a roll compaction process to obtain comparative flakes. The respective starting material in its powder form in a hop-per is force-fed via a feeding screw into a compaction zone. The compaction zone is formed by a remaining gap between two rolls with slightly scratched surfaces, which are rotating towards each other. A suitable laboratory roll compactor is for example model WP 50N/75 (roll diameter: 150 mm, roll length: 75 mm, maximum press capacity: 12.8 t, maximum linear load: 1.71 t/cm) from the company Alexanderwerk GmbH in Germany. The compacted starting material, which leaves the compaction zone as plates, is granulated via a sieve granulator to create free flowing flakes. A suitable sieve granulator is model GLA-ORV-0215 from company Frewitt Ltd from Switzerland. At this step, plates are granulated to fragments with a 4 mm mesh sieve acting as a screen. These fragments of sizes below 4 mm are further sieved into 2 categories by a 1 mm mesh sieve acting as a screen. Two sieving fractions are obtained, i.e. the desired flakes and fines. Accordingly, the fines are those fragments of sizes below 4 mm, which pass also the 1 mm mesh sieve. Depending on the initial hardness of the plates, the sieving fraction of fines amounts from 10 wt. % up to 30 wt. % of the originally fed starting material. This sieving fraction of fines needs to be roll-compacted again. During the roll compaction process, mechanical stress applied from the rolls onto the starting material is the only energy source exerted to the starting material during the compaction. No additional external heat transfer occurs during the roll compaction including the granulation with the sieve granulator. The compaction rolls are cooled to avoid material sticking to the surface. The roll compaction of SM-1, SM-3 and SM-10 takes place at atmospheric pressure with temperature ranging from 20° C. to 30° C. Table E-1 shows the obtained mean particles sizes and bulk densities.

TABLE E-1

| mean particle size and bulk density of flakes | | | |
|---|---|---|---|
| flake sample | Starting material | bulk density [g/L] | mean particle size [c] [mm] |
| E-1-1 [b] | SM-1 | 597 | 1.953 |
| E-1-2 [b] | SM-3 | 514 | 1.392 |
| E-1-3 [b] | SM-10 | 532 | 1.548 |

Footnotes:

[b] comparative

[c] mean particle size determined by a vibrating sieve shaker as decribed under A)

Figure 4:
FIG. 4 shows flakes as described at E-1) out of starting material SM-3 with a pocket rule including a centi-/milli-meter scale in the background.
Figure 6:
FIG. 6 shows tablets from example TA-1-3 (on the left) and flakes as described at E-1) (on the right) out of starting material SM-3 with a pocket rule including a centi-/milli-meter scale in the background.

A picture of flakes out of SM-3 is depicted at FIG. 4/FIG. 6. The picture at FIG. 6 shows that the flakes produced via roll compaction out of SM-3 have a less defined shape in comparison to tablets out of SM-3.

E-2): Pastilles from a Rotoform Granulation Process

For comparison, starting material SM-2 is compacted by a rotoform granulation process to obtain comparative pastilles. The starting material SM-2 comes directly from the Synthesis as a melt. The melt is treated in a scraped cooler to generate crystal seeds that are required to initiate crystallization in the rotoform granulation process. A pump delivers the molten product to the rotoform system (e.g. from IPCO former Sandvik) via heated pipes. The rotoform itself consists of a heated cylindrical stator, which is supplied with liquid product, and a perforated rotating shell that turns concentrically around the stator. Drops of the product are deposited by the nozzle bar across the whole operating width of a continuously running stainless steel belt. The rotation speed of the rotofrom is synchronized with the speed of the belt to allow a gentle deposition of the liquid droplets onto the moving belt. The belt is cooled by water sprayed underneath. The product droplets solidify or crystallize on the cooling belt and pastilles are obtained. The obtained pastilles have a diameter of around 5 mm and a height of 0.5 to 1 mm.

TABLE E-2

| mean particle size and bulk density of pastilles | | |
|---|---|---|
| pastille sample | starting material | bulk density [g/L] |
| E-2-1 [b] | SM-2 | 300 |

Footnotes:

[b] comparative

Figure 5:
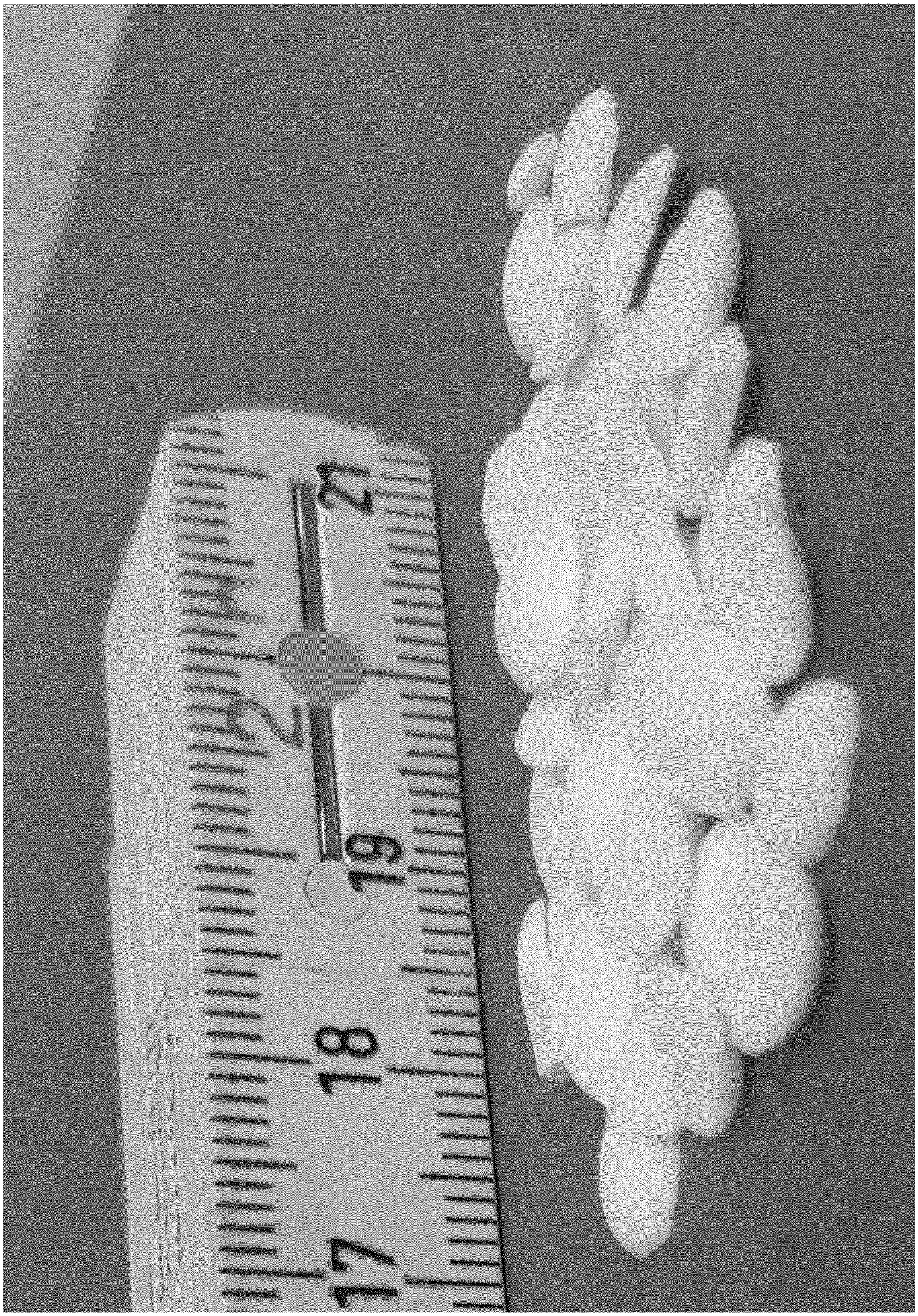
FIG. 5 shows pastilles as described at E-2) out of starting material SM-2 with a pocket rule including a centi-/milli-meter scale in the background.
Figure 7:
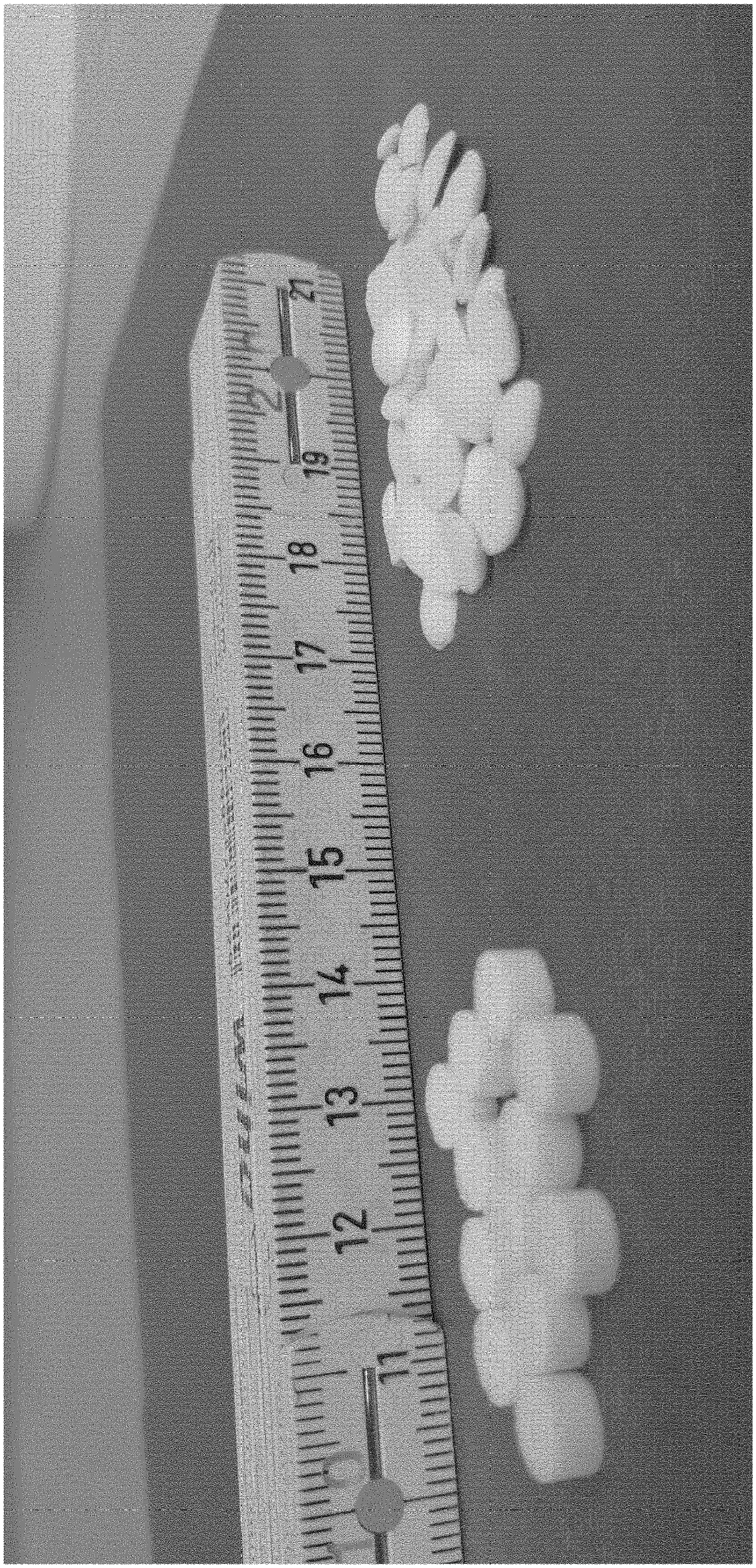
FIG. 7 shows tablets from example TA-1-2 (on the left) and pastilles as described at E-2) (on the right) out of starting material SM-2 with a pocket rule including a centi-/milli-meter scale in the background.

A picture of pastilles out of SM-2 is depicted at FIG. 5/FIG. 7. The picture at FIG. 7 shows that the pastilles out of SM-2 have a less defined shape in comparison to tablets out of SM-2.

F) Comparison for Attrition Resistance

For comparison of the attrition resistance, obtained tablets from a starting material are compared for attrition resistance to comparative flakes obtained at E-1) as shown in table F-1.

TABLE F-1

| attrition resistance of a tablet and a flake | | |
|---|---|---|
| example No. | sample | fines (<500 μm) after 20 min Norner test [%] |
| F-1-1 [a] | tablets as obtained from TA-1-1 out of SM-1 | 9 |
| F-1-2 [b] | flakes as obtained from E-1-1 out of SM-1 | 97 |
| F-1-3 [a] | tablets as obtained from TA-1-3 out of SM-3 | 21 |
| F-1-4 [b] | flakes as obtained from E-1-2 out of SM-3 | 98 |
| F-1-5 [a] | tablets as obtained from TA-1-4 out of SM-10 | 4 |
| F-1-6 [b] | flakes as obtained from E-1-3 out of SM-10 | 96 |

Footnotes:

[a] according to the invention

[b] comparative

Table F-1 shows that the starting materials SM-1, SM-3 and SM-10 in the form of a tablet are more stable towards attrition than in the form of a flake.

For comparison of the attrition resistance, obtained tablets from a starting material are compared for attrition resistance to comparative pastilles obtained at E-2 as shown in table F-2.

TABLE F-2

| attrition resistance of a tablet and a pastille | | |
|---|---|---|
| example No. | sample | fines (<500 μm) after 20 min Norner test [%] |
| F-2-1 [a] | tablets from TA-1-2 out of SM-2 | 1 |
| F-2-2 [b] | pastilles from E-2-1 out of SM-2 | 14 |

Footnotes:

[a] according to the invention

[b] comparative

Table F-2 shows that the starting material SM-2 in the form of a tablet is more stable towards attrition than in the form of a pastille.

G) Stabilization of a Linear Low-Density Polyethylene

G-1) Incorporation of Polymer Stabilizer into a Linear Low-Density Polyethylene

A blend of a linear low-density polyethylene in pellet form and a stabilizer in tablet form is compared to a blend of the linear low-density polyethylene in powder form and the stabilizer in powder form.

Linear low-density polyethylene in pellet form:

LLDPE (Dowlex SC 2108G (TM Dow Chemicals), melt flow index (230° C./2.16 kg) 2.6 g/10 min, pellet size: average diameter 3.7 mm, average height 4.0 mm; average pellet weight 33 mg)

Linear low-density polyethylene in powder form:

LLDPE (Dowlex SC 2108G (TM Dow Chemicals), pellets ground with a Pallman grinder to a powder with an average particle size as determined by a Camsizier P4: D50=1.1 mm, D90=1.9 mm)

For achieving a mixture with a weight ratio as shown in table G-1, LLDPE in pellet form is mixed with the respective tablet in a Roehnrad Elite 650 mixer at room temperature. LLDPE in powder form is blended with the stabilizer or stabilizer blend in powder form, i.e. the starting material as described at B), in a tumble mixer at room temperature.

The respective polymer stabilizer mixture as shown in table G-1 is compounded in a twin-screw extruder (Collin 25/42 L/D) at 190° C. under a nitrogen blanket and pelletized. Pellets of stabilized linear low-density polyethylene are obtained.

TABLE G-1 stabilized linear low-density polyethylene with MFI

| example No. | mixture used for obtaining stabilized linear low-density polyethylene pellets | MFI (190° C./2.16 kg) of stabilized linear low-density polyethylene pellets [g/10 min] |
|---|---|---|
| G-1-1 [b)] | 99.90% LLDPE [c)] (powder)<br>0.10% SM-10 (powder) | 2.8 |
| G-1-2 [a)] | 99.90% LLDPE (pellet)<br>0.10% TA-1-4 (tablet out of SM-10) | 2.7 |
| G-1-3 [b)] | 99.85% LLDPE (powder)<br>0.15% SM-20 (powder) | 2.7 |
| G-1-4 [a)] | 99.85% LLDPE (pellet)<br>0.15% TA-1-15 (tablet out of SM-20) | 2.6 |
| G-1-5 [b)] | 99.90% LLDPE (powder)<br>0.10% SM-19 (powder) | 2.7 |
| G-1-6 [a)] | 99.90% LLDPE (pellet)<br>0.10% TA-1-14 (tablet out of SM-19) | 2.7 |
| G-1-7 [b)] | 99.80% LLDPE (powder)<br>0.20% SM-13 (powder) | 2.6 |
| G-1-8 [a)] | 99.80% LLDPE (pellet)<br>0.20% TA-1-7 (tablet out of SM-13) | 2.7 |

Footnotes:
[a)] according to the invention
[b)] comparative
[c)] Dowlex SC 2108G from the company Dow Chemicals G-2) Performance of the Stabilized Linear Low-Density Polyethylene The melt flow properties of the obtained pellets of stabilized linear low-density polyethylene are measured at 190° C./2.16 kg (melt flow index according to ISO 1133) and the results are shown in table G-1.

Table G-1 shows that a measured melt flow index of a stabilized linear low-density polyethylene pellet obtained from the pellet-tablet blend is within the same range as the one of the stabilized linear low-density polyethylene pellets obtained from the powder-powder blend.

H) Stabilization of a Polypropylene

H-1) Incorporation of Polymer Stabilizer into a Polypropylene

A blend of a polypropylene in pellet form and a stabilizer in tablet form is compared to a blend of the polypropylene in powder form and the stabilizer in powder form.

Polypropylene in Pellet Form:

PP (HD 120 MO of the company Borealis, melt flow index (230° C./2.16 kg) 8.0 g/10 min, pellet size: average diameter 3.3 mm, average height 4.3 mm; average pellet weight 25 mg)

Polypropylene in Powder Form:

PP (HD 120 MO of the company Borealis, pellets ground with a Pallman grinder to a powder with an average particle size as determined by a Camsizier P4: D50=1.1 mm, D90=1.6 mm)

For achieving a composition with a weight ratio as shown in table H-1, PP in pellet form is mixed with the respective tablet in a Roehnrad Elite 650 mixer at room temperature. PP in powder form is blended with the stabilizer or stabilizer blend in powder form, i.e. the starting material as described at B), in a tumble mixer at room temperature.

The respective polymer stabilizer mixture as shown in table H-1 is compounded in a twin-screw extruder (Collin 25/42 L/D) at 230° C. under a nitrogen blanket and pelletized. Pellets of stabilized polypropylene are obtained.

TABLE H-1 stabilized polypropylene with MFI

| example No. | mixture used for obtaining stabilized polypropylene pellets | MFI (230° C./2.16 kg) of stabilized polypropylene pellets [g/10 min] |
|---|---|---|
| H-1-1 [b)] | 99.80% PP [c)] (powder)<br>0.20% SM-10 (powder) | 8.5 |
| H-1-2 [a)] | 99.80% PP (pellet)<br>0.20% TA-1-4 (tablet out of SM-10) | 8.7 |
| H-1-3 [b)] | 99.80% PP (powder)<br>0.20% SM-20 (powder) | 9.1 |
| H-1-4 [a)] | 99.80% PP (pellet)<br>0.20% TA-1-15 (tablet out of SM-20) | 9.1 |
| H-1-5 [b)] | 99.90% PP (powder)<br>0.10% SM-19 (powder) | 9.0 |
| H-1-6 [a)] | 99.90% PP (pellet)<br>0.10% TA-1-14 (tablet out of SM-19) | 9.1 |

Footnotes:
[a)] according to the invention
[b)] comparative
[c)] HD 120 MO from the company Borealis H-2) Performance of the Stabilized Polypropylene The melt flow properties of the obtained pellets of stabilized polypropylene are measured at 230° C./2.16 kg (melt flow index according to ISO 1133) and the results are shown in table H-1.

Table H-1 shows that a measured melt flow index of a stabilized polypropylene pellet obtained from the pellet-tablet blend is within the same range as the one of the stabilized polypropylene pellet obtained from the powder-powder blend.

I) Stabilization of an ABS Polymer

I-1) Incorporation of Polymer Stabilizer into an ABS Polymer

A blend of an ABS (acrylonitrile-butadiene-styrene) polymer in pellet form and a stabilizer in tablet form is compared to a blend of the ABS polymer in powder form and the stabilizer in powder form.

ABS Polymer in Pellet Form:

ABS polymer (Terluran GP-22 (TM of Styrolution), melt flow index of pellet (220° C./10 kg) 19.0 g/10 min, pellet size: average diameter 3.3 mm, average height 4.6 mm; average pellet weight 30 mg)

ABS Polymer in Powder Form:

ABS polymer (Terluran GP-22 (TM of Styrolution), pellets ground with a Pallman grinder to a powder with an average particle size as determined by a Camsizier P4: D50=0.7 mm, D90=1.2 mm, melt flow index of powder (220° C./10 kg) 20.5 g/10 min)

It is remarked that the grinding of the ABS polymer pellets towards a powder leads to a degradation as indicated by a melt flow index of 20.5 for the powder versus 19.0 for the pellets. A higher melt flow index indicates a lower viscosity of the heated polymer and thus for example a degradation of long polymeric chain into smaller polymeric chains.

For achieving a composition with a weight ratio as shown in table I-1, ABS polymer in pellet form is mixed with the respective tablet in a Roehnrad Elite 650 mixer at room temperature. ABS polymer in powder form is blended with the stabilizer or stabilizer blend in powder form, i.e. the starting material as described at B), in a tumble mixer at room temperature. The pellet-tablet mixture and the powder-powder mixture are dried before compounding for 3 h at 80° C. (Vacutherm 1600).

The respective polymer stabilizer mixture as shown in table I-1 is compounded in a twin-screw extruder (Collin 25/42 L/D) at 230° C. under a nitrogen blanket and pelletized. Pellets of stabilized ABS polymer are obtained. The pellets of stabilized ABS polymer are dried before further processing for 3 h at 80° C. (Heliomat 2000 6K).

Dried pellets of stabilized ABS polymer are injection molded at 230° C. to obtain tensile impact bars of 65×10×2 mm (Engel e-mac 100).

Dried pellets of stabilized ABS polymer are compression molded at 230° C. for 3 min to obtain plaques (Suter LP 322, plaques of 2 mm thickness).

TABLE I-1 stabilized ABS polymer with MFI

| example No. | mixture used for obtaining stabilized ABS polymer pellets | MFI (220° C./10 kg) of stabilized ABS polymer pellets [g/10 min]) |
|---|---|---|
| I-1-1 [b)] | 99.80% ABS polymer [c)] (powder)<br>0.20% SM-20 (powder) | 20.4 |
| I-1-2 [a)] | 99.80% ABS polymer (pellet)<br>0.20% TA-1-15 (tablet out of SM-20) | 19.5 |
| I-1-3 [b)] | 99.80% ABS polymer (powder)<br>0.20% SM-13 (powder) | 20.7 |
| I-1-4 [a)] | 99.80% ABS polymer (pellet)<br>0.20% TA-1-7 (tablet out of SM-13) | 19.6 |
| I-1-5 [b)] | 99.90% ABS polymer (powder)<br>0.10% SM-19 (powder) | 21.2 |
| I-1-6 [a)] | 99.90% ABS polymer (pellet)<br>0.10% TA-1-14 (tablet out of SM-19) | 19.8 |

Footnotes:
[a)] according to the invention
[b)] comparative
[c)] Terluran GP-22 from the company Styrolution I-2) Performance of the Stabilized ABS Polymer The melt flow properties of the obtained pellets of stabilized ABS polymer are measured at 220° C./10 kg (melt flow index according to ISO 1133) and the results are shown in table I-1.

Table I-1 shows that the ground ABS shows always an about one unit higher MFI. This is due to the grinding step. Besides this within a range of +/−0.2 units, the melt flow of an inventive examples versus its respective comparative example is in the same range.

For weathering, the plaques with a thickness of 2 mm are exposed to artificial weathering according to DIN EN ISO4892-2 cycle 1 (dry) as shown in table I-2. The discoloration of the plaques is determined by measuring the yellowness index and delta E of yellowness index as shown in table I-2 after the stated time periods of artificial weathering.

TABLE I-2 stabilized ABS polymer with YI and artificial weathering

| Material used for tested specimem from example No. | composition | 0 h | 234 h | 495 h |
|---|---|---|---|---|
| | | yellowness index (YI) | | |
| I-1-3 [b)] | 99.80% ABS [c)]<br>0.20% SM-13 | 20.7 | 27.6 | 37.7 |
| I-1-4 [a)] | 99.80% ABS<br>0.20% TA-1-7 | 21.1 | 29.2 | 39.9 |

TABLE I-2-continued stabilized ABS polymer with YI and artificial weathering

| Material used for tested specimem from example No. | composition | 0 h | 234 h | 495 h |
|---|---|---|---|---|
| | | delta E of yellowness index (YI) | | |
| I-1-3 [b)] | 99.80% ABS<br>0.20% SM-13 | — | 5.7 | 11.6 |
| I-1-4 [a)] | 99.80% ABS<br>0.20% TA-1-7 | — | 4.7 | 11.0 |

Footnotes:
[a)] according to the invention
[b)] comparative
[c)] Terluran GP-22 from the company Styrolution Table I-2 shows that the discoloration behavior measured via yellowness index and delta E of the inventive example versus the comparative example is in the same range.

The invention claimed is:

1. A method for manufacturing a tablet, which comprises the steps of:

(A) filling a starting material, which is in a solid form and consists of a powder, in a first open cavity, which is formed by a first punch and a die, to obtain a second open cavity, which is filled at least partly with the starting material, wherein solid form of the starting material excludes that the starting material is a liquid or a gas, (B) closing the second open cavity by a second punch to obtain a first closed cavity, (C) compressing the starting material at a compression temperature below 37° C. by moving at least one out of the first punch and the second punch to obtain a second closed cavity, which has a smaller volume than the first closed cavity, which results in formation of a trapped tablet of the starting material in the second closed cavity, (D) removing the trapped tablet to obtain the tablet, which has a tablet temperature below 37° C. directly after removal, wherein the steps (A), (B), (C) and (D) are conducted in a tablet press, wherein the starting material is solid at 37° C. and 101.32 KPa and comprises (i) 60 to 100 wt. % of a first polymer stabilizer, which is (i-1) tris(2,4-ditert-butylphenyl) phosphite (CAS-No. 31570-04-4), (i-2) bis(2,4-dicumylphenyl) pentaerythritol diphosphite (CAS-No. 154862-43-8), (i-3) bis(2,4-ditert-butylphenyl)pentaerythritol diphosphite (CAS-No. 26741-53-7), (i-4) tetrakis-[3-(3,5-ditert-butyl-4-hydroxy-phenyl)-propionyloxymethyl]methane (CAS-No. 6683-19-8), (i-5) 3-(3,5-ditert-butyl-4-hydroxy-phenyl)-propionic acid stearyl ester (CAS-No. 2082-79-3), (i-6) 3-(3,5-ditert-butyl-4-hydroxy-phenyl)-N-[6-[3-(3,5-ditert-butyl-4-hydroxy-phenyl)propanoylamino]hexyl]propanamide (CAS-No. 23128-74-7), (i-7) 3-(3,5-ditert-butyl-4-hydroxyphenyl)-N'-[3-(3,5-ditert-butyl-4-hydroxyphenyl)propanoyl]propanehydrazide (CAS-No. 3268-78-8), (i-8) 2-[2-[2-[3-(3-tert-butyl-4-hydroxy-5-methyl-phenyl)propanoyloxy]-ethoxy]ethoxy]ethyl 3-(3-tert-butyl-4-hydroxy-5-methyl-phenyl) propanoate (CAS-No. 36443-68-2), (i-9) 4-[[3,5-bis[(3,5-ditert-butyl-4-hydroxy-phenyl) methyl]-2,4,6-trimethyl-phenyl]methyl]-2,6-ditert-butyl-phenol (CAS-No. 1709-70-2), (i-10) 1,3,5-tris(3,5-ditert-butyl-4-hydroxybenzyl)-1,3,5-triazine-2,4,6-(1H,3H,5H)-trione (CAS-No. 27676-62-6), (i-11) bis[3,3-bis(4'-hydroxy-3'-tert-butylphenyl) butanoic acid] glycol ester (CAS-No. 32509-66-3), (i-12) N,N-dioctadecylhydroxylamine (CAS-No. 123250-74-8), (i-13) dodecyl 3-(3-dodecoxy-3-oxo-propyl)sulfanylpropanoate (CAS-No. 123-28-4), (i-14) octadecyl 3-(3-octadecoxy-3-oxo-propyl)sulfanylpropanoate (CAS-No. 693-36-7), (i-15) pentaerythritol tetrakis[3-dodecylthio proprionate] (CAS-No. 29598-76-3), (i-16) bis(2,2,6,6-tetramethyl-4-piperidyl) decanedioate (CAS-No. 52829-07-9), (i-17) (2-hydroxy-4-octoxy-phenyl)-phenyl-methanone (CAS-No. 1843-05-6), (i-18) 2-tert-butyl-6-(5-chlorobenzotriazol-2-yl)-4-methyl-phenol (CAS-No. 3896-11-5), (i-19) 2-(4,6-diphenyl-1,3,5-triazin-2-yl)-5-hexoxy-phenol (CAS-No. 147315-50-2), (i-20) 2-[4,6-bis(4-phenylphenyl)-1,3,5-triazin-2-yl]-5-(2-ethylhexoxy)phenol (CAS-No. 204583-39-1), (i-21) 2-[4,6-bis(2,4-dimethylphenyl)-1,3,5-triazin-2-yl]-5-[3-(2-ethylhexoxy)-2-hydroxy-propoxy]phenol (CAS-No. 137658-79-8), (i-22) butanedioic acid, 1,4-dimethyl ester, polymer with 4-hydroxy-2,2,6,6-tetramethyl-1-piperidineethanol (CAS-No. 65447-77-0), (i-23) N,N',N",N'"-tetrakis-(2,4-bis[N-(1-cyclohexyloxy-2,2,6,6-tetramethylpiperidin-4-yl)-butylamino]-1,3,5-triazin-6-yl)-1,5,8,12-tetrazadodecane (CAS-No. 122587-07-9), (i-24) N,N',N",N'"-Tetrakis-(2,4-bis[N-(1-cyclohexyloxy-2,2,6,6-tetramethylpiperidin-4-yl)-butylamino]-1,3,5-triazin-6-yl)-1,5,8,12-tetrazadodecane (CAS-No. 106990-43-6), (i-25) N,N'-bis-(2,4-bis[N-(1-propoxy-2,2,6,6-tetramethylpiperidin-4-yl)-butylamino]-1,3,5-triazin)-N,N'-bis[N-(1-propoxy-2,2,6,6-tetramethylpiperidin-4-yl)]-1,8-diazaoctane (CAS-No. 1271737-36-0), (i-26) poly[[6-[butyl(2,2,6,6-tetramethyl-4-piperidinyl) amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]], α-[[6-[[4,6-bis (dibutylamino)-1,3,5-triazin-2-yl](2,2,6,6-tetramethyl-4-piperidinyl)amino]hexyl](2,2,6,6-tetramethyl-4-piperidinyl)amino]-ω-[4,6-bis (dibutylamino)-1,3,5-triazin-2-yl]-(CAS-No. 195300-91-5), (i-27) poly[[6-[butyl(2,2,6,6-tetramethyl-1-propoxy-4-piperidinyl)amino]-1,3,5-triazine-2,4-diyl][(2,2,6,6-tetramethyl-1-propoxy-4-piperidinyl)imino]-1,6-hexanediyl[(2,2,6,6-tetramethyl-1-propoxy-4-piperidinyl)imino]], α-[[6-[[4,6-bis(dibutylamino)-1,3,5-triazin-2-yl](2,2,6,6-tetramethyl-1-propoxy-4-piperidinyl)amino]hexyl](2,2,6,6-tetramethyl-1-propoxy-4-piperidinyl)amino]-ω-[4,6-bis (dibutylamino)-1,3,5-triazin-2-yl]-(CAS-No. 297748-93-7), (i-28) poly[[6[(1,1,3,3-tetramethylbutyl)amino]-1,3,5-triazine-2,4-diyl][(2,2,6,6-tetramethyl-4-piperidinyl) imino]-1,6-hexanediyl[(2,2,6,6-tetramethyl-4-piperidinyl)imino]] (CAS-No. 71878-19-8), (i-29) tetrakis(1,2,2,6,6-pentamethyl-4-piperidyl) butane-1,2,3,4-tetracarboxylate (CAS-No. 91788-83-9), or a mixture thereof, (ii) 0 to 40 wt. % of a second polymer stabilizer, which is zinc stearate, calcium stearate, magnesium stearate or a mixture thereof, (iii) 0 to 34 wt. % of a third polymer stabilizer, which is zinc oxide, hydrotalcite, sodium benzoate or a mixture thereof, (iv) 0 to 20 wt. % of a further ingredient, which is different to the first polymer stabilizer, the second polymer stabilizer and the third polymer stabilizer, wherein the sum of components (i), (ii), (iii) and (iv) is 100 wt. %, wherein the tablet has a weight above 20 mg and below 330 mg and a cross-section dimension above 3 mm and below 18 mm.

2. The method for manufacturing a tablet according to claim 1, wherein the tablet has a geometric form, at which in case a corner is present, each corner possesses only angles directed to an inner side of the tablet above 90° or each corner is convexly rounded, and at which in case of an edge is present, each edge possesses only angles directed to the inner side of the tablet above 90° or each edge is convexly rounded, except in case a corner or an edge originates from an embossed groove.

3. The method for manufacturing a tablet according to claim 1, wherein the tablet has a weight above 55 mg and below 200 mg and a cross-section dimension above 4 mm and below 15 mm.

4. The method for manufacturing a tablet according to claim 1, wherein the starting material has a mean particle size above 15 μm and below 1000 μm as determined by light scattering.

5. The method for manufacturing a tablet according to claim 1, wherein the starting material has a bulk density above 300 g/L and below 950 g/L as determined by DIN EN ISO 17892-3.

6. The method for manufacturing a tablet according to claim 1, wherein the compressing at step (C) takes place with a compression pressure above 90 MPa and below 600 MPa.

7. The method for manufacturing a tablet according to claim 1, wherein the steps (A), (B), (C) and (D) are conducted at a temperature below 37° C.

8. The method for manufacturing a tablet according to claim 1, wherein the compression temperature is below 32° C. and the tablet temperature is below 32° C.

9. The method for manufacturing a tablet according to claim 1, wherein the tablet or a plurality of tablets is not sieved.

10. The method for manufacturing a tablet according to claim 1, wherein the tablet press is an eccentric tablet press or a rotary tablet press.

11. A method for manufacturing a tablet, which comprises the steps of:

(A) filling a starting material, which is in a solid form and does not contain a solvent, in a first open cavity, which is formed by a first punch and a die, to obtain a second open cavity, which is filled at least partly with the starting material, wherein solid form of the starting material excludes that the starting material is a liquid or a gas, (B) closing the second open cavity by a second punch to obtain a first closed cavity, (C) compressing the starting material at a compression temperature below 37° C. by moving at least one out of the first punch and the second punch to obtain a second closed cavity, which has a smaller volume than the first closed cavity, which results in formation of a trapped tablet of the starting material in the second closed cavity, (D) removing the trapped tablet to obtain the tablet, which has a tablet temperature below 37° C. directly after removal, wherein the steps (A), (B), (C) and (D) are conducted in a tablet press, wherein the starting material is solid at 37° C. and 101.32 KPa and comprises (i) 60 to 100 wt. % of a first polymer stabilizer, which is (i-1) tris(2,4-ditert-butylphenyl) phosphite (CAS-No. 31570-04-4), (i-2) bis(2,4-dicumylphenyl) pentaerythritol diphosphite (CAS-No. 154862-43-8), (i-3) bis(2,4-ditert-butylphenyl)pentaerythritol diphosphite (CAS-No. 26741-53-7), (i-4) tetrakis-[3-(3,5-ditert-butyl-4-hydroxy-phenyl)-propionyloxymethyl]methane (CAS-No. 6683-19-8), (i-5) 3-(3,5-ditert-butyl-4-hydroxy-phenyl)-propionic acid stearyl ester (CAS-No. 2082-79-3), (i-6) 3-(3,5-ditert-butyl-4-hydroxy-phenyl)-N-[6-[3-(3,5-ditert-butyl-4-hydroxy-phenyl)propanoylamino]hexyl]propanamide (CAS-No. 23128-74-7), (i-7) 3-(3,5-ditert-butyl-4-hydroxyphenyl)-N'-[3-(3,5-ditert-butyl-4-hydroxyphenyl)propanoyl]propanehydrazide (CAS-No. 3268-78-8), (i-8) 2-[2-[2-[3-(3-tert-butyl-4-hydroxy-5-methyl-phenyl)propanoyloxy]-ethoxy]ethoxy]ethyl 3-(3-tert-butyl-4-hydroxy-5-methyl-phenyl)propanoate (CAS-No. 36443-68-2), (i-9) 4-[[3,5-bis[(3,5-ditert-butyl-4-hydroxy-phenyl)methyl]-2,4,6-trimethyl-phenyl]methyl]-2,6-ditert-butyl-phenol (CAS-No. 1709-70-2), (i-10) 1,3,5-tris(3,5-ditert-butyl-4-hydroxybenzyl)-1,3,5-triazine-2,4,6-(1H,3H,5H)-trione (CAS-No. 27676-62-6), (i-11) bis[3,3-bis(4'-hydroxy-3'-tert-butylphenyl)butanoic acid] glycol ester (CAS-No. 32509-66-3), (i-12) N,N-dioctadecylhydroxylamine (CAS-No. 123250-74-8), (i-13) dodecyl 3-(3-dodecoxy-3-oxo-propyl) sulfanylpropanoate (CAS-No. 123-28-4), (i-14) octadecyl 3-(3-octadecoxy-3-oxo-propyl) sulfanylpropanoate (CAS-No. 693-36-7), (i-15) pentaerythritol tetrakis[3-dodecylthio proprionate] (CAS-No. 29598-76-3), (i-16) bis(2,2,6,6-tetramethyl-4-piperidyl) decanedioate (CAS-No. 52829-07-9), (i-17) (2-hydroxy-4-octoxy-phenyl)-phenyl-methanone (CAS-No. 1843-05-6), (i-18) 2-tert-butyl-6-(5-chlorobenzotriazol-2-yl)-4-methyl-phenol (CAS-No. 3896-11-5), (i-19) 2-(4,6-diphenyl-1,3,5-triazin-2-yl)-5-hexoxy-phenol (CAS-No. 147315-50-2), (i-20) 2-[4,6-bis(4-phenylphenyl)-1,3,5-triazin-2-yl]-5-(2-ethylhexoxy)phenol (CAS-No. 204583-39-1), (i-21) 2-[4,6-bis(2,4-dimethylphenyl)-1,3,5-triazin-2-yl]-5-[3-(2-ethylhexoxy)-2-hydroxy-propoxy]phenol (CAS-No. 137658-79-8), (i-22) butanedioic acid, 1,4-dimethyl ester, polymer with 4-hydroxy-2,2,6,6-tetramethyl-1-piperidineethanol (CAS-No. 65447-77-0), (i-23) N,N',N",N'"-tetrakis-(2,4-bis[N-(1-cyclohexyloxy-2,2,6,6-tetramethylpiperidin-4-yl)-butylamino]-1,3,5-triazin-6-yl)-1,5,8,12-tetrazadodecane (CAS-No. 122587-07-9), (i-24) N,N',N",N'"-Tetrakis-(2,4-bis[N-(1-cyclohexyloxy-2,2,6,6-tetramethylpiperidin-4-yl)-butylamino]-1,3,5-triazin-6-yl)-1,5,8,12-tetrazadodecane (CAS-No. 106990-43-6), (i-25) N,N'-bis-(2,4-bis[N-(1-propoxy-2,2,6,6-tetramethylpiperidin-4-yl)-butylamino]-1,3,5-triazin)-N,N'-bis[N-(1-propoxy-2,2,6,6-tetramethylpiperidin-4-yl)]-1,8-diazaoctane (CAS-No. 1271737-36-0), (i-26) poly[[6-[butyl(2,2,6,6-tetramethyl-4-piperidinyl)amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]], α-[[6-[[4,6-bis(dibutylamino)-1,3,5-triazin-2-yl](2,2,6,6-tetramethyl-4-piperidinyl)amino]hexyl](2,2,6,6-tetramethyl-4-piperidinyl)amino]-ω-[4,6-bis(dibutylamino)-1,3,5-triazin-2-yl]-(CAS-No. 195300-91-5), (i-27) poly[6-[butyl(2,2,6,6-tetramethyl-1-propoxy-4-piperidinyl)amino]-1,3,5-triazine-2,4-diyl][(2,2,6,6-tetramethyl-1-propoxy-4-piperidinyl)imino]-1,6-hexanediyl[(2,2,6,6-tetramethyl-1-propoxy-4-piperidinyl)imino]], α-[[6-[[4,6-bis(dibutylamino)-1,3,5-triazin-2-yl](2,2,6,6-tetramethyl-1-propoxy-4-piperidinyl)amino]hexyl](2,2,6,6-tetramethyl-1-propoxy-4-piperidinyl)amino]-ω[4,6-bis(dibutylamino)-1,3,5-triazin-2-yl]-(CAS-No. 297748-93-7), (i-28) poly[[6 [(1,1,3,3-tetramethylbutyl)amino]-1,3,5-triazine-2,4-diyl][(2,2,6,6-tetramethyl-4-piperidinyl)imino]-1,6-hexanediyl[(2,2,6,6-tetramethyl-4-piperidinyl)imino]] (CAS-No. 71878-19-8), (i-29) tetrakis(1,2,2,6,6-pentamethyl-4-piperidyl) butane-1,2,3,4-tetracarboxylate (CAS-No. 91788-83-9), or a mixture thereof, (ii) 0 to 40 wt. % of a second polymer stabilizer, which is zinc stearate, calcium stearate, magnesium stearate or a mixture thereof, (iii) 0 to 34 wt. % of a third polymer stabilizer, which is zinc oxide, hydrotalcite, sodium benzoate or a mixture thereof, (iv) 0 to 20 wt. % of a further ingredient, which is different to the first polymer stabilizer, the second polymer stabilizer and the third polymer stabilizer, wherein the sum of components (i), (ii), (iii) and (iv) is 100 wt. %, wherein the tablet has a weight above 20 mg and below 330 mg and a cross-section dimension above 3 mm and below 18 mm.

* * * * *